(12) United States Patent
Weston

(10) Patent No.: US 10,058,642 B2
(45) Date of Patent: Aug. 28, 2018

(54) REDUCED PRESSURE TREATMENT SYSTEM

(75) Inventor: Richard Scott Weston, Encinitas, CA (US)

(73) Assignee: BlueSky Medical Group Incorporated, Memphis, TN (US)

( * ) Notice: Subject to any disclaimer, the term of this patent is extended or adjusted under 35 U.S.C. 154(b) by 1261 days.

(21) Appl. No.: 12/941,390

(22) Filed: Nov. 8, 2010

(65) Prior Publication Data

US 2011/0118683 A1     May 19, 2011

Related U.S. Application Data

(63) Continuation-in-part of application No. 12/719,715, filed on Mar. 8, 2010, now Pat. No. 8,303,552, which is a continuation of application No. 11/098,203, filed on Apr. 4, 2005, now Pat. No. 7,708,724, application No. 12/941,390, which is a continuation-in-part of application No. 11/064,813, filed on Feb. 24, 2005, now Pat. No. 8,062,272, and a continuation-in-part of application No. 11/098,265, filed on Apr. 4, 2005, now Pat. No. 7,909,805, which is a continuation of
(Continued)

(51) Int. Cl.
*A61M 1/00*     (2006.01)
*A61F 5/048*     (2006.01)

(52) U.S. Cl.
CPC ........... *A61M 1/0023* (2013.01); *A61F 5/048* (2013.01); *A61M 1/0056* (2013.01); *A61M 1/0072* (2014.02); *A61M 1/0088* (2013.01)

(58) Field of Classification Search
CPC .............. A61M 1/0001; A61M 1/0005; A61M 1/0023; A61M 1/0025; A61M 1/0049; A61M 1/0056; A61M 1/0088
See application file for complete search history.

(56) References Cited

U.S. PATENT DOCUMENTS

| 70,088 A | 10/1867 | Hadfield |
|---|---|---|
| 695,270 A | 3/1902 | Beringer |

(Continued)

FOREIGN PATENT DOCUMENTS

| CA | 1111204 A1 | 10/1981 |
|---|---|---|
| CA | 1305586 C | 6/1988 |

(Continued)

OTHER PUBLICATIONS

US 6,216,701, 04/2001, Heaton et al. (withdrawn)
(Continued)

*Primary Examiner* — Lynne Anderson
(74) *Attorney, Agent, or Firm* — Knobbe, Martens, Olson & Bear LLP

(57) ABSTRACT

A wound treatment appliance is provided for treating all or a portion of a wound. In some embodiments, the appliance comprises a cover or a flexible overlay that covers all or a portion of the wound for purposes of applying a reduced pressure to the covered portion of the wound. In other embodiments, the wound treatment appliance also includes a vacuum system to supply reduced pressure to the site of the wound in the volume under the cover or in the area under the flexible overlay. Methods are provided for using various embodiments of the invention.

27 Claims, 12 Drawing Sheets

Related U.S. Application Data application No. 11/064,813, filed on Feb. 24, 2005, now Pat. No. 8,062,272.

(60) Provisional application No. 60/559,727, filed on Apr. 5, 2004, provisional application No. 60/573,655, filed on May 21, 2004.

(56) References Cited

U.S. PATENT DOCUMENTS

| | | |
|---|---|---|
| 765,746 A | 7/1904 | Miner |
| 774,529 A | 11/1904 | Nieschange |
| 846,674 A | 7/1907 | Funk |
| 1,066,934 A | 7/1913 | Manney |
| 1,355,679 A | 10/1920 | McConnell |
| 1,355,846 A | 10/1920 | Rannells |
| 1,385,346 A | 7/1921 | Taylor |
| 1,480,562 A | 1/1924 | Mock |
| 1,585,104 A | 5/1926 | Montgomery |
| 1,732,310 A | 12/1929 | Naibert |
| 1,863,534 A | 6/1932 | Odell |
| 1,936,129 A | 11/1933 | Fisk |
| 2,122,121 A | 6/1938 | Tillotson |
| 2,195,771 A | 4/1940 | Estler |
| 2,232,254 A | 2/1941 | Morgan |
| 2,280,915 A | 4/1941 | Johnson |
| 2,318,888 A | 5/1943 | Sanders |
| 2,338,339 A | 1/1944 | La Mere et al. |
| 2,366,799 A | 1/1945 | Luisada |
| 2,367,690 A | 1/1945 | Purdy |
| 2,385,683 A | 9/1945 | Burton |
| 2,547,758 A | 4/1951 | Keeling |
| 2,568,933 A | 9/1951 | Robbins |
| 2,632,443 A | 3/1953 | Lesher |
| 2,682,873 A | 7/1954 | Evans et al. |
| 2,910,763 A | 8/1955 | Lauterbach |
| 2,927,577 A | 3/1960 | Nicolaie |
| 2,969,057 A | 1/1961 | Simmons |
| 3,026,526 A | 3/1962 | Montrose |
| 3,026,874 A | 3/1962 | Stevens et al. |
| 3,042,041 A | 7/1962 | Jascalevich |
| 3,060,932 A | 10/1962 | Pereny et al. |
| 3,115,138 A | 12/1963 | McElvenny et al. |
| 3,123,074 A | 3/1964 | Turner |
| 3,217,707 A | 11/1965 | Werding |
| 3,238,056 A | 3/1966 | Pall et al. |
| 3,238,937 A | 3/1966 | Stein |
| 3,286,711 A | 11/1966 | MacLeod |
| 3,288,140 A | 11/1966 | McCarthy |
| 3,315,665 A | 4/1967 | MacLeod et al. |
| 3,367,332 A * | 2/1968 | Groves .................. 604/290 |
| 3,376,868 A | 4/1968 | Mondiadis |
| 3,465,748 A | 9/1969 | Kravchenko |
| 3,478,736 A | 11/1969 | Roberts et al. |
| 3,486,504 A * | 12/1969 | Austin, Jr. ......... A61F 13/00063 |
| | | 401/132 |
| 3,520,300 A | 7/1970 | Flower, Jr. |
| 3,568,675 A | 3/1971 | Harvey |
| 3,572,340 A | 3/1971 | Lloyd et al. |
| 3,610,238 A | 10/1971 | Rich et al. |
| 3,624,821 A | 11/1971 | Henderson |
| 3,682,180 A | 8/1972 | McFarlane |
| 3,712,298 A | 1/1973 | Snowdon et al. |
| 3,763,857 A | 10/1973 | Schrading et al. |
| 3,783,870 A | 1/1974 | Schachet |
| 3,794,035 A | 2/1974 | Brenner |
| 3,826,254 A | 7/1974 | Mellor |
| 3,847,387 A | 11/1974 | Sick |
| 3,859,989 A | 1/1975 | Spielberg |
| 3,871,377 A | 3/1975 | Treace et al. |
| 3,874,387 A | 4/1975 | Barbieri |
| 3,896,810 A | 7/1975 | Akiyama |
| 3,908,642 A | 9/1975 | Vinmont |
| 3,908,664 A | 9/1975 | Loseff |
| 3,938,540 A | 2/1976 | Holbrook et al. |
| 3,954,105 A | 5/1976 | Nordby et al. |
| 3,961,625 A | 6/1976 | Dillon |
| 3,972,328 A | 8/1976 | Chen |
| 3,988,793 A | 11/1976 | Abitbol |
| 3,993,080 A | 11/1976 | Loseff |
| RE29,319 E | 7/1977 | Nordby et al. |
| 4,073,294 A | 2/1978 | Stanley et al. |
| 4,080,970 A | 3/1978 | Miller |
| 4,102,342 A | 7/1978 | Akiyama et al. |
| 4,112,947 A | 9/1978 | Nehring |
| 4,117,551 A | 9/1978 | Books et al. |
| 4,136,696 A | 1/1979 | Nehring |
| 4,149,541 A | 4/1979 | Gammons et al. |
| 4,169,563 A | 10/1979 | Leu |
| 4,172,455 A | 10/1979 | Beaussant |
| 4,178,938 A | 12/1979 | Au |
| 4,180,074 A | 12/1979 | Murry et al. |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,228,798 A | 10/1980 | Deaton |
| 4,250,882 A | 2/1981 | Adair |
| 4,252,119 A | 2/1981 | Coates |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,278,089 A | 7/1981 | Huck et al. |
| 4,297,995 A | 11/1981 | Golub |
| 4,316,466 A | 2/1982 | Babb |
| 4,341,207 A | 7/1982 | Steer et al. |
| 4,360,015 A | 11/1982 | Mayer |
| 4,360,021 A | 11/1982 | Stima |
| 4,373,519 A | 2/1983 | Errede et al. |
| 4,382,441 A | 5/1983 | Svedman |
| 4,392,853 A | 7/1983 | Muto |
| 4,392,860 A | 7/1983 | Huck et al. |
| 4,418,691 A | 12/1983 | Yannas et al. |
| 4,419,097 A | 12/1983 | Rowland |
| 4,421,109 A | 12/1983 | Thornton |
| 4,432,354 A | 2/1984 | Lasley |
| 4,444,548 A | 4/1984 | Andersen et al. |
| 4,459,139 A | 7/1984 | vonReis et al. |
| 4,465,485 A * | 8/1984 | Kashmer et al. ............. 604/320 |
| 4,468,227 A | 8/1984 | Jensen |
| 4,469,092 A | 9/1984 | Marshall et al. |
| 4,475,909 A | 10/1984 | Eisenberg |
| 4,480,638 A * | 11/1984 | Schmid ...................... 602/53 |
| 4,499,896 A | 2/1985 | Heinecke |
| 4,524,064 A | 6/1985 | Nambu |
| 4,525,166 A | 6/1985 | Laclerc |
| 4,527,064 A | 7/1985 | Anderson |
| 4,529,402 A | 7/1985 | Weilbacher et al. |
| 4,534,356 A | 8/1985 | Papadakis |
| 4,538,920 A | 9/1985 | Drake et al. |
| 4,540,412 A | 9/1985 | Van Overloop |
| 4,543,100 A | 9/1985 | Brodsky |
| 4,551,141 A | 11/1985 | McNeil |
| 4,561,435 A | 12/1985 | McKnight et al. |
| 4,569,674 A | 2/1986 | Phillips |
| 4,573,965 A | 3/1986 | Russo |
| 4,578,060 A | 3/1986 | Huck et al. |
| 4,587,101 A | 5/1986 | Marsoner et al. |
| 4,605,399 A | 8/1986 | Weston et al. |
| 4,608,041 A | 8/1986 | Nielsen |
| 4,624,656 A | 11/1986 | Clark et al. |
| 4,640,688 A | 2/1987 | Hauser |
| 4,655,202 A | 4/1987 | Potter et al. |
| 4,655,754 A | 4/1987 | Richmond et al. |
| 4,655,766 A | 4/1987 | Theeuwes et al. |
| 4,661,093 A | 4/1987 | Beck et al. |
| 4,664,662 A | 5/1987 | Webster |
| 4,681,562 A | 7/1987 | Beck et al. |
| 4,691,695 A | 9/1987 | Birk et al. |
| 4,699,134 A | 10/1987 | Samuelsen |
| 4,710,165 A | 12/1987 | McNeil et al. |
| 4,713,052 A | 12/1987 | Beck et al. |
| 4,717,382 A | 1/1988 | Clemens et al. |

(56) References Cited

U.S. PATENT DOCUMENTS

| | | |
|---|---|---|
| 4,738,249 A | 4/1988 | Linman |
| 4,740,202 A | 4/1988 | Stacey et al. |
| 4,743,232 A | 5/1988 | Kruger |
| 4,753,231 A | 6/1988 | Lang et al. |
| 4,753,536 A | 6/1988 | Spehar et al. |
| 4,759,354 A | 7/1988 | Quarfoot |
| 4,764,167 A | 8/1988 | Tu |
| 4,765,316 A | 8/1988 | Marshall |
| 4,767,026 A | 8/1988 | Keller |
| 4,771,919 A | 9/1988 | Ernst |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,798,583 A | 1/1989 | Beck et al. |
| 4,798,603 A | 1/1989 | Meyer et al. |
| 4,813,931 A | 3/1989 | Hauze |
| 4,817,594 A | 4/1989 | Juhasz |
| 4,820,265 A | 4/1989 | DeSatnick et al. |
| 4,820,284 A | 4/1989 | Hauri |
| 4,826,494 A | 5/1989 | Richmond et al. |
| 4,828,546 A | 5/1989 | McNeil et al. |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,847,083 A | 7/1989 | Clark |
| 4,851,545 A | 7/1989 | Song et al. |
| 4,863,449 A | 9/1989 | Therriault et al. |
| 4,867,150 A | 9/1989 | Gilbert |
| 4,872,450 A | 10/1989 | Austad |
| 4,875,473 A | 10/1989 | Alvarez |
| 4,878,901 A | 11/1989 | Sachse |
| 4,882,213 A | 11/1989 | Gaddis et al. |
| 4,902,277 A | 2/1990 | Marhies et al. |
| 4,906,233 A | 3/1990 | Moriuchi et al. |
| 4,917,112 A | 4/1990 | Kalt |
| 4,921,488 A | 5/1990 | Maitz et al. |
| 4,921,492 A | 5/1990 | Schultz |
| 4,923,444 A | 5/1990 | Daoud et al. |
| 4,925,447 A | 5/1990 | Rosenblatt |
| 4,929,477 A | 5/1990 | Will |
| 4,931,519 A | 6/1990 | Song et al. |
| 4,936,834 A | 6/1990 | Beck et al. |
| 4,941,882 A | 7/1990 | Ward et al. |
| 4,950,483 A | 8/1990 | Ksander et al. |
| 4,953,565 A | 9/1990 | Tachibana et al. |
| 4,955,893 A | 9/1990 | Yannas et al. |
| 4,969,880 A | 11/1990 | Zamierowski |
| 4,969,881 A | 11/1990 | Viesturs |
| 4,972,829 A | 11/1990 | Knerr |
| 4,979,944 A | 12/1990 | Luzsicza |
| 4,994,022 A | 2/1991 | Steffler et al. |
| 4,997,425 A | 3/1991 | Shioya et al. |
| 5,000,164 A | 3/1991 | Cooper |
| 5,009,635 A | 4/1991 | Scarberry |
| 5,030,202 A | 7/1991 | Harris |
| 5,034,006 A | 7/1991 | Hosoda et al. |
| 5,035,884 A | 7/1991 | Song et al. |
| 5,055,198 A | 10/1991 | Shettigar |
| 5,056,510 A * | 10/1991 | Gilman ............... A61F 13/02 128/888 |
| 5,064,653 A | 11/1991 | Sessions et al. |
| 5,073,172 A | 12/1991 | Fell |
| 5,080,493 A | 1/1992 | McKown et al. |
| 5,080,661 A | 1/1992 | Lavender et al. |
| 5,086,763 A | 2/1992 | Hathman |
| 5,086,764 A | 2/1992 | Gilman |
| 5,088,483 A | 2/1992 | Heinecke |
| 5,089,606 A | 2/1992 | Cole et al. |
| 5,100,395 A | 3/1992 | Rosenberg |
| 5,100,396 A | 3/1992 | Zamierowski |
| 5,106,362 A | 4/1992 | Gilman |
| 5,106,629 A | 4/1992 | Cartmell et al. |
| 5,112,323 A | 5/1992 | Winkler et al. |
| 5,113,871 A | 5/1992 | Viljanto et al. |
| 5,134,994 A | 8/1992 | Say |
| 5,141,503 A | 8/1992 | Sewell, Jr. |
| 5,149,331 A | 9/1992 | Ferdman et al. |
| 5,152,757 A | 10/1992 | Eriksson |
| 5,160,315 A | 11/1992 | Heinecke et al. |
| 5,167,613 A | 12/1992 | Karami et al. |
| 5,176,663 A | 1/1993 | Svedman et al. |
| 5,184,077 A | 2/1993 | Day et al. |
| 5,201,780 A | 4/1993 | Dinsmoor et al. |
| 5,215,519 A | 6/1993 | Shettigar |
| 5,218,973 A | 6/1993 | Weaver et al. |
| 5,228,431 A | 7/1993 | Giarretto |
| 5,234,419 A | 8/1993 | Bryant et al. |
| 5,238,732 A | 8/1993 | Krishnan |
| 5,243,968 A | 9/1993 | Byun |
| 5,249,709 A | 10/1993 | Duckworth et al. |
| 5,261,893 A | 11/1993 | Zamierowski |
| 5,263,922 A * | 11/1993 | Soya ............... A61F 13/00068 128/203.11 |
| 5,264,218 A | 11/1993 | Rogozinski |
| 5,266,928 A | 11/1993 | Johnson |
| 5,279,608 A | 1/1994 | Cherif Cheikh |
| 5,288,431 A | 2/1994 | Huber et al. |
| 5,307,791 A | 5/1994 | Senoue et al. |
| 5,322,695 A | 6/1994 | Shah et al. |
| 5,328,614 A | 7/1994 | Matsumura |
| 5,330,448 A * | 7/1994 | Chu ..................... A61M 39/18 604/175 |
| 5,333,760 A | 8/1994 | Simmen et al. |
| 5,336,209 A | 8/1994 | Porzilli |
| 5,350,360 A * | 9/1994 | Ensminger ........ A61M 39/0208 604/175 |
| 5,358,494 A | 10/1994 | Svedman |
| 5,360,398 A | 11/1994 | Grieshaber et al. |
| 5,362,543 A | 11/1994 | Nickerson |
| 5,380,280 A | 1/1995 | Peterson |
| 5,425,742 A | 6/1995 | Joy |
| 5,437,651 A | 8/1995 | Todd et al. |
| 5,445,604 A | 8/1995 | Lang |
| 5,462,514 A | 10/1995 | Harris |
| 5,466,229 A | 11/1995 | Elson |
| 5,478,333 A | 12/1995 | Asherman, Jr. |
| 5,479,333 A | 12/1995 | McCambridge et al. |
| 5,486,158 A | 1/1996 | Samuelsen |
| 5,487,889 A | 1/1996 | Eckert et al. |
| 5,489,280 A | 2/1996 | Russell |
| 5,489,304 A | 2/1996 | Orgill et al. |
| 5,490,984 A | 2/1996 | Freed |
| 5,496,605 A | 3/1996 | Augst et al. |
| 5,498,338 A | 3/1996 | Kruger et al. |
| 5,514,166 A | 5/1996 | Silver et al. |
| 5,527,293 A | 6/1996 | Zamierowski |
| 5,531,855 A | 7/1996 | Heinecke et al. |
| 5,549,584 A | 8/1996 | Gross |
| 5,549,585 A | 8/1996 | Maher et al. |
| 5,563,233 A | 10/1996 | Reich et al. |
| 5,577,994 A | 11/1996 | Celik |
| 5,582,596 A | 12/1996 | Fukunaga et al. |
| 5,593,395 A | 1/1997 | Martz |
| 5,599,289 A | 2/1997 | Castellana |
| 5,609,271 A | 3/1997 | Keller et al. |
| 5,616,387 A | 4/1997 | Augst et al. |
| 5,618,556 A | 4/1997 | Johns et al. |
| 5,624,423 A | 4/1997 | Anjur et al. |
| 5,633,007 A | 5/1997 | Webb et al. |
| 5,636,643 A | 6/1997 | Argenta et al. |
| 5,643,189 A | 7/1997 | Masini |
| 5,645,081 A | 7/1997 | Argenta et al. |
| 5,645,981 A | 7/1997 | Romanet et al. |
| 5,676,650 A | 10/1997 | Grieshaber et al. |
| 5,678,564 A | 10/1997 | Lawrence et al. |
| 5,681,579 A | 10/1997 | Freeman |
| 5,688,225 A | 11/1997 | Walker |
| 5,701,917 A | 12/1997 | Khouri |
| 5,707,499 A | 1/1998 | Joshi et al. |
| 5,713,881 A | 2/1998 | Rezai et al. |
| 5,714,225 A | 2/1998 | Hansen et al. |

(56) References Cited

U.S. PATENT DOCUMENTS

| | | |
|---|---|---|
| 5,716,411 A | 2/1998 | Orgill et al. |
| 5,733,305 A | 3/1998 | Fleischmann |
| 5,733,337 A | 3/1998 | Carr et al. |
| 5,759,570 A | 6/1998 | Arnold |
| 5,785,688 A | 7/1998 | Joshi et al. |
| 5,792,090 A | 8/1998 | Ladin |
| 5,810,755 A | 9/1998 | LeVeen et al. |
| 5,827,246 A | 10/1998 | Bowen |
| 5,830,176 A | 11/1998 | Mackool |
| 5,830,496 A | 11/1998 | Freeman |
| 5,833,646 A | 11/1998 | Masini |
| 5,840,777 A | 11/1998 | Eagles et al. |
| 5,843,011 A | 12/1998 | Lucas |
| 5,857,502 A | 1/1999 | Buchalter |
| 5,868,933 A | 2/1999 | Patrick et al. |
| 5,876,387 A | 3/1999 | Killian et al. |
| 5,876,611 A | 3/1999 | Shettigar |
| 5,885,237 A | 3/1999 | Kadash |
| 5,893,368 A | 4/1999 | Sugerman |
| 5,899,893 A | 5/1999 | Dyer et al. |
| 5,904,659 A | 5/1999 | Duarte |
| 5,911,222 A | 6/1999 | Lawrence et al. |
| 5,938,626 A | 8/1999 | Sugerman |
| 5,941,859 A | 8/1999 | Lerman |
| 5,944,703 A | 8/1999 | Dixon et al. |
| 5,954,680 A | 9/1999 | Augustine |
| 5,958,420 A | 9/1999 | Jenson |
| 5,964,723 A | 10/1999 | Augustine |
| 5,970,266 A | 10/1999 | Takato |
| 5,981,822 A | 11/1999 | Addison |
| 5,985,990 A | 11/1999 | Kantner et al. |
| 6,042,560 A | 3/2000 | Niederberger |
| 6,045,541 A | 4/2000 | Matsumoto |
| 6,071,267 A | 6/2000 | Zamierowski |
| 6,087,549 A | 7/2000 | Flick |
| 6,103,951 A | 8/2000 | Freeman |
| 6,110,197 A | 8/2000 | Augustine et al. |
| D430,674 S | 9/2000 | Dunshee et al. |
| 6,113,548 A | 9/2000 | deBoisblanc et al. |
| 6,117,111 A | 9/2000 | Fleischmann |
| 6,117,444 A | 9/2000 | Orgill et al. |
| 6,135,116 A | 10/2000 | Vogel et al. |
| 6,135,166 A | 10/2000 | Paradies et al. |
| D434,150 S | 11/2000 | Turney et al. |
| 6,142,982 A | 11/2000 | Hunt et al. |
| 6,168,800 B1 | 1/2001 | Dobos et al. |
| 6,174,306 B1 | 1/2001 | Fleischmann |
| 6,176,307 B1 | 1/2001 | Danos et al. |
| 6,179,804 B1 | 1/2001 | Satterfield |
| D439,341 S | 3/2001 | Tumey et al. |
| 6,200,596 B1 | 3/2001 | Schwartzmiller et al. |
| 6,203,563 B1 | 3/2001 | Fernandez |
| 6,225,523 B1 | 5/2001 | Masini |
| 6,252,129 B1 | 6/2001 | Coffee |
| 6,254,567 B1 | 7/2001 | Treu et al. |
| 6,255,552 B1 | 7/2001 | Cummings et al. |
| 6,261,276 B1 | 7/2001 | Reitsma |
| 6,261,283 B1 | 7/2001 | Morgan et al. |
| 6,287,521 B1 | 9/2001 | Quay et al. |
| 6,291,050 B1 | 9/2001 | Cree et al. |
| 6,293,281 B1 | 9/2001 | Shultz et al. |
| 6,345,623 B1 | 2/2002 | Heaton et al. |
| 6,350,339 B1 | 2/2002 | Sessions |
| 6,368,311 B1 | 4/2002 | Valerio |
| 6,371,976 B1 | 4/2002 | Vrzalik |
| 6,391,294 B1 | 5/2002 | Dettmar et al. |
| 6,398,761 B1 | 6/2002 | Bills et al. |
| 6,398,767 B1 | 6/2002 | Fleischmann |
| 6,402,724 B1 | 6/2002 | Smith et al. |
| 6,442,413 B1 | 8/2002 | Silver |
| 6,450,773 B1 | 9/2002 | Upton |
| 6,458,109 B1 | 10/2002 | Henley |
| 6,465,708 B1 | 10/2002 | Augustine |
| 6,471,685 B1 | 10/2002 | Johnson |
| 6,471,982 B1 | 10/2002 | Lydon et al. |
| 6,481,986 B1 | 11/2002 | Silver et al. |
| 6,482,491 B1 | 11/2002 | Samuelsen et al. |
| 6,486,285 B2 | 11/2002 | Fujita |
| 6,488,643 B1 | 12/2002 | Tumey et al. |
| 6,491,684 B1 | 12/2002 | Joshi et al. |
| 6,509,391 B2 | 1/2003 | Gothjaelpsen et al. |
| 6,520,982 B1 | 2/2003 | Boynton et al. |
| 6,527,203 B2 | 3/2003 | Hurray et al. |
| 6,536,056 B1 | 3/2003 | Vrzalik et al. |
| 6,553,998 B2 | 4/2003 | Heaton et al. |
| 6,557,704 B1 | 5/2003 | Randolph |
| 6,564,972 B2 | 5/2003 | Sawhney et al. |
| 6,566,833 B2 | 5/2003 | Bartlett |
| 6,569,113 B2 | 5/2003 | Wirt et al. |
| 6,595,949 B1 | 7/2003 | Shapiro |
| 6,599,262 B1 | 7/2003 | Masini |
| 6,626,827 B1 | 9/2003 | Felix et al. |
| 6,626,891 B2 | 9/2003 | Ohmstede |
| 6,629,774 B1 | 10/2003 | Guruendeman |
| 6,648,862 B2 | 11/2003 | Watson |
| 6,673,028 B1 | 1/2004 | Argenta et al. |
| 6,676,610 B2 | 1/2004 | Morton et al. |
| 6,680,113 B1 | 1/2004 | Lucast et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| 6,730,299 B1 | 5/2004 | Tayot et al. |
| 6,732,887 B2 | 5/2004 | Bills |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,775,807 B2 | 8/2004 | Lowther et al. |
| 6,794,554 B2 | 9/2004 | Sessions et al. |
| 6,797,855 B2 | 9/2004 | Worthley |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,872,196 B1 * | 3/2005 | Bryan ................ A61M 35/00 604/23 |
| 6,904,631 B2 | 6/2005 | Vrzalik et al. |
| 6,936,037 B2 | 8/2005 | Bubb |
| 6,942,633 B2 | 9/2005 | Odland |
| 6,942,634 B2 | 9/2005 | Odland |
| 6,945,987 B2 | 9/2005 | Beard et al. |
| 6,951,553 B2 | 10/2005 | Bubb et al. |
| 6,974,428 B2 | 12/2005 | Knutson et al. |
| 6,977,323 B1 | 12/2005 | Swenson |
| 6,979,324 B2 | 12/2005 | Bybordi et al. |
| 6,988,423 B2 | 1/2006 | Bolam et al. |
| 6,994,702 B1 | 2/2006 | Johnson |
| 7,004,915 B2 | 2/2006 | Boynton et al. |
| 7,005,556 B1 | 2/2006 | Becker et al. |
| 7,022,113 B2 | 4/2006 | Lockwood et al. |
| 7,030,288 B2 | 4/2006 | Liedtke et al. |
| 7,041,868 B2 | 5/2006 | Greene et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| 7,137,968 B1 | 11/2006 | Burrell et al. |
| 7,141,714 B2 | 11/2006 | Nielsen |
| 7,144,390 B1 | 12/2006 | Hanningan et al. |
| 7,175,336 B2 | 2/2007 | Voellmicke et al. |
| 7,182,758 B2 | 2/2007 | McCraw |
| 7,195,624 B2 | 3/2007 | Lockwood |
| 7,198,046 B1 | 4/2007 | Argenta et al. |
| 7,214,202 B1 | 5/2007 | Vogel et al. |
| 7,216,651 B2 | 5/2007 | Argenta et al. |

(56) References Cited

U.S. PATENT DOCUMENTS

| | | |
|---|---|---|
| 7,238,850 B2 | 7/2007 | Shimanuki |
| 7,276,051 B1 | 10/2007 | Henley et al. |
| 7,279,612 B1 * | 10/2007 | Heaton et al. ............ 602/42 |
| 7,291,762 B2 | 11/2007 | Flick |
| 7,335,809 B2 | 2/2008 | Riesinger |
| 7,338,482 B2 | 3/2008 | Lockwood et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,447,327 B2 | 11/2008 | Kitamura et al. |
| 7,470,830 B2 | 12/2008 | Sigurjonsson et al. |
| 7,485,112 B2 | 2/2009 | Karpowicz et al. |
| 7,494,482 B2 | 2/2009 | Orgill et al. |
| 7,518,031 B2 | 4/2009 | Liedtke et al. |
| 7,524,315 B2 | 4/2009 | Blott et al. |
| 7,534,240 B1 | 5/2009 | Johnson |
| 7,534,927 B2 | 5/2009 | Lockwood et al. |
| 7,540,848 B2 | 6/2009 | Hannigan et al. |
| 7,569,742 B2 | 8/2009 | Haggstrom et al. |
| 7,601,129 B2 | 10/2009 | Aali |
| 7,611,500 B1 | 11/2009 | Lina et al. |
| 7,615,036 B2 | 11/2009 | Buan |
| 7,625,362 B2 | 12/2009 | Boehringer et al. |
| 7,645,253 B2 | 1/2010 | Gura et al. |
| 7,645,269 B2 | 1/2010 | Zamierowski |
| 7,674,837 B2 | 3/2010 | Gaserod et al. |
| 7,678,090 B2 | 3/2010 | Risk, Jr. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,722,582 B2 | 5/2010 | Lina et al. |
| 7,723,560 B2 | 5/2010 | Lockwood et al. |
| 7,745,681 B1 | 6/2010 | Ferguson |
| 7,753,894 B2 | 7/2010 | Blott et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,799,004 B2 | 9/2010 | Tumey |
| 7,830,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,825,289 B2 | 11/2010 | Vess |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,862,339 B2 | 1/2011 | Mulligan |
| 7,880,050 B2 | 2/2011 | Robinson et al. |
| 7,883,494 B2 | 2/2011 | Martin |
| 7,884,258 B2 | 2/2011 | Boehringer et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,998,125 B2 | 8/2011 | Weston |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,084,663 B2 | 12/2011 | Watson, Jr. |
| 8,096,979 B2 | 1/2012 | Lina et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,152,785 B2 | 4/2012 | Vitaris |
| 8,162,907 B2 | 4/2012 | Heagle |
| 8,162,909 B2 | 4/2012 | Blott et al. |
| 8,168,848 B2 | 5/2012 | Lockwood |
| 8,192,409 B2 | 6/2012 | Hardman et al. |
| 8,207,392 B2 | 6/2012 | Haggstrom et al. |
| 8,211,071 B2 | 7/2012 | Mormino et al. |
| 8,235,955 B2 | 8/2012 | Blott et al. |
| 8,241,261 B2 | 8/2012 | Randolph et al. |
| 8,257,326 B2 | 9/2012 | Vitaris |
| 8,257,327 B2 | 9/2012 | Blott et al. |
| 8,282,611 B2 | 10/2012 | Weston |
| 8,303,552 B2 | 11/2012 | Weston |
| 8,348,910 B2 | 1/2013 | Blott et al. |
| 8,366,692 B2 | 2/2013 | Weston et al. |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,399,730 B2 | 3/2013 | Kazala, Jr. et al. |
| D679,819 S | 4/2013 | Peron |
| D679,820 S | 4/2013 | Peron |
| 8,409,157 B2 | 4/2013 | Haggstrom et al. |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,529,548 B2 | 9/2013 | Blott et al. |
| 8,545,464 B2 | 10/2013 | Weston |
| 8,551,061 B2 | 10/2013 | Hartwell |
| 8,556,871 B2 | 10/2013 | Mormino et al. |
| 8,613,734 B2 | 12/2013 | Lina et al. |
| 8,628,505 B2 | 1/2014 | Weston |
| 8,641,690 B2 | 2/2014 | Fitzpatrick et al. |
| 8,641,691 B2 | 2/2014 | Fink |
| 8,680,360 B2 | 3/2014 | Greener et al. |
| 8,715,256 B2 | 5/2014 | Greener |
| 8,758,313 B2 | 6/2014 | Blott et al. |
| 8,808,274 B2 | 8/2014 | Hartwell |
| 8,834,451 B2 | 9/2014 | Blott et al. |
| 8,845,619 B2 | 9/2014 | Blott et al. |
| 8,882,746 B2 | 11/2014 | Blott et al. |
| 8,945,030 B2 | 2/2015 | Weston |
| 9,023,012 B2 | 5/2015 | Tout et al. |
| 9,205,001 B2 | 12/2015 | Blott et al. |
| 9,211,365 B2 | 12/2015 | Weston |
| 9,272,080 B2 | 3/2016 | Weston |
| 9,345,823 B2 | 5/2016 | Mormino et al. |
| 2001/0004082 A1 | 6/2001 | Keller et al. |
| 2001/0016205 A1 | 8/2001 | Shimizu |
| 2001/0027285 A1 | 10/2001 | Heinecke et al. |
| 2001/0029956 A1 | 10/2001 | Argenta et al. |
| 2001/0031943 A1 | 10/2001 | Urie |
| 2001/0034499 A1 | 10/2001 | Sessions et al. |
| 2001/0043943 A1 | 11/2001 | Coffey |
| 2001/0051781 A1 * | 12/2001 | Augustine et al. ............ 602/41 |
| 2002/0002209 A1 | 1/2002 | Mork |
| 2002/0038826 A1 | 4/2002 | Hurray et al. |
| 2002/0065494 A1 | 5/2002 | Lockwood et al. |
| 2002/0068913 A1 | 6/2002 | Fleischmann |
| 2002/0082567 A1 | 6/2002 | Lockwood et al. |
| 2002/0114847 A1 | 8/2002 | Peshoff |
| 2002/0115952 A1 | 8/2002 | Johnson et al. |
| 2002/0120185 A1 | 8/2002 | Johnson |
| 2002/0128578 A1 | 9/2002 | Johnston et al. |
| 2002/0143286 A1 | 10/2002 | Tumey |
| 2002/0145007 A1 | 10/2002 | Sawhney et al. |
| 2002/0150720 A1 | 10/2002 | Howard et al. |
| 2002/0161345 A1 * | 10/2002 | McMillin ............ A61M 35/00 604/304 |
| 2002/0161346 A1 | 10/2002 | Lockwood et al. |
| 2002/0183702 A1 | 12/2002 | Henley et al. |
| 2002/0198490 A1 | 12/2002 | Wirt et al. |

(56) References Cited

U.S. PATENT DOCUMENTS

| | | |
|---|---|---|
| 2002/0198503 A1 | 12/2002 | Risk et al. |
| 2002/0198504 A1 | 12/2002 | Risk et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0078532 A1 | 4/2003 | Ruszczak et al. |
| 2003/0088202 A1 | 5/2003 | Gilman |
| 2003/0093041 A1 | 5/2003 | Risk, Jr. et al. |
| 2003/0097086 A1 | 5/2003 | Gura |
| 2003/0097100 A1 | 5/2003 | Watson |
| 2003/0108587 A1 | 6/2003 | Orgill et al. |
| 2003/0125649 A1 | 6/2003 | McIntosh et al. |
| 2003/0125646 A1 | 7/2003 | Whitlock |
| 2003/0134332 A1 | 7/2003 | Boykin |
| 2003/0144619 A1 | 7/2003 | Augustine |
| 2003/0148959 A1 | 8/2003 | Quirk et al. |
| 2003/0171675 A1 | 9/2003 | Rosenberg |
| 2003/0175798 A1 | 9/2003 | Raees et al. |
| 2003/0183653 A1 | 10/2003 | Bills |
| 2003/0208149 A1 | 11/2003 | Coffey |
| 2003/0211137 A1 | 11/2003 | Sierra |
| 2003/0212357 A1 | 11/2003 | Pace |
| 2003/0212359 A1 | 11/2003 | Butler |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0006319 A1 | 1/2004 | Lina et al. |
| 2004/0019342 A1 | 1/2004 | Nagasuna et al. |
| 2004/0030304 A1* | 2/2004 | Hunt .................. A61M 1/0088 604/317 |
| 2004/0033466 A1 | 2/2004 | Shellard et al. |
| 2004/0039391 A1 | 2/2004 | Argenta et al. |
| 2004/0039415 A1 | 2/2004 | Zamierowski |
| 2004/0050411 A1 | 3/2004 | Lawrence |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0073151 A1* | 4/2004 | Weston ........................... 602/41 |
| 2004/0093026 A1 | 5/2004 | Weidenhagen et al. |
| 2004/0121438 A1 | 6/2004 | Quirk |
| 2004/0122434 A1 | 6/2004 | Argenta et al. |
| 2004/0127834 A1 | 7/2004 | Sigurjonsson et al. |
| 2004/0127862 A1 | 7/2004 | Bubb et al. |
| 2004/0127863 A1* | 7/2004 | Bubb et al. .................. 604/317 |
| 2004/0138601 A1 | 7/2004 | Chalmers |
| 2004/0162512 A1 | 8/2004 | Liedtke et al. |
| 2004/0167482 A1 | 8/2004 | Watson |
| 2004/0167617 A1 | 8/2004 | Voellmicke et al. |
| 2004/0171998 A1 | 9/2004 | Marasco, Jr. |
| 2004/0193218 A1 | 9/2004 | Butler |
| 2004/0225208 A1 | 11/2004 | Johnson |
| 2004/0241213 A1 | 12/2004 | Bray |
| 2004/0241214 A1 | 12/2004 | Kirkwood et al. |
| 2004/0243105 A1* | 12/2004 | Swan .................. A61M 1/0013 604/543 |
| 2004/0249353 A1 | 12/2004 | Risk, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0028828 A1 | 2/2005 | Heaton et al. |
| 2005/0058694 A1 | 3/2005 | Nielsen |
| 2005/0070835 A1 | 3/2005 | Joshi |
| 2005/0070858 A1 | 3/2005 | Lockwood et al. |
| 2005/0080372 A1 | 4/2005 | Nielsen et al. |
| 2005/0085795 A1* | 4/2005 | Lockwood et al. .......... 604/543 |
| 2005/0090787 A1 | 4/2005 | Risk, Jr. et al. |
| 2005/0113733 A1 | 5/2005 | Liedtke et al. |
| 2005/0130299 A1 | 6/2005 | Suzuki |
| 2005/0131327 A1 | 6/2005 | Lockwood et al. |
| 2005/0137272 A1 | 6/2005 | Gaserod et al. |
| 2005/0137539 A1 | 6/2005 | Biggie et al. |
| 2005/0143697 A1 | 6/2005 | Riesinger |
| 2005/0147562 A1 | 7/2005 | Hunter et al. |
| 2005/0148913 A1 | 7/2005 | Weston |
| 2005/0163904 A1 | 7/2005 | Walker et al. |
| 2005/0177190 A1 | 8/2005 | Zamierowski |
| 2005/0181163 A1 | 8/2005 | Kose |
| 2005/0203452 A1 | 9/2005 | Weston et al. |
| 2005/0222527 A1 | 10/2005 | Miller et al. |
| 2005/0222528 A1 | 10/2005 | Weston |
| 2005/0222544 A1 | 10/2005 | Weston |
| 2005/0230422 A1 | 10/2005 | Muller et al. |
| 2005/0261615 A1 | 11/2005 | Weston |
| 2005/0261642 A1 | 11/2005 | Weston |
| 2005/0261643 A1 | 11/2005 | Bybordi et al. |
| 2005/0269374 A1 | 12/2005 | Koerner et al. |
| 2006/0001382 A1 | 1/2006 | Nomoto |
| 2006/0009744 A1 | 1/2006 | Edrman et al. |
| 2006/0015087 A1 | 1/2006 | Risk, Jr. et al. |
| 2006/0024727 A1 | 2/2006 | Boehringer et al. |
| 2006/0025727 A1 | 2/2006 | Boehringer et al. |
| 2006/0029650 A1 | 2/2006 | Coffey |
| 2006/0029675 A1 | 2/2006 | Ginther |
| 2006/0041247 A1 | 2/2006 | Petrosenko et al. |
| 2006/0069365 A1 | 3/2006 | Sperl et al. |
| 2006/0070458 A1 | 4/2006 | Jones et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0142687 A1 | 6/2006 | Liedtke et al. |
| 2006/0149170 A1 | 7/2006 | Boynton et al. |
| 2006/0155260 A1 | 7/2006 | Blott et al. |
| 2006/0173253 A1 | 8/2006 | Ganapathy et al. |
| 2006/0178608 A1 | 8/2006 | Stapf |
| 2006/0225787 A1 | 10/2006 | Newrones et al. |
| 2006/0228057 A1 | 10/2006 | Newrones et al. |
| 2006/0241689 A1 | 10/2006 | Leiboff et al. |
| 2006/0273109 A1 | 12/2006 | Keller |
| 2007/0010797 A1 | 1/2007 | Nishtala et al. |
| 2007/0014837 A1 | 1/2007 | Johnson et al. |
| 2007/0167926 A1 | 1/2007 | Blott et al. |
| 2007/0032762 A1 | 2/2007 | Vogel |
| 2007/0038172 A1 | 2/2007 | Zamierowski |
| 2007/0055209 A1 | 3/2007 | Patel et al. |
| 2007/0066945 A1 | 3/2007 | Martin |
| 2007/0073200 A1 | 3/2007 | Hannigan et al. |
| 2007/0129707 A1 | 6/2007 | Blott et al. |
| 2007/0141128 A1 | 6/2007 | Blott et al. |
| 2007/0142761 A1 | 6/2007 | Aali |
| 2007/0167884 A1 | 7/2007 | Mangrum et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0219497 A1 | 9/2007 | Johnson et al. |
| 2007/0219513 A1 | 9/2007 | Lina et al. |
| 2007/0219532 A1 | 9/2007 | Karpowicz et al. |
| 2007/0225663 A1 | 9/2007 | Watt et al. |
| 2007/0233022 A1 | 10/2007 | Henley et al. |
| 2007/0237811 A1 | 10/2007 | Scherr |
| 2007/0239139 A1 | 10/2007 | Weston et al. |
| 2007/0260207 A1 | 11/2007 | Ugander et al. |
| 2007/0265585 A1 | 11/2007 | Joshi et al. |
| 2007/0265586 A1 | 11/2007 | Joshi et al. |
| 2007/0292488 A1 | 12/2007 | Bassiri et al. |
| 2007/0293830 A1 | 12/2007 | Martin |
| 2008/0004549 A1 | 1/2008 | Anderson et al. |
| 2008/0004559 A1 | 1/2008 | Riesinger |
| 2008/0039759 A1 | 2/2008 | Holm et al. |
| 2008/0069855 A1 | 3/2008 | Bonutti |
| 2008/0077091 A1 | 3/2008 | Mulligan |
| 2008/0082059 A1 | 4/2008 | Fink et al. |
| 2008/0095979 A1 | 4/2008 | Hatanaka et al. |
| 2008/0108977 A1 | 5/2008 | Heaton et al. |
| 2008/0119802 A1 | 5/2008 | Reisinger |
| 2008/0132819 A1 | 6/2008 | Radl et al. |
| 2008/0167593 A1 | 7/2008 | Fleischmann |
| 2008/0183119 A1 | 7/2008 | Joshi |
| 2008/0188820 A1 | 8/2008 | Joshi |
| 2008/0208147 A1 | 8/2008 | Argenta et al. |

(56) References Cited

U.S. PATENT DOCUMENTS

| | | |
|---|---|---|
| 2008/0213344 A1 | 9/2008 | McCarthy et al. |
| 2008/0223378 A1 | 9/2008 | Henderson et al. |
| 2008/0243044 A1 | 10/2008 | Hunt et al. |
| 2008/0306407 A1 | 12/2008 | Taylor |
| 2008/0306456 A1 | 12/2008 | Riesinger |
| 2008/0312572 A1 | 12/2008 | Riesinger |
| 2009/0005746 A1 | 1/2009 | Nielsen et al. |
| 2009/0012483 A1 | 1/2009 | Blott et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0069759 A1 | 3/2009 | Blott et al. |
| 2009/0082740 A1 | 3/2009 | Lockwood et al. |
| 2009/0099519 A1 | 4/2009 | Kaplan |
| 2009/0105671 A1 | 4/2009 | Daggar et al. |
| 2009/0124988 A1 | 5/2009 | Coulthard |
| 2009/0125004 A1 | 5/2009 | Shen et al. |
| 2009/0130186 A1 | 5/2009 | McCarthy et al. |
| 2009/0131888 A1 | 5/2009 | Joshi |
| 2009/0131892 A1 | 5/2009 | Karpowicz et al. |
| 2009/0137973 A1 | 5/2009 | Karpowicz et al. |
| 2009/0143753 A1 | 6/2009 | Blott et al. |
| 2009/0177135 A1 | 7/2009 | Rogers et al. |
| 2009/0177136 A1 | 7/2009 | Liedtke et al. |
| 2009/0192499 A1 | 7/2009 | Weston et al. |
| 2009/0198201 A1 | 8/2009 | Adahan |
| 2009/0204084 A1 | 8/2009 | Blott et al. |
| 2009/0204085 A1 | 8/2009 | Biggie et al. |
| 2009/0216170 A1 | 8/2009 | Robinson et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234260 A1 | 9/2009 | Coward et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0254054 A1 | 10/2009 | Blott et al. |
| 2009/0264837 A1 | 10/2009 | Adahan |
| 2009/0270820 A1 | 10/2009 | Johnson et al. |
| 2009/0275872 A1 | 11/2009 | Addison et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299308 A1 | 12/2009 | Kazala, Jr. et al. |
| 2009/0299340 A1 | 12/2009 | Kazala, Jr. et al. |
| 2009/0299341 A1 | 12/2009 | Kazala, Jr. et al. |
| 2009/0299342 A1 | 12/2009 | Cavanaugh, II et al. |
| 2009/0306580 A1 | 12/2009 | Blott et al. |
| 2009/0306609 A1 | 12/2009 | Blott et al. |
| 2009/0312723 A1 | 12/2009 | Blott et al. |
| 2009/0312727 A1 | 12/2009 | Heaton |
| 2009/0312728 A1 | 12/2009 | Randolph et al. |
| 2009/0326487 A1 | 12/2009 | Vitaris |
| 2010/0004611 A1 | 1/2010 | Aali |
| 2010/0010477 A1 | 1/2010 | Augustine et al. |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0036367 A1 | 2/2010 | Krohn |
| 2010/0042074 A1 | 2/2010 | Weston et al. |
| 2010/0063481 A1 | 3/2010 | Heagle |
| 2010/0063483 A1 | 3/2010 | Adahan |
| 2010/0063484 A1 | 3/2010 | Heagle |
| 2010/0069829 A1 | 3/2010 | Hutchinson et al. |
| 2010/0069858 A1 | 3/2010 | Olson |
| 2010/0069863 A1 | 3/2010 | Olson |
| 2010/0069885 A1 | 3/2010 | Stevenson et al. |
| 2010/0087767 A1 | 4/2010 | McNeil |
| 2010/0100022 A1 | 4/2010 | Greener et al. |
| 2010/0100063 A1 | 4/2010 | Joshi et al. |
| 2010/0100075 A1 | 4/2010 | Weston et al. |
| 2010/0106112 A1 | 4/2010 | Vogel |
| 2010/0106114 A1 | 4/2010 | Weston et al. |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0135915 A1 | 6/2010 | Greener et al. |
| 2010/0150991 A1 | 6/2010 | Bernstein |
| 2010/0159192 A1 | 6/2010 | Cotton |
| 2010/0160879 A1 | 6/2010 | Weston |
| 2010/0160880 A1 | 6/2010 | Weston |
| 2010/0185163 A1 | 6/2010 | Heagle |
| 2010/0174251 A1 | 7/2010 | Weston |
| 2010/0191196 A1 | 7/2010 | Heagle |
| 2010/0191198 A1 | 7/2010 | Heagle |
| 2010/0207768 A1 | 8/2010 | Pidgeon et al. |
| 2010/0210986 A1 | 8/2010 | Sanders et al. |
| 2010/0211030 A1 | 8/2010 | Turner et al. |
| 2010/0211031 A1 | 8/2010 | Hartwell et al. |
| 2010/0249733 A9 | 9/2010 | Blott et al. |
| 2010/0262090 A1 | 10/2010 | Riesinger |
| 2010/0268198 A1 | 10/2010 | Buan et al. |
| 2010/0274207 A1 | 10/2010 | Weston |
| 2010/0278518 A1 | 11/2010 | Gordon |
| 2010/0280468 A1 | 11/2010 | Haggstrom et al. |
| 2010/0286635 A1 | 11/2010 | Watson, Jr. |
| 2010/0286638 A1 | 11/2010 | Malhi |
| 2010/0297208 A1 | 11/2010 | Fry et al. |
| 2010/0298866 A1 | 11/2010 | Fischvogt |
| 2010/0305490 A1 | 12/2010 | Coulthard et al. |
| 2010/0305524 A1 | 12/2010 | Vess et al. |
| 2010/0305526 A1 | 12/2010 | Robinson et al. |
| 2010/0305549 A1 | 12/2010 | Miller |
| 2010/0318043 A1 | 12/2010 | Malhi et al. |
| 2010/0324510 A1 | 12/2010 | Andresen et al. |
| 2010/0324516 A1 | 12/2010 | Braga et al. |
| 2010/0331797 A1 | 12/2010 | Patel et al. |
| 2011/0004171 A1 | 1/2011 | Blott et al. |
| 2011/0004172 A1 | 1/2011 | Eckstein et al. |
| 2011/0009835 A1 | 1/2011 | Blott et al. |
| 2011/0009838 A1 | 1/2011 | Greener |
| 2011/0015593 A1 | 1/2011 | Svedman et al. |
| 2011/0028290 A1 | 2/2011 | Johannison |
| 2011/0028918 A1 | 2/2011 | Hartwell |
| 2011/0028919 A1 | 2/2011 | Johnnison et al. |
| 2011/0028921 A1 | 2/2011 | Hartwell et al. |
| 2011/0034888 A1 | 2/2011 | Aali |
| 2011/0034892 A1 | 2/2011 | Buan |
| 2011/0046584 A1 | 2/2011 | Haggstrom et al. |
| 2011/0054421 A1 | 3/2011 | Hartwell et al. |
| 2011/0054422 A1 | 3/2011 | Locke et al. |
| 2011/0054423 A1 | 3/2011 | Blott et al. |
| 2011/0087176 A2 | 4/2011 | Blott et al. |
| 2011/0087178 A2 | 4/2011 | Weston |
| 2011/0087179 A2 | 4/2011 | Blott et al. |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125066 A1 | 5/2011 | Robinson et al. |
| 2011/0130712 A1 | 6/2011 | Topaz |
| 2011/0172612 A1 | 7/2011 | Greener |
| 2011/0172615 A2 | 7/2011 | Greener |
| 2011/0172617 A1 | 7/2011 | Riesinger |
| 2011/0178451 A1 | 7/2011 | Robinson et al. |
| 2011/0213287 A1 | 9/2011 | Lattimore et al. |
| 2011/0213320 A1 | 9/2011 | Blott et al. |
| 2011/0224631 A1 | 9/2011 | Simmons |
| 2011/0230849 A1 | 9/2011 | Coulthard et al. |
| 2011/0251567 A1 | 10/2011 | Blott et al. |

(56) References Cited

U.S. PATENT DOCUMENTS

| | | | |
|---|---|---|---|
| 2011/0251569 A1 | 10/2011 | Turner et al. |
| 2011/0282309 A1 | 11/2011 | Adie et al. |
| 2012/0004628 A1 | 1/2012 | Blott et al. |
| 2012/0041399 A1 | 2/2012 | Blott et al. |
| 2012/0053538 A1 | 3/2012 | Blott et al. |
| 2012/0083755 A1 | 4/2012 | Lina et al. |
| 2012/0109084 A1 | 5/2012 | Blott et al. |
| 2012/0123356 A1 | 5/2012 | Greener |
| 2012/0130325 A1 | 5/2012 | Blott et al. |
| 2012/0136325 A1 | 5/2012 | Allen et al. |
| 2012/0157942 A1 | 6/2012 | Weston |
| 2012/0209224 A1 | 8/2012 | Weston |
| 2013/0096519 A1 | 4/2013 | Blott |
| 2013/0110058 A1 | 5/2013 | Adie et al. |
| 2013/0116635 A1 | 5/2013 | Fleischmann |
| 2013/0116641 A1 | 5/2013 | Hicks |
| 2013/0138054 A1 | 5/2013 | Fleischmann |
| 2013/0138060 A1 | 5/2013 | Haqqstrom et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0267921 A1 | 10/2013 | Weston |
| 2013/0274688 A1 | 10/2013 | Weston |
| 2013/0331822 A1 | 12/2013 | Patel et al. |
| 2013/0338613 A1 | 12/2013 | Haggstrom et al. |
| 2014/0012214 A1 | 1/2014 | Miller |
| 2014/0018753 A1 | 1/2014 | Ashok et al. |
| 2014/0094761 A1 | 4/2014 | Corley |
| 2014/0236109 A1 | 4/2014 | Greener |
| 2014/0163493 A1 | 6/2014 | Weston |
| 2014/0228791 A1 | 8/2014 | Hartwell |
| 2014/0249493 A1 | 9/2014 | Hartwell |
| 2014/0249495 A1 | 9/2014 | Mumby et al. |
| 2014/0316359 A1 | 10/2014 | Collinson et al. |
| 2014/0371691 A1 | 12/2014 | Blott et al. |
| 2015/0065966 A1 | 3/2015 | Adie et al. |
| 2015/0073361 A1 | 3/2015 | Pratt et al. |
| 2015/0080788 A1 | 3/2015 | Blott et al. |
| 2015/0157508 A1 | 6/2015 | Blott et al. |
| 2015/0165101 A1 | 6/2015 | Blott et al. |
| 2015/0173954 A1 | 6/2015 | Blott et al. |
| 2015/0174306 A1 | 6/2015 | Blott et al. |
| 2015/0190559 A1 | 7/2015 | Locke et al. |
| 2015/0209492 A1 | 7/2015 | Blott et al. |
| 2016/0206790 A1 | 7/2016 | Weston |
| 2016/0256613 A1 | 9/2016 | Weston |

FOREIGN PATENT DOCUMENTS

| | | | |
|---|---|---|---|
| CA | 1305587 C | 6/1988 |
| CA | 2057000 C | 5/1990 |
| CA | 2115746 C | 8/1992 |
| CA | 1309560 C | 11/1992 |
| CA | 1320888 C | 8/1993 |
| CA | 2198243 A1 | 2/1996 |
| CA | 2214804 A1 | 2/1996 |
| CA | 2238413 A1 | 5/1997 |
| CA | 2280808 A1 | 2/1998 |
| CA | 2280817 A1 | 2/1998 |
| CA | 2272372 A1 | 5/1998 |
| CA | 2285470 A1 | 9/1998 |
| CA | 2471780 A1 | 3/1999 |
| CA | 2331555 A1 | 6/1999 |
| CA | 2347115 A1 | 4/2000 |
| CA | 2367460 A1 | 10/2000 |
| CA | 2390513 A1 | 5/2001 |
| CA | 2121688 C | 7/2001 |
| CA | 2 369 022 | 10/2001 |
| CA | 2408305 A1 | 11/2001 |
| CA | 2254999 C | 4/2002 |
| CA | 2351342 A1 | 6/2002 |
| CA | 2042768 C | 8/2002 |
| CA | 2442724 A1 | 10/2002 |
| CA | 2432293 A1 | 2/2003 |
| CA | 2458285 A1 | 3/2003 |
| CA | 2157772 C | 9/2003 |
| CA | 2486274 A1 | 9/2004 |
| CA | 2349638 C | 6/2005 |
| CA | 2216791 C | 7/2005 |
| CA | 2240732 C | 9/2006 |
| DE | 561757 C | 10/1932 |
| DE | 847475 C | 8/1952 |
| DE | 1963258 | 6/1971 |
| DE | 2809828 | 9/1978 |
| DE | 3032092 A1 | 8/1980 |
| DE | 3137839 A1 | 3/1983 |
| DE | 3539533 A1 | 5/1987 |
| DE | 3935818 A1 | 5/1991 |
| DE | 40 12 232 A1 | 10/1991 |
| DE | 4 016 034 | 11/1991 |
| DE | 4 102 684 | 8/1992 |
| DE | 4111122 A1 | 4/1993 |
| DE | 2 950 4378 | 10/1995 |
| DE | 2 961 8426 | 2/1997 |
| DE | 198 44 355 | 4/2000 |
| DE | 20 2004 017 052 | 7/2005 |
| DE | 20 2005 019 670 U1 | 6/2006 |
| EP | 0020662 B1 | 7/1984 |
| EP | 0 099 748 B1 | 5/1987 |
| EP | 0122085 B1 | 6/1987 |
| EP | 0 355 536 A2 | 2/1990 |
| EP | 0355186 A | 2/1990 |
| EP | 0 358 302 A2 | 3/1990 |
| EP | 0485657 A1 | 5/1992 |
| EP | 0 521 434 A1 | 7/1993 |
| EP | 0 325 771 B1 | 9/1993 |
| EP | 0 425 164 B1 | 9/1994 |
| EP | 0619105 A1 | 10/1994 |
| EP | 0418607 B1 | 12/1994 |
| EP | 0 648 122 A1 | 4/1995 |
| EP | 0 651 983 A1 | 5/1995 |
| EP | 0392640 B1 | 6/1995 |
| EP | 0441418 B1 | 7/1995 |
| EP | 0670705 B1 | 9/1995 |
| EP | 0 690 736 A1 | 1/1996 |
| EP | 0 724 888 A1 | 8/1996 |
| EP | 0 733 375 A2 | 9/1996 |
| EP | 0 754 064 A1 | 1/1997 |
| EP | 0465601 B1 | 1/1997 |
| EP | 0 762 860 A1 | 3/1997 |
| EP | 0 772 464 A1 | 5/1997 |
| EP | 0762860 B1 | 12/1997 |
| EP | 0 537 559 B1 | 1/1998 |
| EP | 0880953 B1 | 5/1998 |
| EP | 0 853 950 A1 | 7/1998 |
| EP | 0 856 318 A1 | 8/1998 |
| EP | 0 858 810 A2 | 8/1998 |
| EP | 0617938 B1 | 8/1998 |
| EP | 0 651 983 B1 | 9/1998 |
| EP | 0651983 B1 | 9/1998 |
| EP | 0777504 B1 | 10/1998 |
| EP | 0 876 165 A1 | 11/1998 |
| EP | 0 888 141 A1 | 1/1999 |
| EP | 0 912 251 A1 | 5/1999 |
| EP | 0782421 B1 | 7/1999 |
| EP | 0638301 B1 | 9/1999 |
| EP | 1068451 A1 | 10/1999 |
| EP | 1 007 015 A1 | 6/2000 |
| EP | 1013290 A1 | 6/2000 |
| EP | 1 021 180 A1 | 7/2000 |
| EP | 1 029 585 A1 | 8/2000 |
| EP | 1 030 657 A1 | 8/2000 |
| EP | 0 688 189 B1 | 9/2000 |
| EP | 0 993 833 A3 | 10/2000 |
| EP | 1169071 A1 | 10/2000 |
| EP | 0690706 B1 | 11/2000 |
| EP | 1 068 451 A1 | 1/2001 |
| EP | 1 085 925 A1 | 3/2001 |
| EP | 1 088 589 A2 | 4/2001 |
| EP | 1 105 110 A1 | 6/2001 |
| EP | 1 105 171 A2 | 6/2001 |
| EP | 1 105 180 A1 | 6/2001 |
| EP | 1 107 813 A1 | 6/2001 |
| EP | 0865304 B1 | 7/2001 |

(56) References Cited

FOREIGN PATENT DOCUMENTS

| | | |
|---|---|---|
| EP | 1411874 A1 | 7/2001 |
| EP | 1 138 336 A1 | 10/2001 |
| EP | 1 156 839 A1 | 11/2001 |
| EP | 1283702 A1 | 11/2001 |
| EP | 0921775 B1 | 12/2001 |
| EP | 0 564 502 B1 | 1/2002 |
| EP | 1 169 071 A1 | 1/2002 |
| EP | 1339366 A2 | 6/2002 |
| EP | 1 218 437 A1 | 7/2002 |
| EP | 1 219 311 A2 | 7/2002 |
| EP | 0875222 B1 | 7/2002 |
| EP | 1897569 B1 | 8/2002 |
| EP | 0 853 950 B1 | 10/2002 |
| EP | 1 283 702 A1 | 2/2003 |
| EP | 1 306 123 A1 | 2/2003 |
| EP | 0708620 B1 | 5/2003 |
| EP | 1088569 B1 | 8/2003 |
| EP | 1 339 366 A2 | 9/2003 |
| EP | 0993317 B1 | 9/2003 |
| EP | 0 880 953 B1 | 10/2003 |
| EP | 1565219 A2 | 12/2003 |
| EP | 1 411 874 A1 | 4/2004 |
| EP | 1 440 667 A1 | 7/2004 |
| EP | 1 440 737 A1 | 7/2004 |
| EP | 1219311 B1 | 7/2004 |
| EP | 1578477 A2 | 7/2004 |
| EP | 1018967 B1 | 8/2004 |
| EP | 1488 816 A1 | 12/2004 |
| EP | 0688189 B1 | 6/2005 |
| EP | 1 632 252 A1 | 3/2006 |
| EP | 1440667 B1 | 3/2006 |
| EP | 1284777 B1 | 4/2006 |
| EP | 1807032 A1 | 5/2006 |
| EP | 1 263 366 B1 | 7/2006 |
| EP | 0982015 B1 | 8/2006 |
| EP | 0620720 B2 | 11/2006 |
| EP | 1923077 B1 | 11/2006 |
| EP | 1904137 A2 | 1/2007 |
| EP | 1448261 B1 | 2/2007 |
| EP | 1171065 B1 | 3/2007 |
| EP | 1922045 A2 | 3/2007 |
| EP | 1931413 A2 | 4/2007 |
| EP | 2021047 A2 | 12/2007 |
| EP | 1880840 A1 | 1/2008 |
| EP | 2059204 A2 | 1/2008 |
| EP | 1 897 569 A1 | 3/2008 |
| EP | 1476217 B1 | 3/2008 |
| EP | 2079507 A2 | 4/2008 |
| EP | 2106255 A2 | 7/2008 |
| EP | 2109472 A1 | 8/2008 |
| EP | 1121163 B1 | 11/2008 |
| EP | 2185206 A2 | 1/2009 |
| EP | 2178573 A2 | 2/2009 |
| EP | 1 897 569 B1 | 3/2009 |
| EP | 2203137 A1 | 4/2009 |
| EP | 1772160 B1 | 6/2009 |
| EP | 2098257 A1 | 9/2009 |
| EP | 2244746 A2 | 9/2009 |
| EP | 2254537 A2 | 9/2009 |
| EP | 2 111 804 A3 | 10/2009 |
| EP | 1513478 B1 | 12/2009 |
| EP | 1985270 A3 | 12/2009 |
| EP | 1637088 B1 | 1/2010 |
| EP | 2326295 A1 | 3/2010 |
| EP | 2172164 A1 | 4/2010 |
| EP | 1807031 B1 | 7/2010 |
| EP | 2253353 A1 | 11/2010 |
| EP | 2 255 837 A1 | 12/2010 |
| EP | 2004116 B1 | 6/2011 |
| EP | 2335749 A1 | 6/2011 |
| EP | 2349155 A2 | 8/2011 |
| EP | 1263366 B2 | 9/2011 |
| EP | 2420214 A1 | 2/2012 |
| EP | 2 021 046 B1 | 3/2012 |
| EP | 2 462 908 | 6/2012 |
| EP | 2 544 642 | 1/2015 |
| EP | 2 648 668 | 1/2015 |
| EP | 2 830 555 | 2/2015 |
| EP | 2 836 711 | 2/2015 |
| EP | 2 814 556 A4 | 7/2015 |
| FR | 1 163 907 | 10/1958 |
| GB | 114754 | 4/1918 |
| GB | 236350 | 7/1925 |
| GB | 641061 | 8/1950 |
| GB | 1063066 A | 3/1967 |
| GB | 1 224 009 A | 3/1971 |
| GB | 1273342 A | 5/1972 |
| GB | 1400124 B | 7/1975 |
| GB | 1522086 A | 8/1978 |
| GB | 1549756 A | 8/1979 |
| GB | 2085305 A | 1/1985 |
| GB | 2195255 A | 4/1988 |
| GB | 2288734 A | 11/1995 |
| GB | 2305610 A | 4/1997 |
| GB | 2307180 A | 5/1997 |
| GB | 2336546 A | 10/1999 |
| GB | 2 344 531 A | 6/2000 |
| GB | 2329127 B | 8/2000 |
| GB | 2378392 A | 2/2003 |
| GB | 2357286 B | 11/2003 |
| GB | 2389794 A1 | 12/2003 |
| GB | 2365350 B | 8/2004 |
| GB | 2415908 A | 1/2006 |
| GB | 2418738 A | 4/2006 |
| GB | 2422545 A | 8/2006 |
| GB | 2423019 A | 8/2006 |
| GB | 2424581 A | 10/2006 |
| GB | 2424582 A | 10/2006 |
| GB | 2435419 A | 2/2007 |
| JP | 59-502014 A | 12/1984 |
| JP | H08-024344 A | 1/1996 |
| JP | H11-069660 A | 3/1999 |
| JP | 2001-314479 A | 11/2001 |
| JP | 2002-035133 A | 2/2002 |
| JP | 2003-165843 | 6/2003 |
| JP | 2004-121819 A | 4/2004 |
| JP | 2005-261376 A | 9/2005 |
| JP | 2006-262647 A | 9/2006 |
| NL | 1 005 726 C2 | 10/1998 |
| SU | 240188 | 3/1969 |
| SU | 1251912 A1 | 8/1986 |
| SU | 1762940 A1 | 9/1992 |
| WO | WO 1980/01139 | 6/1980 |
| WO | WO 1980/02182 | 10/1980 |
| WO | WO 84/01904 | 5/1984 |
| WO | WO 1987/00759 | 2/1987 |
| WO | WO 1987/04626 | 8/1987 |
| WO | WO 1989/05133 | 6/1989 |
| WO | WO 90/11795 | 10/1990 |
| WO | WO 91/00718 | 1/1991 |
| WO | WO 1991/16030 | 10/1991 |
| WO | WO 1992/09651 | 6/1992 |
| WO | WO 1992/13713 | 8/1992 |
| WO | WO 92/20299 | 11/1992 |
| WO | WO 1992/19313 | 11/1992 |
| WO | WO 1993/00056 | 1/1993 |
| WO | WO 1993/06802 | 4/1993 |
| WO | WO 1993/09176 | 5/1993 |
| WO | WO 1993/09727 | 5/1993 |
| WO | WO 1994/20041 | 9/1994 |
| WO | WO 1994/020133 | 9/1994 |
| WO | WO 1995/03838 | 2/1995 |
| WO | WO 1996/00760 | 1/1996 |
| WO | WO 96/05873 | 2/1996 |
| WO | WO 1996/24316 | 8/1996 |
| WO | WO 1996/40174 | 12/1996 |
| WO | WO 1997/03717 | 2/1997 |
| WO | WO 1997/05685 | 2/1997 |
| WO | WO 1997/13520 | 4/1997 |
| WO | WO 1997/18737 | 5/1997 |
| WO | WO 1997/033643 | 9/1997 |
| WO | WO 1997/33922 | 9/1997 |
| WO | WO 1997/042986 | 11/1997 |
| WO | WO 1997/43991 | 11/1997 |

(56) References Cited

FOREIGN PATENT DOCUMENTS

| | | |
|---|---|---|
| WO | WO 1998/06444 | 2/1998 |
| WO | WO 1998/13000 | 4/1998 |
| WO | WO 1998/38955 | 9/1998 |
| WO | WO 1999/01173 A1 | 1/1999 |
| WO | WO 1999/15121 | 4/1999 |
| WO | WO 1999/17698 | 4/1999 |
| WO | WO 1999/23010 | 5/1999 |
| WO | WO 1999/30629 | 6/1999 |
| WO | WO 1999/047097 | 9/1999 |
| WO | WO 1999/64081 | 12/1999 |
| WO | WO 1999/65536 | 12/1999 |
| WO | WO 00/07653 | 2/2000 |
| WO | WO 2000/09199 | 2/2000 |
| WO | WO 00/21586 | 4/2000 |
| WO | WO 2000/038752 | 7/2000 |
| WO | WO 00/50143 A | 8/2000 |
| WO | WO 00/59424 | 10/2000 |
| WO | WO 2000/59418 | 10/2000 |
| WO | WO 2000/59424 | 10/2000 |
| WO | WO 2000/61046 | 10/2000 |
| WO | WO 2000/61206 | 10/2000 |
| WO | WO 2000/62827 | 10/2000 |
| WO | WO 2000/064396 | 11/2000 |
| WO | WO 2001/005443 | 1/2001 |
| WO | WO 01/19430 A1 | 3/2001 |
| WO | WO 2001/19430 | 3/2001 |
| WO | WO 2001/024709 | 4/2001 |
| WO | WO 01/34223 | 5/2001 |
| WO | WO 2001/34223 | 5/2001 |
| WO | WO 2001/35882 | 5/2001 |
| WO | WO 2001/37773 | 5/2001 |
| WO | WO 2001/037922 | 5/2001 |
| WO | WO 2001/041779 | 6/2001 |
| WO | WO 2001/49233 | 7/2001 |
| WO | WO 2001/062312 | 8/2001 |
| WO | WO 2001/066017 | 9/2001 |
| WO | WO 01/85248 | 11/2001 |
| WO | WO 2001/85248 | 11/2001 |
| WO | WO 2001/93793 | 12/2001 |
| WO | WO 2002/000268 | 1/2002 |
| WO | WO 2002/02079 | 1/2002 |
| WO | WO 2002/05737 | 1/2002 |
| WO | WO 2002/09765 | 2/2002 |
| WO | WO 2002/20026 | 3/2002 |
| WO | WO 2002/26180 | 4/2002 |
| WO | WO 2002/034304 | 5/2002 |
| WO | WO 2002/39940 | 5/2002 |
| WO | WO 2002/41878 | 5/2002 |
| WO | WO 2002/45761 | 6/2002 |
| WO | WO 2002/064182 | 8/2002 |
| WO | WO 02/083046 A1 | 10/2002 |
| WO | WO 2002/091965 | 11/2002 |
| WO | WO 2002/092783 A2 | 11/2002 |
| WO | WO 2002/094256 | 11/2002 |
| WO | WO 2002/102864 | 12/2002 |
| WO | WO 03/005943 | 1/2003 |
| WO | WO 2003/009796 | 2/2003 |
| WO | WO 03/018098 | 3/2003 |
| WO | WO 2003/020358 | 3/2003 |
| WO | WO 03/030966 | 4/2003 |
| WO | WO 2003/041686 | 5/2003 |
| WO | WO 2003/045492 | 6/2003 |
| WO | WO 03/057070 | 7/2003 |
| WO | WO 03/057071 | 7/2003 |
| WO | WO 2003/057307 | 7/2003 |
| WO | WO 2003/063923 | 8/2003 |
| WO | WO 2003/071991 | 9/2003 |
| WO | WO 2003/073970 | 9/2003 |
| WO | WO 03/086232 | 10/2003 |
| WO | WO 2003/092620 | 11/2003 |
| WO | WO 2003/092620 A2 | 11/2003 |
| WO | WO 03/101508 | 12/2003 |
| WO | WO 2003/074100 | 12/2003 |
| WO | WO 2003/101385 | 12/2003 |
| WO | WO 2004/012678 | 2/2004 |
| WO | WO 04/024300 | 3/2004 |
| WO | WO 2004/018020 | 3/2004 |
| WO | WO 2004/032977 | 4/2004 |
| WO | WO 2004/037334 A1 | 5/2004 |
| WO | WO 2004/045498 | 6/2004 |
| WO | WO 2004/054632 | 7/2004 |
| WO | WO 2004/091370 | 10/2004 |
| WO | WO 2005/009225 | 2/2005 |
| WO | WO 2005/009488 A2 | 2/2005 |
| WO | WO 2005/016179 A2 | 2/2005 |
| WO | WO 2005/017000 | 2/2005 |
| WO | WO 2005/018695 | 3/2005 |
| WO | WO 2005/025447 | 3/2005 |
| WO | WO 2005/025666 | 3/2005 |
| WO | WO 2005/025666 A2 | 3/2005 |
| WO | WO 2005/034875 | 4/2005 |
| WO | WO 2005/046760 | 5/2005 |
| WO | WO 2005/046761 A1 | 5/2005 |
| WO | WO 2005/046762 | 5/2005 |
| WO | WO 05/051461 | 6/2005 |
| WO | WO 05/070480 | 8/2005 |
| WO | WO 05/082435 | 9/2005 |
| WO | WO 2005/105174 | 11/2005 |
| WO | WO 2005/105175 | 11/2005 |
| WO | WO 2005/105176 | 11/2005 |
| WO | WO 2005/105180 A1 | 11/2005 |
| WO | WO 2005/115497 | 12/2005 |
| WO | WO 2005/123170 | 12/2005 |
| WO | WO 2005/123170 A1 | 12/2005 |
| WO | WO 2006/014764 | 2/2006 |
| WO | WO 2006/048246 A1 | 5/2006 |
| WO | WO 2006/052745 A2 | 5/2006 |
| WO | WO 2006/052839 | 5/2006 |
| WO | WO 2006/056294 A1 | 6/2006 |
| WO | WO 2006/081403 A1 | 8/2006 |
| WO | WO 2006/116992 A1 | 11/2006 |
| WO | WO 2006/130594 | 12/2006 |
| WO | WO 2006/135934 | 12/2006 |
| WO | WO 2007/002835 A2 | 1/2007 |
| WO | WO 2007/013064 A1 | 2/2007 |
| WO | WO 2007/019038 A2 | 2/2007 |
| WO | WO 2007/024230 A1 | 3/2007 |
| WO | WO 2007/030598 A2 | 3/2007 |
| WO | WO 2007/030599 | 3/2007 |
| WO | WO 2007/030601 A2 | 3/2007 |
| WO | WO 2007/075379 | 7/2007 |
| WO | WO 2007/084792 A2 | 7/2007 |
| WO | WO 2007/085396 A1 | 8/2007 |
| WO | WO 2007/106592 A2 | 9/2007 |
| WO | WO 2007/133618 A2 | 11/2007 |
| WO | WO 2008/010094 | 1/2008 |
| WO | WO 2008/013896 A2 | 1/2008 |
| WO | WO 2008/014358 | 1/2008 |
| WO | WO 2008/027449 A2 | 3/2008 |
| WO | WO 2008/030872 | 3/2008 |
| WO | WO 2008/036360 | 3/2008 |
| WO | WO 2008/039839 | 4/2008 |
| WO | WO 2008/040020 A2 | 4/2008 |
| WO | WO 2008/040681 | 4/2008 |
| WO | WO 2008/041926 A1 | 4/2008 |
| WO | WO 2008/064503 | 6/2008 |
| WO | WO 2008/086397 | 7/2008 |
| WO | WO 2008/100437 A1 | 8/2008 |
| WO | WO 2008/100440 A1 | 8/2008 |
| WO | WO 2008/104609 | 9/2008 |
| WO | WO 2008/112304 A1 | 9/2008 |
| WO | WO 2008/131896 | 11/2008 |
| WO | WO 2009/011856 | 1/2009 |
| WO | WO 2009/019227 A2 | 2/2009 |
| WO | WO 2009/019229 A2 | 2/2009 |
| WO | WO 2009/019415 | 2/2009 |
| WO | WO 2009/019496 | 2/2009 |
| WO | WO 2009/021523 | 2/2009 |
| WO | WO 2009/047524 A2 | 4/2009 |
| WO | WO 2009/062327 A1 | 5/2009 |
| WO | WO 2009/066104 A1 | 5/2009 |
| WO | WO 2009/066105 | 5/2009 |
| WO | WO 2009/066105 A1 | 5/2009 |
| WO | WO 2009/066106 | 5/2009 |

(56) References Cited

FOREIGN PATENT DOCUMENTS

| | | |
|---|---|---|
| WO | WO 2009/066106 A1 | 5/2009 |
| WO | WO 2009/070905 | 6/2009 |
| WO | WO 2009/089390 A2 | 7/2009 |
| WO | WO 2009/103031 A1 | 8/2009 |
| WO | WO 2009/111657 A2 | 9/2009 |
| WO | WO 2009/117635 A1 | 9/2009 |
| WO | WO 2009/122989 A1 | 10/2009 |
| WO | WO 2009/124100 | 10/2009 |
| WO | WO 2009/124125 | 10/2009 |
| WO | WO 2009/126102 A1 | 10/2009 |
| WO | WO 2009/126103 A1 | 10/2009 |
| WO | WO 2009/126833 A3 | 10/2009 |
| WO | WO 2009/146441 A1 | 12/2009 |
| WO | WO 2009/151380 A1 | 12/2009 |
| WO | WO 2009/156709 A1 | 12/2009 |
| WO | WO 2009/158124 A1 | 12/2009 |
| WO | WO 2009/158127 A1 | 12/2009 |
| WO | WO 2009/158128 | 12/2009 |
| WO | WO 2009/158130 A1 | 12/2009 |
| WO | WO 2009/158131 | 12/2009 |
| WO | WO 2010/016791 | 2/2010 |
| WO | WO 2010/026251 A1 | 3/2010 |
| WO | WO 2010/033271 | 3/2010 |
| WO | WO 2010/033574 | 3/2010 |
| WO | WO 2010/033613 | 3/2010 |
| WO | WO 2010/035017 A1 | 4/2010 |
| WO | WO 2010/051068 | 5/2010 |
| WO | WO 2010/051073 | 5/2010 |
| WO | WO 2010/051418 A2 | 5/2010 |
| WO | WO 2010/059849 A2 | 5/2010 |
| WO | WO 2010/072309 A1 | 7/2010 |
| WO | WO 2010/072395 A1 | 7/2010 |
| WO | WO 2010/120776 A1 | 10/2010 |
| WO | WO 2010/141271 A1 | 12/2010 |
| WO | WO 2010/142959 | 12/2010 |
| WO | WO 2010/147533 A1 | 12/2010 |
| WO | WO 2010/147592 A1 | 12/2010 |
| WO | WO 2011/019476 A1 | 2/2011 |
| WO | WO 2011/023275 A1 | 3/2011 |
| WO | WO 2012/001371 | 1/2012 |
| WO | WO 2012/022484 A1 | 2/2012 |
| WO | WO 2012/069793 | 5/2012 |
| WO | WO 2012/069794 | 5/2012 |
| WO | WO 2012/151359 | 11/2012 |
| WO | WO 2013/123005 | 8/2013 |
| WO | WO 2013/123022 | 8/2013 |
| WO | WO 2014/184366 | 11/2014 |

OTHER PUBLICATIONS

US 6,306,115, 10/2001, Kelly et al. (withdrawn)
Argenta, Louis C., et al., "Vacuum-Assisted Closure: A New Method for Wound Control and Treatment; Clinical Experience", Ann Plas Surg 1997;38:563-577 (Dec. 10, 1996).
Chintamani, et al., "Half versus full vacuum suction drainage after modified radical mastectomy for breast cancer—a prospective randomized clinical trial", Research Article (Jan. 27, 2005), 1-5.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
De Lange, M.Y. , et al., "Vacuum-Assisted Closure: Indications and Clinical Experience", Eur J Plast Surg (2000) 2;178-182 (Feb. 9, 2000).
Health Technology, Literature R., "Vacuum Assisted Closure Therapy for Wound Care", Health Technology Literature Review (Dec. 2004), 3-59.
International Search Report of International Application No. PCT/US2007/011278 consisting of 6 pages, dated May 11, 2006.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
PCT International Search Report of PCT/US2007/011321, International Filing Date May 10, 2007.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005),185-194.
U.S. Appl. No. 12/832,031, filed Jul. 7, 2010 (published as 2010/0274207 A1) and its ongoing prosecution history, including without limitation Office Actions, Amendments, Remarks, and any other potentially relevant documents.
U.S. Appl. No. 12/744,277, filed Sep. 20, 2010, including its ongoing prosecution history, including without limitation Office Actions, Amendments, Remarks, and any other potentially relevant documents.
U.S. Appl. No. 12/744,218, filed May 21, 2010, including its ongoing prosecution history, including without limitation Office Actions, Amendments, Remarks, and any other potentially relevant documents.
U.S. Appl. No. 12/940,788, filed November 5, 2010, and its ongoing prosecution history including without limitation Office Actions, Amendments, Remarks, and any other potentially relevant documents.
U.S. Appl. No. 12/744,055, filed May 20, 2010, including its ongoing prosecution history, including without limitation Office Actions, Amendments, Remarks, and any other potentially relevant documents.
U.S. Appl. No. 13/092,042, filed Apr. 21, 2011, including its ongoing prosecution history, including without limitation Office Actions, Amendments (including Preliminary Communication filed Nov. 8, 2010), Remarks, and any other potentially relevant documents.
U.S. Appl. No. 13/212,039, filed Aug. 17, 2011, including its ongoing prosecution history, including without limitation Office Actions, Amendments, Remarks, and any other potentially relevant documents.
U.S. Appl. No. 13/217,074, filed Aug. 24, 2011 and its ongoing prosecution history, including without limitation Office Actions, Amendments, Remarks, and any other potentially relevant documents.
U.S. Appl. No. 13/302,980, filed Nov. 22, 2011 and its ongoing prosecution history, including without limitation Office Actions, Amendments, Remarks, and any other potentially relevant documents.
U.S. Appl. No. 13/302,175, filed Nov. 22, 2011 and its ongoing prosecution history, including without limitation Office Actions, Amendments, Remarks, and any other potentially relevant documents.
U.S. Appl. No. 29/389,782, filed Apr. 15, 2011, Peron.
U.S. Appl. No. 29/389,783, filed Apr. 15, 2011, Peron.
U.S. Appl. No. 13/287,897, filed Nov. 2, 2011, including its ongoing prosecution history, including without limitation Office Actions, Amendments, Remarks, and any other potentially relevant documents, dated Nov. 2, 2011, Adie et al.
U.S. Appl. No. 13/287,959, filed Nov. 2, 2011, , including its ongoing prosecution history, including without limitation Office Actions, Amendments, Remarks, and any other potentially relevant documents, dated Nov. 2, 2011, Allen et al.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.

(56) References Cited

OTHER PUBLICATIONS

Kalypto Medical, NPD 1000 Product Brochure.
Kalypto Medical, NPD 1000 Negative Pressure Wound Care System, Clinician & Patient Instructions for Use.
NURSING75, Wound Suction: Better Drainage with Fewer Problems, Nursing, vol. 5, No. 10, Oct. 1975, pp. 52-55.
Prevena™ Incision Management System, Patient Guide, pp. 1-2, Jan. 2010.
Prevena™ Incision Management System, Clinician Guide, pp. 1-9, Jan. 2010.
Wackenfors, A., et al., Effects of Vacuum-Assisted Closure Therapy on Inguinal Wound Edge Microvascular Blood Flow, *Wound Rep. Reg*, 2004, 12, 600-606.
Webb, New Techniques in Wound Management: Vacuum-Assisted Wound Closure, Journal of the American Academy of Orthopaedic Surgeons, v. 10, No. 5, pp. 303-311, Sep. 2002.
Wound Suction, Nursing, Oct. 1975, USA pp. 52-53.
U.S. Appl. No. 12/848,817, filed Aug. 2, 2010 and its ongoing prosecution history, including without limitation Office Actions, Amendments, Remarks, and any other potentially relevant documents, dated Aug. 2, 2010, Blott et al.
U.S. Appl. No. 12/940,788, filed Nov. 5, 2010 and its ongoing prosecution history, including without limitation Office Actions, Amendments, Remarks, and any other potentially relevant documents, dated Nov. 5, 2010, Blott et al.
U.S. Appl. No. 12/744,055, filed May 20, 2010, including its ongoing prosecution history, including without limitation Office Actions, Amendments, Remarks, and any other potentially relevant documents, dated May 20, 2010, Greener.
U.S. Appl. No. 12/744,277, filed Sep. 20, 2010, including its ongoing prosecution history, including without limitation Office Actions, Amendments, Remarks, and any other potentially relevant documents, dated Sep. 20, 2010, Hartwell.
U.S. Appl. No. 12/938,291, filed Nov. 2, 2010, including its ongoing prosecution history, including without limitation Office Actions, Amendments, Remarks, and any other potentially relevant documents), dated Nov. 2, 2010, Weston.
U.S. Appl. No. 12/719,715, filed Mar. 8, 2010, published as 2005/0261642 A1, including its ongoing prosecution history, including without limitation Office Actions, Amendments, Remarks, and any other potentially relevant documents).
U.S. Appl. No. 11/064,813, filed Feb. 24, 2005, including its ongoing prosecution history, including without limitation Office Actions, Amendments, Remarks, and any other potentially relevant documents.
U.S. Appl. No. 12/719,767, filed Mar. 8, 2010, including its ongoing prosecution history, including without limitation Office Actions, Amendments, Remarks, and any other potentially relevant documents.
U.S. Appl. No. 11/098,265, filed Apr. 4, 2005, including its ongoing prosecution history, including without limitation Office Actions, Amendments, Remarks, and any other potentially relevant documents.
U.S. Appl. No. 12/719,767, filed Mar. 17, 2010, including its ongoing prosecution history, including without limitation Office Actions, Amendments, Remarks, and any other potentially relevant documents.
Achterberg et al., "Hydroactive dressings and serum proteins: an in vitro study," Journal of Wound Care, vol. 5, No. 2, Feb. 1996.
Davidov, Y., "Vacuum therapy in the treatment of purulent lactation mastitis," Vestnik Khirurgii, Sep. 1986, pp. 66-70.
Davidov, Y., "Bacteriological and cytological evaluation of the vacuum therapy of suppurative wounds," Vestnik Khirurgii, Oct. 1988, pp. 48-52.
Solovev et al., "The Method of Treatment of Immature External Fistulas in the Upper Gastrointestinal Tract," USSR Ministry of Health, S.M. Kirov Gorky State Medical Institute, 1987.
Stewart, Joanne, "Next generation products for wound management," http://www.worldwidewounds.com/2003/april/Stewart/Next-Generation-Products.html.
Svedman, P., Irrigation Treatment in Split-Thickness Skin Grafting of Intractable Leg Ulcers, Scand J. Plast. Reconst. Surg., 1985, 19, pp. 211-213.
Swift, et al, Quorum Sensing in *Aeromonas hydrophila* and *Aeromonas salmoncida*: Identification of LuxRl Homologs AhyRl and AsaRl and Their Cognate N-Acylhomoserine Lactone Signal Molecules, J. Bacteriol., 1997, 179(17):5271-5281.
U.S. Appl. No. 12/192,000, filed Aug. 14, 2008, Hartwell et al.
U.S. Appl. No. 29/363,038, filed Jun. 3, 2010, Lattimore et al.
U.S. Appl. No. 12/192,000, filed Apr. 14, 2008, Hartwell et al.
U.S. Appl. No. 60/559,727, filed Apr. 5, 2004, Weston.
U.S. Appl. No. 60/573,655, filed May 21, 2004, Weston.
U.S. Appl. No. 11/491,578, filed Jul. 24, 2006, Weston.
U.S. Appl. No. 11/654,926, filed Jan. 17, 2007, Weston.
U.S. Appl. No. 11/784,021, filed Apr. 5, 2007, Weston.
U.S. Appl. No. 12/402,840, including its ongoing prosecution history, including without limitation Office Actions, Amendments, Remarks, and any other potentially relevant documents filed Mar. 12, 2009, Vitaris et al.
U.S. Appl. No. 12/489,883, including its ongoing prosecution history, including without limitation Office Actions, Amendments, Remarks, and any other potentially relevant documents filed Jun. 23, 2009, Heagle.
U.S. Appl. No. 12/879,715, including its ongoing prosecution history, including without limitation Office Actions, Amendments, Remarks, and any other potentially relevant documents filed Sep. 10, 2010, Patel et al.
U.S. Appl. No. 12/760,610, prosecution history, including without limitation Office Actions, Amendments, Remarks, and any other potentially relevant documents filed Feb. 6, 2013, Buan.
U.S. Appl. No. 13/866,346, including its ongoing prosecution history, including without limitation Office Actions, Amendments, Remarks, and any other potentially relevant documents filed Apr. 19, 2013, Patel et al.
U.S. Appl. No. 13/902,446, prosecution history, including without limitation Office Actions, Amendments, Remarks, and any other potentially relevant documents filed May 24, 2013, Weston.
U.S. Appl. No. 13/912,716, prosecution history, including without limitation Office Actions, Amendments, Remarks, and any other potentially relevant documents filed Jun. 6, 2013, Joshi et al.
Argenta, Louis C., et al., "Vacuum/Assisted Closure: A New Method for Wound Control and Treatment; Clinical Experience", Ann Plas Surg 1997;38:563/577 (Dec. 10, 1996).
Arnljots et al., "Irrigation Treatment in Split/Thickness Skin Grafting of Intractable Leg Ulcers," Scandinavian Journal of Plastic and Reconstructive Surgery, 1985, vol. 19, pp. 211-213.
Chintamani, et al., "Half versus full vacuum suction drainage after modified radical mastectomy for breast cancer/ a prospective randomized clinical trial", Research Article (Jan. 27, 2005), 1/5.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15/17.
De Lange, M.Y. , et al., "Vacuum/Assisted Closure: Indications and Clinical Experience", Eur J Plast Surg (2000) 2;178/182 (Feb. 9, 2000).
Health Technology, Literature R., "Vacuum Assisted Closure Therapy for Wound Care", Health Technology Literature Review (Dec. 2004), 3/59.
International Search Report of International Application No. PCT/NL2004/000565 consisting of 5 pages, dated Jul. 29, 2005.
International Search Report of International Application No. PCT/GB00/01566 consisting of 2 pages, dated Sep. 25, 2000.
International Search Report of International Application No. PCT/GB00/04278 consisting of 2 pages, dated Feb. 22, 2001.
International Search Report of International Application No. PCT/US2007/011278 consisting of 6 pages, dated Dec. 11, 2007.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3/4.

(56) References Cited

OTHER PUBLICATIONS

PCT International Search Report of PCT/US2007/011321, Dec. 11, 2007 in 4 pages.
Pham, C., et al., Vacuum/Assisted Closure for the Management of Wounds: An Accelerated Systematic Review, *Asernip/Accelerated Review of Vacuum Assisted Wound Closure*, Report No. 27, Dec. 2003, 1-52.
Solovev, V.A. "Treatment and Prevention of Suture Failures after Gastric Resection" (Dissertation Abstract) (S.M. Kirov Gorky State Medical Institute, Gorky USSR 1988).
Usupov, Y. N., et al., "Active Wound Drainage", The Kremlin Papers: Perspectives in Wound Care, Russian Journal: Vestnik Khirurgii, BlueSky Publishing, La Costa, California (2004), 8/10.
Venturi, Mark L., "Mechanisms and Clinical Applications of the Vacuum/Assisted Closure (VAC) Device", Am J Clin Dermatol (2005) 693, 185/194; Review Article (2005),185/194.
Wackenfors, A., et al., Effects of Vacuum/Assisted Closure Therapy on Inguinal Wound Edge Microvascular Blood Flow, *Wound Rep. Reg*, 2004, 12, 600-606.
Webb, New Techniques in Wound Management: Vacuum/Assisted Wound Closure, Journal of the American Academy of Orthopaedic Surgeons, v. 10, No. 5, pp. 303/311, Sep. 2002.
Written Opinion of the International Searching Authority of PCT International Search Report of PCT/US2007/011321, International Filing Date May 10, 2007.
Written Opinion of the International Search Report of PCT/US2007/011278 consisting of 7 pages, dated Dec. 11, 2007.
"Hydrocolloids," J. of Wound Care, vol. 1, No. 2, (Jul.-Aug. 1992), pp. 27-30.
Alper, J.C., et al., *An Effective Dressing for a Large, Draining Abdominal wound, RN*, Dec. 1988, 24-25.
Alper, J.C., et al., *Moist Wound Healing under a Vapor Permeable Membrane, Journ. of Amer. Acad. of Derm.*, Mar. 1983, 8(3),347-353.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, Pub Med, Abs. Downloaded from Internet, Apr. 24, 2006.
Barker, D.E., et al., Vacuum Pack Technique of Temporary Abdominal Closure: A 7-Year Experience with 112 Patients, Journ. of Trauma: Injury and Critical Care, Feb. 2000, 4892), 201-207.
Birdsell, D.C., et al., The Theoretically Ideal Donor Site Dressing; Annals of 2 Plastic Surgery, vol. 2, Jun. 1979; Gadgetry, Div. of Plastic Surgery, Foothills, Hospital, Calgarv, Canada, 535-537.
Brock, W.B., et al.: "Temporary closure of open abdominal wounds: the vacuum pack", Am. Surg. Jan. 1995; 61(1)30-5—abstract.
Columbia Electronic Encyclopedia, The: the effect of body temperature on wound healing, (http://encyclopedia2.thefreedictionary.com/body+temperature) (printed Jan. 16, 2009, 3 pages).
Garner et al., "Vacuum-assisted wound closure provides early fascial reapproximation in trauma patients with open abdomens," Am. J. of Surgery 1282 (2001) 630-638.
KCI Licensing, "V.A.C. Abdominal Dressing System Advanced Management of the Open Abdomen," 2004.
Miles, W.E., A Method of Performing Abdominoperineal Excision for Carcinoma of the 341 Rectum and of the Terminal Portion of the Pelvic Colon, The Lancet, Dec. 19, 1908, 1812-1813.
Schein et al., "The 'Sandwich Technique' in the Management of the Open Abdomen," British Journal of Surger, 1986, vol. 73, May, pp. 369-370.
Kendall ULTEC Hydrocolloid Dressing (4"x4"), product ordering page, web page downloaded Jul. 13, 2014.
Protz, Kerstin: English translation of "Modern Wundauflagen unterstutzen Heilungsprozess", Wundversorgung: Indikation and Anwendung, Geriatrie Journal 4/05, pp. 3333-3339.
English Translation of Invalidity Suit by KCI Medizinprodukte GmbH versus Kalypto Medical, Inc., concerning declaration of invalidity of the German part of the European Patent No. 2 021 046 (German application No. 60 2007 021 330.4) dated Mar. 11, 2015 in 38 pages.
Response to Communication of Notice of Opposition dated Mar. 24, 2015 re European Patent No. 2 021 047 in 24 pages.
Auxiliary Requests as filed on Mar. 24, 2015 re European Patent No. 2 021 047 in 45 pages.
Appendix PA1 Hydrokolloide Verbände http:--www.pflegewiki.de-wiki-Hydrokolloide_Verbände dated Jan. 19, 2015 in 3 pages. English translation produced using Google translate on May 26, 2015.
Communication of Notice of Opposition dated Jul. 23, 2014, Opposition of European patent EP 2021047 B1, dated Jul. 16, 2014, on behalf of Sorbion GmbH & Co.KG, and cited publications D1-D25, in 568 pages.
English translation of Opposition of European patent EP 2021047 B1, dated Jul. 16, 2014, on behalf of Sorbion GmbH & Co., in 32 pages.
U.S. Appl. No. 10/599,720, filed Oct. 6, 2006, Blott et al.
U.S. Appl. No. 12/260,962, filed Oct. 29, 2009, Weston.
European Exam Report, re EP Application No. EP 11 154 569.5, dated Nov. 13, 2014.
International Standard ISO 10079-1, First Edition, May 15, 1991, 2 pages.
International Preliminary Report for International Application No. PCT/GB03/04647, Date of Completion Sep. 9, 2004 in 2 pages.
International Search Report in related PCT Application No. PCT/GB03/04647, Date of Completion Feb. 13, 2004 in 3 pages.
"General Characteristics of Wound Healing and Russian Classificaiton of Wound Healing Process,".
"Pleur-evac. Adult-Pediatric, Non-Metered." Code No. A-4000. Control No. F7961J, 1 page.
3M Health Care, Controlling the Risk of Surgical Site Infections after Cardiovascular Procedures: The Importance of Providing a Sterile Surface, *Brochure*, St. Paul, MN and London, Ontario, Canada, 1997, 8 pages.
A Sensational Medical discovery, *Brit. Journ. Nurs.*, Jul. 15, 1911, 42.
Abelson, R., Hospitals See Possible Conflict on Medical Devices for Doctors, *Thurs, Sep. 22, 2005, Newspaper Article*.
Aeros, "Moblvac II," 1 page, Aeros Instruments, Inc., Northbrook, IL Oct. 1988.
Aeros, Aeros Instruments, Inc. 1111 Lakeside Dr., Gurnee, IL 60031. Aug. 1993. "Care-E-Vac," 2 pages.
Aeros, Aeros Insturments, Inc. 3411 Commercial Ave., Northbrook, IL 60062. Oct. 1988. Part No. 1504-02 7M. Instavac Aspirator, 1 page.
Aeros, Care-e-vac II, Downloaded from internet http://www.aerosinstruments.com Apr. 10, 2006.
Aeros, moblvac® III, Downloaded from internet http://www.aerosinstruments.com Apr. 10, 2006.
Agarwala, S., et al., Use of Mini-Vacuum Drains in Small Surgical Wounds, *Plastic and Reconstructive Surgery*, Apr. 1998, 101(5), 1421-1422 (*Correspondence*).
Agrama, H.M., Functional Longevity of Intraperiotoneal Drains, *Amer. Journ. of Surg.*, Sep. 1976, 132, 418-421.
Alexander, J. Wesley, "Prevention of Wound Infections," *The American Journal of Surgery*, Jul. 1976, pp. 59-63, vol. 132, USA.
Alper, Joseph, C., "Recent Advances in Moist Wound Healing," Southern Medical Journal, Nov. 1986, pp. 1398-1404, vol. 79, No. 11 USA.
Article Excerpt, *Lancet*, Jun. 14, 1952, 1175-1176.
Article Excerpt: Part III. Resolving Selected Clinical Dilemmas, 17-20.
Arturson, M. Gosta, *The Pathophysiology of Severe Thermal Injury*, JBCR, 6(2): 129-146 (Mar.- Apr. 1985).
Author Unknown, Oceans of Air, *Measurement Demonstration*, 7 pgs.
Author Unknown, Other References, 3 pgs.
Author Unknown, Possible Prior Art Reference List, 1-31.
Author Unknown, Publication by Russians, 15 pgs.
Author Unknown, References, 234-248.

(56) References Cited

OTHER PUBLICATIONS

Avocat, C. et al., Nouvelle Presentation de Materiel Pour Drainage de Redon et Jost, *La Nouvelle Press Medicale*, Jun. 26, 1976, 5(6), 1644-1645 (in French).
Ayoub, M.H. and G. C. Bennet, A Study of Cutaneous and Intracompartmental Limb Pressures Associated with the Combined Use of Tourniquets and Plaster Casts, Abs., *Proc. and Reports of Univ., Colleges, Councils, Assoc., and Societies*, 68-B:3, May 1986, 497.
Bagautdinov, "Variant of External Vacuum Aspiration in the Treatment of Purulent Diseases of Soft Tissues," Current Problems in Modern Clinical Surgery, 1986, 4 pages.
Baldwin, J.F., Ed., The Columbus Medical Journal, Columbus, Ohio, 1887, V., 561.
Barbul, A., et al., Eds., Clinical and Experimental Approaches to Dermal and Epidermal Repair, Normal and Chronic Wounds, Progress in Clin. and Biol. Res., vol. 365, *Proc. of the 3rd Intnl. Symp. on Tissue Repair*, Miami, FL, Jan. 10-14, 1990, Abs.
Bar-El, Y. et al., Potentially dangerous Negative Intrapleural pressures Generated by Ordinary Pleural Drainage Systems, *Chest*, Feb. 2001, 119(2), 511-514.
Bascom, J., Pilonidal Sinus, *Current Therapy in Colon and Rectal Surgery*, 1990, 1-8.
Benjamin, P.J., Faeculent Peritonitis: A Complication of Vacuum Drainage, *Br. J. Surg.*, 1980, 67, 453-454.
Berman and Fabiano, Closed Suction Drainage, *Orthopedics*, Mar. 1990, 13(3), 310-314.
Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.
Besst, J.A., Wound Healing-Intraoperative Factors, *Nursing Clinics of North America*, Dec. 1979, 14(4), 701-712.
Betancourt, Sergio, "A Method of Collecting the Effluent from Complicated Fistual of the Small Intestine," Dept. of Surgery, Allegheny General Hospital, Pittsburgh, p. 375, USA.
Bischoff, et al., Vacuum-Sealing Fixation of Mesh Grafts, *Euro. Journ. Plast. Surg.*, Jul. 2003, 26(4), 189-190, Abs. Downloaded from internet Apr. 6, 2006.
Bui, T.D., et al., Negative Pressure Wound Therapy with Off-the-Shelf Components, *Amer. Journ. Surg.*, Jan. 16, 2006, 192, 235-237.
Chart: Influence of Wound Closure on Healing of Perineal Wound after Abdominoperineal Resection or Total Proctocolectomy, excerpt faxed Jan. 23, 2006, 1 page.
Chua Patel, C.T., et al., Vacuum-Assisted Closure, *AJN*, Dec. 2000, 100(12), 45-49.
CMS, HCPCS Public Meeting Summary Report for: Durable Medical Equipment (DME), Jun. 23, 2005, 39 pgs.
Costa, V., et al., Vacuum-Assisted Wound Closure Therapy (V.A.C.), Jul. 11, 2005, Centre Universitaire de Sante McGill, McGill University Health Center, 1-24.
Curtin, L.L., Wound Management: care and Cost—an Overview, *Nursing Management*, Feb. 1984, 15(_), 22-25.
Davis, J.C. and T.K. Hunt, Eds., Problem Wounds: The Role of Oxygen, Chap. 1, Infection and Oxygen, 1988, 1-15.
Davydov et al. "Pathogenic Mechanism of the Effect of Vacuum Therapy on the Course of the Wound Process" Dec. 1986.
Deknatel, Div. of Howmedica, Inc. Queens Village, NY 11429. "Pleur-evac.".
Dillon, Angiology, The Journal of Vascular Diseases, pp. 47-55, Jan. 1986, "Treatment of Resistant Venous Statis Ulcers and Dermatitis with the End-Diastolid Pneumatic Compression Boot.".
Doillon, C.J., et al., Collagen-Based Wound Dressings: Control of the Pore Structure and Morphology, Journal of Biomedical Materials Research, Sep. 13, 2004, 20(8), 1219-1228. Abs. Downloaded from Internet http://www3.interscience.wiley.com, Apr. 28, 2006.
Gogolewski, S., et al., Polyurethane Vascular Prosthesis in Pigs, *Colloid & Polymer Science*, Sep. 1987, 265(9), 774-778, abs. Downloaded from internet Mar. 20, 2006.
Gomco Suction Equipment & Accessories Guide, Catalog, Apr. 2006, 20 pages.
Gomco, Gastro-Intestinal Thermotic Drainage Pump 270 NR, eBay Downloaded from internet http://cgi.ebay.com Apr. 7, 2006.
Goverman, J., et al., the "Fistula VAC," a Technique for Management of Enterocutaneous Fistulae Arising within the Open Abdomen: Report of 5 Cases, *Journ. of Trauma Injury, Infection, and Critical Care*, Feb. 2006, 60(2), 428-431.
Grabowski, S., Leczenie ran z zastosowaniem posicśnienia (wg Redona I Josta), *II Klinik Xhieuefxnej Am w Warszawie; klerownik: Prof. Dr. Z. Lapinski*, No. 1, 19-21 (in Polish).
Greene, M. A., et al. Laparotomy Wound Closure with Absorable Polyclycolic Acid Mesh, Surgery, Gynecology and Obsterics Mar. 1993; vol. 176, pp. 213-218.
Gupta, S., Guidelines for Managing: Pressure Ulcers with Negative Pressure Wound Therapy, Downloaded from internet http://proquest.umi.com on Feb. 3, 2006. 19 pages.
Halasev, S., Growing Public, *MX Business Strategies for Medical Technology Executives*, Mar./Apr. 2005.
Hanbok för Hälso-Och Sjukvårdsarbete Lokal Anvisning för Landstinget Sörmland, Jan. 2001, 7 pgs, (in Swedish), Downloaded from Internet http://www.landstinget.sormland.se, Aug. 14, 2001, 7 pages.
Hargens et al., Aviation, Space and Environmental medicine, pp. 934-937, Oct. 1991, "Lower Body Negative Pressure to Provide Load Bearing in Space.".
Harkiss, K., Cheaper in the Long Run, *Community Outlook*, Aug. 1985, 19-22.
Harle, A. Z. Orthop., 127: 513-517 (1989), "Schwachstellen herkommlicher Drainagen."
Harris, "A new technique of skin grafting using Stei-Greffe and a self-adhering foam pad," Brit. J. of Plastic Surg., vol. 34, No. 2, (Apr. 1981), pp. 181-185.
Harvard Pilgrim Health Care, Technology Assessment Policy, TA 6.29 Negative Pressure Wound therapy for Wound Healing, Dec. 2004, 1-6.
HCPCS (CMS) Public Meeting Agenda for Jun. 23, 2005, Durable Medical Equipment (DME), 28pgs.
HCPCS, Applications for Modifications to HCPCS Level II Code Set in the 2005-2006 Coding Cycle, 60 pgs.
Hyperemia by Suction Apparatus, Chapter VIII, 74-85.
Instech Model P720 Peristaltic Pump Operation Manual, Dec. 1997, pp. 1-11.
Jahns et al., Poster "Problemwundversorgung mit einem neuen anschmiegsamen Silikonschaumverband mit Anwendung der Vakuumtechnik," 2nd Congress of German Wound Treatment Society 1998.
KCI Introduces New Vacuum Assisted Closure Product; VAC. Freedom Device Continues Company's Leadership in Advanced Wound Healing Systems, PR Newswire, Oct. 2002.
KCI USA, Inc., Vacuum Therapy Unit, *U.S. Food and Drug Administration*, internet download from database updtd. Apr. 1, 2005.
KCI, Inc., *Annual Report 2004—Changing the Standard of Healing*, 1-113.
KCI, Inc., Press Release, V.A.C. Freedom® System Receives Joint Airworthiness Certification, Dec. 21, 2006, Downloaded from internet, http://biz.yahoo.com/bw/061221/20061221005599.html?v=1.
KCI, Inc., The V.A.C. System, 2000-2001, Brochure, 2 pgs.
Khan, et al., "Influence of Chitosan Molecular Weight on its Physical Properties", EIMJM (2003); 2(1); pp. 1-8.
Khil'kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006.
Kiemele, L.J., et al., Catheter-Based Negative Pressure Wound Therapy: A New Paradigm of Care, *Nursing Home Wound Care consultative Service*, Mayo Clinic, Rochester, MN. 2 pages.
Kockrow, E., Surgical Wound Care, *Surgical Wound Care*, 2006, Chap. 13, 1-32.
Lehrman, "The Not-So-Bald-Truth," Science, Sep. 1992, p. 42.

(56) References Cited

OTHER PUBLICATIONS

Letsou et al. "Stimulation of Adenylate Cyclase Activity in Cultured Endothelial Cells Subjected to Cyclic Stretch." Cardiovascular Surgery 3. Toronto. Sep. 1989, pp. 634-639.
Levine, J.M., Implementing the New CMS Guidelines for Wound Care, Nursing Homes, Apr. 21, 2006, Downloaded from internet, http://www.nursinghomesmagazine.com/Past_Issues.htm?ID=4408.
Maddin et al., International Journal of Dermatology, 29: 446-450 (1990), "The Biological Effects of a Pulsed Electrostatic Field with Specific References to Hair: Electrotrichogenesis.".
Malli, S., Keep a Close Eye on Vacuum-Assisted Wound Closure, *Device Safety, DHHS, CDRH*, May 2005.
Medela Product Information (with English Summary): "Pleupump MK II is the new micro-data controlled thoracic drainage," 12 pages.
Medela, Inc., Medela Obstetrical Vacuum Delivery System, *510(k) Summary K041579*, Apr. 21, 2005, Correspondence.
Medela, Inc., Medela to Increase Presence in Wound Care Market, *Press Release*, Chicago, IL, Aug. 29, 2006.
Medela, Inc., Pleupump MK II, Aug. 14, 2001, Brochure (in German). 12 pages.
Medela, Manualectric Breastpump, *Catalog*, 4 pgs.
Medtronic, Octopus System, Catalog, 3 pgs.
Membrane Filters, in 16 pages, from website: http://www.advantecmfs.com/catalog/filt/membrane.pdf#page=11 (date unknown, but believed to be copyright 2001-2011).
Meyer and Schmieden, *Bier's Hyperemic Treatment*, 1908, Fig. 69-70, 557.
Meyer, W. & Schmieden, V., *Bier's Hyperemic Treatment*, W B. Saunders Company 1908, (the entire reference has been submitted, but pp. 44-65 may be the most relevant).
Meyer, Weight-Loaded Syringes as a Simple and Cheap Alternative to Pumps for Vacuum-Enhanced Wound Healing, *Plastic and Reconstructive Surg., Jun. 2005, 2174-2176 (Correspondence)*.
Microtek Heritage, Inc. P.O. Box 2487, Columbus, MS 39704, "Wound-Evac ET," 4 pages.
Miles, W. Ernest, "Technique of the Radical Operation for Cancer of the Rectum", The British Journal of Surgery,pp. 292-304, United Kingdom 1914-1915.
Miller, M.S., et al., Negative Pressure Wound Therapy: An Option for Hard-to-Heal Wounds, *focuson Wound care*, Jan. 2006, 57-61.
Miller, M.S., et al., Treating a Postoperative, Ischemic Foot Wound Using Bovine Dermal-Derived Extra-Cellular Matrix PRIMATRIX™ with the BlueSky Medical Versatile 1™ Negative Pressure Wound Therapy System, *The Wound Healing Center*, Terre Haute, Indiana, Case Study 2005.
Miller, M.S., et al., Treating an Wagner Grade 3 Diabetic Foot Ulcer using BlueSky Medical Versatile 1™ Negative Pressure Wound Therapy System and the Miller DermiVex™ Drain, *The Wound Healing Center*, Terre Haute, Indiana, Case Study 2005.
Miller, M.S., Negative Pressure Wound Therapy: "A Rose by Any Other Name," *Ostomy/Wound Management*, Mar. 2005, 51(3), 44-49.
Mitchell, Richard N., et al.: "Role of Stem Cells in Tissue Homeostasis", Pocket Companion to Robbins and Cotran Pathologic Basis of Diseas, 7th Ed., 2006.
Mokhtari, A., et al., Sternal Stability at Different negative Pressure during Vacuum-Assisted Closure Therapy, *Soc. of Thoracic Surgeons*, 2006, 82, 1063-1067.
Morykwas, M. J., et al., "Vacuum-Assisted Closure: A New Method for Wound Control and Treatment: Animal Studies and Basic Foundation," *Annals of Plastic Surgery* 38 (1997) 553-562, Dec. 10, 1996.
Morykwas, M. J., et al.: "Nonsurgical Modalities to Enhance Healing and Care of Soft Tissue Wounds", Journal of the Southern Orthopaedic Association, vol. 6, No. 4 Winter 1997 in 12 pages.
Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.
Noblett, E.A., What is an Empyema? What Operations are Undertaken for its Relief, and What Have You to Say About the After-Nursing?, *Brit. Journ. Nurs.*, Apr. 29, 1916, 375.
Norton, S.E., et al., Vacuum-Assisted Closure (VAC Therapy) and the Risk of Fluid Loss in Acute Trauma, *Ann. of Plast. Surg.*, Feb. 2006, 56(2), 194-195.
Ontario, Vacuum Assisted Closure Therapy for Wound Care, Dec. 2004, Toronto, ON, Canada, 1-59.
Orgill, D.P., et al., Guidelines for Treatment of Complex Chest Wounds with Negative Pressure Wound Therapy, Wounds, A Compendium of Clinical Research and Practice, Suppl. B, Dec. 2004, 1-23.
Paradise Valley Hospital, The Center for Wound Healing and Hyperbaric Medicine, *Brochure*. 3 pgs.
Paradise Vally Hospital, Healthy Living, *Newsletter*, Fall 2001, 7 pgs.
Penman, M., What Are the Signs and Symptoms of Gallstones? What Instruments Would You have Ready for the Operation? How Would You Nurse a Case After Operation?, *Brit. Journ. Nurs.*, Aug. 9, 1919, 88.
Precision Medical, Easy Go VAC Aspirator, http://presicionmedical.com website Downloaded from internet Apr. 10, 2006.
Precision Medical, Power VAC+ Intermittent Aspirator, http://precisionmedical.com Downloaded from internet Apr. 10, 2006, 2 pages.
Press Release for BlueSky by McClanahan and Clearman, LLP, Judge Enters Judgment Upholding BlueSky Medical Verdict in Wound-Care Patent Battle, San Antonio PR/Newswire, Downloaded from Internet Aug. 30, 2006.
Press Release, BlueSky Medical Group, Inc., BlueSky Leads Fire Victim Releif Effort in San Diego Area, http://blueskymedical.com, Mar. 31, 2006.
Press Release, BlueSky Medical Group, Inc., BlueSky Wins Key Jury Verdict. Aug. 3, 2006.
Press Release, BlueSky Medical Group, Inc., Department of HHS to Review Reimbursement in NPWT Area, http://blueskymedical.com, Mar. 29, 2006.
Press Release, BlueSky Medical Group, Inc., European Patent Office to Rule on KCI Patent, Downloaded from internet, http://blueskymedical.com, Mar. 29, 2006.
Press Release, BlueSky Medical Group, Inc., Request for Decrease in Reimbursement for NPWT, http://blueskymedical.com, Mar. 30, 2006.
Press Release, BlueSky Medical Group, Inc., Request for Investigation in Potential Unfair Trade Practices, Downloaded from internet, http://blueskymedical.com, Mar. 30, 2006.
Reference Handbook of the Medical Sciences, *Hyperaemia*, 553.
Reid, Daniel P., Information on Cupping or Using Suction Cups on Wounds and for Healing Purposes, *Chinese Herbal Medicine*, 2 pages.
Renner, R., et al., Vacuum Therapy in dermatology: A Review. *JDDG*, 2006, 4, 468-476.
Rodrigo, J.J., et al., The Effect of Varying Degrees of Suction Pressure on Drainage of Hematomas, *Dept. of Orthopaedic Surgery, University of California, David, Sacramento, California*, 9 pages (date N/A).
Sandahl, L., Slides at Geisinger Medical Center, Danville, PA, Apr. 10, 1990, Correspondence, 4 pages.
Sartipy, U. et al., Cardiac Rupture During Vacuum-Assisted Closure Therapy, *Ann. Thorac. Surg.* 2006, 82, 1110-1111.
Scott, F., Babies in Bottles, *Advance for Resp. Care Practitioners*, Nov. 23, 1992, 2 pgs.
Spahn, Slide presented at the WOCN meeting in Ontario, California, Sep. 2001.
Sparta Instrument Corp. 26602 Corporate Ave., Hayward, CA 94545, Power Source Multi-Purpose Surgical Aspirator, 1 page.
Specific Inflammations, Diseases of the Skin, 549-550.
Techno Takatsuki Co., Ltd., 8-16 Hatchonishimachi, Takatsuki City, Osaka, Japan, "HiBlow Air Pump.".

(56) References Cited

OTHER PUBLICATIONS

Unknown, "The RN Magazine/University of California Continuing Education Curriculum; Examination on 'To heal a draining wound'", RN, Mar. 1982, p. 36, USA.

Unknown, Medela product information with English Summary: "Pleupump MK II is the new micro-data controlled thoracic drainage".

US Medco Healthcare, Healing through Technology, HYPOwound Therapy System, from website http://www.usmedco.net Downloaded from internet Apr. 18, 2006.

Warren, J.C. and A.P. Gould, Ed., The International Text-Book of Surgery, 1902, 1, 70-79.

European, Supplemental Search Report, EPO App. No. EP 05 75 0239, dated Apr. 23, 2010 in 3 pages.

International Preliminary Report, International Application No. PCT/US2005/17225, dated Jul. 31, 2006, in 6 pages.

International Search Report, International Application No. PCT/US2005/17225, dated Oct. 4, 2005, in 1 page.

International Written Opinion, International Application No. PCT/US2005/17225, dated Oct. 4, 2005, in 4 pages.

Assessing the Patient with a Fistula or Draining Wounds, Nursing, Jun. 1980, 49-51.

Aubrey, D.A., et al., Treatment of the Perineal Wound after Proctectomy by Intermittent Irrigation, Arch. Surg., Oct. 1984, 119, 1141-1144.

Bagautdinov, N.A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.

Biblehimer, Helen L., "Dealing With a Wound that Drains 1.5 Liters a Day," RN, Aug. 1986, pp. 21-23, USA.

Bier, A., Hyperemia as a Therapeutic Agent, Ed. Dr. Gustavus M. Blech, A. Robertson & Co., Chicago 1905, (the entire reference has been submitted, but pp. 74-85 may be the most relevant).

Bonnema, J., et al., A Prospective Randomized Trial of High Versus Low Vacuum Drainage after Axillary Dissection for Breast Cancer, Amer. Journ. Surg., Feb. 1997, 173, 76-79.

Boretos, John W., "Cellular Polymers for Medical Use: The Vital Role of Porosity and Permeability," Cellular Polymers, 1984, vol. 3, pp. 345-358.

Britton, B.J., et al., A Comparison Between Disposable and Non-Disposable Suction Drainage Units: A Report of a Controlled Trial, Br. J. Surg. 1979, 66, 279-280.

Broader, J.H., et al., Management of the Pelvic Space after Proctectomy, Br. J. Surg., 1974, 62, 94-97.

Brubacher, Lynda L., "To Heal a Draining Wound", RN, Mar. 1982, pp. 30-35, USA.

Brummelkamp, W.H., et al, "High-vacuum drainage and primary perineal wound closure in abdominoperineal excision of the rectum", The Netherlands Journal of Surgery, 1991 pp. 236-238, Netherlands.

Bruno, P., The Nature of Wound Healing: Implications for Nursing Practice, Nursing Clinics of North American, Dec. 1979, 14(4), 667-682.

Bucalo et al. "Inhibition of Cell Proliferation by Chronic Wound Fluid." Wound Repair and Regeneration. Miami, 1993. pp. 181-186.

Burdette-Taylor, S.R., Use of the Versatile One (V1) for Closed Suction Drainage to Stimulate Closure in Chronic Wounds in Home Care, Case Study Presentation, 2003, 2 pgs.

Bush, G.K., What is a Counter Irritant? Name Any That You Know and the Method of their Application, Brit. Journ. Nurs., Oct. 1927, 232.

Calhoun, P. and K. Kenney, Pouching Management of Patients with Open abdomen, Eviscerations and Bowel Fistulas, Case Studies, Univ. of Miami/Jackson Memorial Medical Center, 1 page.

Campbell, P.E., Surgical Wound Case Studies with the versatile 1 Wound Vacuum System for Negative Pressure Wound Therapy, J. WOCN, Mar./Apr. 2006, 33, 176-190.

Campbell, P.E., Think negative, Advances for Providers of Post-Acute Care, Sep./Oct. 2005, 1 page.

Candiani, P., et al., Repair of a Recurrent Urethrovaginal Fistula with an Island Bulbocavernous Musculocutaneous Flap, Plastic and Reconstructive Surgery, Dec. 1993, 1393-1394.

Carroll, P.L., The Principles of Vacuum and its Use in the Hospital Environment, 2nd Ed., 1986, 30p.

Chardak et al., "Experimental Studies on Synthetic Substitutes for Skin and Their Use in the Treatment of Burns," Annals of Surgery, 1962, vol. 155, No. 1, pp. 127-139.

Chariker, M.E., et al, "Effective Management of Incisional and Cutaneous Fistulae with Closed Suction Wound Drainage," Contemporary Surgery. Jun. 1989, pp. 59-63, vol. 34 USA.

Clark, R.A.F. et al., The Molecular and Cellular Biology of Wound Repair, Chapter 1 (1988).

Cobb, J.P., Why Use Drains?, Br. J. Bone Joint Surg., Nov. 1990, 72-B(6), 993-995.

Comfortrac, ComforTrac Defeats the Saunders Group, Keysville, VA, MEDICA,, Nov. 2006, Brochure.

Cooper, D.M., Optimizing Wound Healing, Nursing Clinics of North America, Mar. 1990, 25(1), 163-179.

Cooper, D.M., Postsurgical Nursing Intervention as an Adjunct to Wound Healing, Nursing Clinics of North America, Dec. 1979, 14(4), 713-726.

Cooper, S.M. and E. Young, Topical Negative Pressure, Commentary, I nternational Journal of Dermatology 2000, 39, 892-898.

Costunchenok, B.M., et al., Effect of Vacuum on Surgical Purulent Wounds, Vestnik Chirurgia 1986, Sep. 18-20 (in Russian with English translation).

Cotton, P.B., et al., Early Endoscopy of Oesophagus, Stomach, and Duodenal Bulb in patients with Haematemesis and Melaena, Br. Med. Journ., Jun. 1973, 2, 505-509.

Creative Medical Laboratories, Instruction Manual, Inc. P.O. Box 6347, Rochester, Minn. 55903. "TUGS" (Transportable Universal Gradient Suction), 8 pages.

Crisp, W.J. and A. Gunn, Granuflex Dressings for Closed Surgical Wounds Combined with Suction Drainage, Annals of the Royal College of Surgeons of England, 1990, 72, p. 76.

Cucuroos, Y.C., Vacuum Drainage of Post Operative Wounds, Kiev Army Hospital, Dept. of Hospital Surgery, Kiev medical University, 64-65 (in Russian with English translation).

Davydov et al. "Pathogenic Mechanism of the Effect of Vacuum Therapy on the Course of the Wound Process" pp. 42-47 (Dec. 1990).

Davydov, Y.A., et al. Justifying the Usage of Force Early Secondary Sutures in treatment of Purulent Wounds by the Vacuum Therapy, Vestnik Chirurgia 1990, March Edition, 126-129 (in Russian with English translation).

Davydov, Y.A., et al., Concept of Clinico-Biological Management of Wound Process in Treatment of Purulent Wounds with the Help of Vacuum Therapy, Vestnik Chirurgia 1991, February Edition, 132-135 (in Russian with English translation).

Dilmaghani et al., "A Method for Closed Irrigation and Suction Therapy in Deep Wound Infections," Journal of Bone and Joint Surgery, 1969, vol. 51-A, No. 2, pp. 323-342.

Domkowski, P.W., et al., Evaluation of Vacuum-Assisted Closure in the Treatment of Poststernotomy Mediastinitis, Journ. of Thorac. and Cardiovascular Surg., Aug. 2003, 126(2), 386-390.

Doss, Mirko, et al., Vacuum-Assisted Suction Drainage Versus Conventional Treatment in the Management of Poststernotomy Osteomyelitis, Euro. Journ. Cardio-Thoracic. Surg. 22 ((2002) 934-938.

Draper, J., Make the Dressing Fit the Wound, Nursing Times, Oct. 9, 1985, 32-35.

Dunbar, A., et al., Silicone Net dressing as an Adjunct with Negative Pressure Wound Therapy, Ostomy/Wound Management, Nov. 2005, 51(1A Suppl.), 21-22.

Dunbar, J.M., State What You Have Learned Recently on the Up-to-Date Care of Wounds, Brit. Journ. Nurs., Dec. 1941, 200.

Dunlop, M.G, et al. Vacuum Drainage of Groin Wounds after Vascular Surgery: A Controled Trial, Br. J. Surg., May 1990, 77, 562-563.

(56) References Cited

OTHER PUBLICATIONS

Eaglstein, W.H., et al., Wound Dressings: Current and Future, *Clin. and Exper. Approaches to Dermal and Epidermal Repair: Normal and Chronic Wounds*, 1991, 257-265.

ECRI, Target Report, Negative Pressure Wound Therapy for Chronic Wounds, Jan. 24, 2006, 1-7, Downloaded from internet, http://www.target.ecri.org/summary/detail.aspx?dox_id=1155.

Eisenbud, D.E., Modern Wound Management, *Anadem Publishing*, Chap. 16, 109-116, 2000.

Ellingwood, F., Ellingwood's Therapeutist, Jun. 14, 1908, 2(6), 32-33.

Elwood, E.T., and D.G. Bolitho, Negative-Pressure Dressings in the Treatment of Hidradenitis Suppurative, *Annals of Plastic Surgery*, Jan. 2001, 46(1), 49-51.

Emerson, Series 55, J.H. Emerson Co., 22 Cottage Park Ave., Cambridge, MA 02140. "Emerson Post-Operative Suction Pumps," 1 page.

Engdahl, O. and J. Boe, Quantification of Aspirated Air Volume reduces Treatment Time in Pneumothorax, *Eur. Respir, J.*, 1990, 3, 649-652.

Engdahl, O., et al., Treatment of Pneumothorax: Application of a Technique which Quantifies Air Flow Through the Chest Drain, *Adv. in Therapy*, May/Jun. 1988, 5(3), 47-54.

Erichsen, J.E., Science and Art of Surgery, *London: Longmans, Green, and Co.*, 1895, vol. 1, 258-259, and p. 289.

Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.

Falanga, Vincent, "Growth Factors and Chronic Wounds: The need to Understand the Microenvironment." Journal of Dermatology, vol. 19: 667-672, 1992.

Fay, M.F., Drainage Systems: Their Role in Wound Healing, *AORN Journal*, Sep. 1987, 46(3), 442-455.

Fellin, R., Managing Decubitus Ulcers, *Nursing Management*, Feb. 1984, 29-30.

Fingerhut, A., et al., Passive vs. Closed Suction drainage after Perineal Wound Closure Following Abdominoperineal Rectal Excision for Carcinoma, *Dis Colon Rectum*, Sep. 1995, 926-932.

Finley, John M.,"Practical Wound Management," pp. 45, 127, 143, 149, 207, 1981.

Firlit, C.F. and J.R. Canning, Surgical Wound Drainage: A Simple Device for Collection, *Journ. of Urology*, Aug. 1972, 108, p. 327.

Fisher, Jack, and R. W. Bert, Jr., A Technique for Skin Grafting Around Abdominal Wall Fistulas, *Annals of Plastic Surgery*, 11:6, Dec. 1983, 563-564.

Flanagan, et al., Optional Sump: Novel Use of Triple Lumen Closed Drainage System, *Anz. J. Surg.*, Nov. 2002, 72(11), 806-807, Abs. Downloaded from internet Nov. 30, 2003.

Fleck, C.A., When Negative is Positive: A Review of Negative Pressure Wound therapy, *Wound Care*, Mar./Apr. 2004, 20-25.

Fleischmann, "Vacuum sealing: indication, technique, and results," *European Journal of Orthopaedic Surgery & Traumatology*, vol. 5(1), 1995, pp. 37-40.

Fleischmann, W. Acta Orthopaedical Belgica, "Treatment of Bone and Soft Tissue Defects in Infected Nonunion," vol. 58, *Suppl. 1-1992*, pp. 227-235.

Fleischmann, W. Unfall Chirurg, Springer-Variag, "Vakuumversiegelung zur Behandlung des Weichteilschadens bei offenen Frakturen," (English abstract, no English translation), 1993, pp. 488-492.

Fleischmann, W. Wund Forum Spezial, "Vakuumversiegelung zur Behandlung von Problemwunden" (with English translation: Vacuum Sealing for Treatment of Problematical Wounds), *IHW '94*, 6 pages.

Flynn, M.E. and D.T. Rovee, Wound Healing Mechanisms, *Amer. Journ. of Nursing*, Oct. 1982, 1544-1556.

Fox, J.W. and G.T. Golden, The Use of Drains in Subcutaneous Surgical Procedures, *Amer. Journ. of Surg*, Nov. 1976, 132, 673-674.

Garcia-Rinaldi, R., et al., Improving the Efficiency of Wound Drainage Catheters, *Amer. Journ. of Surg.*, Sep. 1975, 130, 372-373.

Geiger Jones, E., et al., Management of an Iliostomy and Mucous Fistula Located in a Dehisced Wound in a Patient with Morbid Obesity, *J. WOCN*, Nov. 2003, 30(6), 351-356.

Gill, P., What is a Counter-Irritant? Name Three and the Method of Applying them, *Brit. Journ. Nurs.*, Jun. 1934, 142.

Goddard, L., Inflammation: Its Cause and Treatment, *Brit. Journ. Nurs.*, Jan. 1944, 2.

Gogia, Prem P., "The Biology of Wound Healing." Ostomy/ Wound Management. Nov.-Dec. 1992, pp. 12-20.

Gouttefangeas, C. et al., Functional T Lymphocytes Infiltrate Implanted Polyvinyl Alcohol Foams During Surgical Wound Closure Therapy, *Clin. Exp. Immunol.* 2001, 124, 398-405.

Grishdevich, V. and N. Ostrovsky, Postburn Facial Resurfacing with a Split Ascending Neck Flap, *Plastic and Reconstructive Surgery*, Dec. 1993, 1384-1391.

Grobmyer, et al., High-Pressure Gradients Generated by Closed-Suction Surgical Drainage Systems, *Surg. Infect. (Larchmt)*, Autumn 2002, 3(3), 245-249, Abs., Downloaded Nov. 30, 2003.

Grover, R. and R. Sanders, Recent Advances: Plastic Surgery, Clinical Review, *BMJ*, Aug. 8, 1998, 317, 397-400.

Gupta, S., Ed., Guidelines for Managing pressure Ulcers with Negative Pressure Wound Therapy, *Advances in Skin & Wound Care Suppl.*, Nov./Dec. 2004, 17(2), 1-16.

Gwan-Nulla, D.N. and R.S. Casal, Toxic Shock Syndrome Associated with the Use of the Vacuum-Assisted Closure Device, *Ann. Plast. Surg.*, Nov. 2001, 47(5), 552-554.

Hallstrom, B.R. and J.F. Steele, Postoperative Course after Total Hip Arthroplasty: Wound Drainage versus No Drainage, Orthopaedic Review, Jul. 1992, 847-851.

Hartz, R.S., et al., Healing of the Perineal Wound, *Arch. Surg.*, Apr. 1980, 115, 471-474.

Hay, J., et al., Management of the Pelvic Space With or Without Omentoplasty after Abdominoperineal Resection for Carcinoma of the Rectum: a Prospective Multicenter Study, *Eur. J. Surg*, 1997, Abs.

Hays, K., Online Casket Seller Provides an Alternative, *San Antonio Express-News*, Sunday, Feb. 13, 2005, Sec. 1.

Higgins, S., The Effectiveness of Vacuum Assisted Closure (VAC) in Wound Healing, *Centre for Clinical Effectiveness, Monash Medical Centre, Clayton VIC Australia*, Dec. 2003, 1-16.

Hilsabeck, J.R., The Presacral Space as a Collector of Fluid Accumulations Following Rectal Anastomosis: Tolerance of Rectal Anastomosis to Closed Suction Pelvic Drainage, Amer. Soc. of Colon and Rectal Surgeons, vol. 25, No. 7, Oct. 1982.

Hilton, P. Surgical Wound Drainage: A Survey of Practices among Gynaecologists in the British Isles, *Br. Journ. of Obstetrics and Gynaecology*, Oct. 1988, 95, 1063-1069.

Hollis, H.W. and M.R. Troy, A Practical Approach to Wound care in patients with Complex Enterocutaneous Fistulas, *Surg., Gyn. & Obs.*, Aug. 1985, 161, 179-181.

Hugh, T.B., Abdominal Wound Drainage, *Med. Journ. of Australia*, May 4, 1987, 146, p. 505 (Correspondence).

Hulten, L. et al., Primary Closure of Perineal Wound after Proctocolectomy or Rectal Excision, *Acta Chir. Scand.*, 1971, 137, 467-469.

Hunt, T.K. and J.E. Dunphy, Eds., Fundamentals of Wound Management, *Appleton-Century-Crofts/New York*, 416-447, 1979.

Ilizarov, G.A., The Tension-Stress Effect on the Genesis and Growth of Tissues: Part II., *Clinical Orthopaedics and Related Research*, Feb. 1989, 239, 263-283.

Izmailov, S.G., et al., Device for Treatment of wounds and Abdominal Cavity, Contents, Surg. No. 8 1997, Downloaded from internet http://www.mediasphera.ru/surgery/97/8/e8-97ref.htm.

Izmailov, S.G., The Treatment of Eventrations with a Special Apparatus, Abstracts, Surg. No. 1 1997, Downloaded from internet, http://www.mediasphera.ru/surgery/97/1/el-97ref.htm.

Jeter, K., Closed Suction Wound Drainage System, *J. WOCN*, Mar./Apr. 2004, 51 (correspondence).

Jeter, Katherine F. ET, Managing Draining Wounds and Fistulae: New and Established Methods, Chronic Wound Care, Chapter 27, pp. 240-246, 1990.

(56) References Cited

OTHER PUBLICATIONS

Johnson, F.E., An Improved Technique for Skin Graft Placement using a Suction Drain, *Surgery, Gynecology & Obstetrics*, Dec. 1984, 159(6), 584-585.
Kazan Medical Institute Doctors, A Gadget to Bring the Wound Edges Close, 78-79 (in Russian with English translation). Aug. 20, 1985.
KCI, Inc., If It's Not V.A.C. Therapy, It's Not Negative Pressure Wound Therapy, *KCI Brochure*, Jan. 2005, 1-5.
KCI, Inc., Introducing the V.A.C. GranuFoam Silver Dressing, *Flyer*, 2 pages.
KCI, Inc. V.A.C. Therapy (Negative Pressure Wound Therapy), Medicare Part-B Documentation Guidelines, May 2001, Lit. No. 26-B-104, 1-19.
KCI, Inc., Vacuum Assisted Closure (VAC) from Wound Healing, *Evidence Note 5, NHS Quality Improvement Scotland*, Nov. 2003, 1 page.
Keen, W.W., Ed., Surgery, Its Principles and Practice, 1919, W. B. Saunders Company, p. 56, excerpt, 1919.
Keith, C.F., Wound management Following Head and Neck Surgery, *Nursing Clinics of North America*, Dec. 1979, 14(4) 761-779.
Kennard, H.W., Bier's Hyperaemia, *Brit. Journ. Nurs.*, Mar. 20, 1909, 223.
Kim, S.H., et al., Wangensteen Suction Drainage, apparatus in Neurosurgical Practice, *Dept. of Neurosurgery, Yonsei University of College of Medicine, Seoul, Korea*, 1975, 159-160, Abs. (in Korean and Abstract in English).
Klemp, P., et al., Subcutaneous Blood Flow in Early Male Pattern Baldness, *Journ. of Investigative Derm.*, 1989, 725-726.
Kloth, L.C. and J.M. Mcculloch, Wound Healing Alternatives in Management, 3rd Ed., Chap. 10, 339-352, 2002.
Knight, Marie Ray, A Second Skin for Patients with Large Draining Wounds, Nursing, Jan. 1976, p. 37, USA.
Kohlman, Phyllis A., et al, "Pouching Procedure to Collect Drainage From Around a Biliary Drainage Catheter," Ostomy/Wound Management, Nov./Dec. 1991, pp. 47-50, vol. 37.
Kordasiewicz, L.M., Abdominal Wound with a Fistula and Large Amount of Drainage Status after Incarcerate Hernia Repair, *J. WOCN*, May/Jun. 2004, 31(3), 150-153.
Kremlin Papers, A Collection of Published Studies Complementing the Research and Innovation of Wound Care, from *Vestnik Khirurgii, BlueSky Publishing, A Div. of BlueSky Medical Group Inc.*, 2004. 17 pages.
Landes, R.R. and I. Melnick, An Improved Suction Device for Draining Wounds, *Arch. Surg.*, May 1972, 104, p. 707.
Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.
Larichev, A.B., Vacuum Therapy of Wounds and Wound Infection, 1st. Ed., *BlueSky Publishing*, 2005.237 pgs.
Lee, J.H. and H.J. Yang, Application of Medifoam B® & Negative Pressure Therapy for the Auxiliary Treatment of Pressure Sore, *Dept. Plastic and Reconstructive Surg., College of Medicine, Eulji Univ., Daejeon, Korea, Abs.* Sep. 31, 2004, 1 page.
Linden van der, Willem, Randomized Trial of Drainage After Cholecystectomy, Modern Operative Techniques, Voluje 141, Feb. 1981, pp. 289-294.
Lockwood, C.B., Aseptic Surgery, Drainage, *Brit. Journ. Nurs.*, Mar. 26, 1904, 245.
Luchette, F.A., When Should the General Surgeon Leave the Abdomen Open?, Division of Trauma, Surgical Critical Care and Burns, Loyola University Medical Center, Maywood, Illinois., 37 pages. (date N/A).
Lumley, J.S.P., et al., The Physical and bacteriological Properties of Disposable and Non-Disposable Suction Drainage Units in the Laboratory, *Br. J. Surg.*, 1974, 61, 832-837.
Lundvall, J. and T. Lanne, Transmission of Externally applied Negative pressure to the Underlying Tissue: A Study on the Upper Arm of Man, *Acta Physiol. Scand.* 1989, 136, 403-409.

Magee, C., et al., Potentiation of Wound Infection by Surgical Drains, *Amer. Journ. of Surg.*, May 1976, 131, 547-549.
Maitland and Mathieson, Suction Drainage, *Brit. J. Surg,*, Mar. 1970, 57(3), 195-197.
Mayo, C.W., The One-Stage Combined Abdominoperineal Resection for Carcinoma of the Rectum, RectoSigmoid and Sigmoid, *Surgical Clinics of North America, Aug. 1939, Mayo Clinic Number*, 1011-1012.
McFarlane, R. M., "The Use of Continuous Suction Under Skin Flaps", F.R.C.S.(c), vol. 1, pp. 77-86 (1958).
Mcguire, S., Drainage after Abdominal Section, *Br. Journ. of Nurs.*, Dec. 15, 1903, 447-449.
McLaughlan, James, Sterile Microenvironment for Postoperative Wound Care, The Lancet, pp. 503-504, Sep. 2, 1978.
Mendez-Eastman, S., Guidelines for Using Negative Pressure Wound Therapy, *Advances in Skin & Wound Care*, 14(6), Nov./Dec. 2001, 314-325.
Mendez-Eastman, S., When Wounds Won't Heal, *RN*, Jan. 1998, 2-7.
Meyer and Schmieden, Bier's Hyperemic Treatment, *Published 1908 W. B. Saunders Company*, 44-65.
Miller, M.S. and C. Mcdaniel, Treating a Pilonidal Cystectomy Abscess Wound with the BlueSky Medical Versatile 1™ Negative Pressure Wound Therapy, *The Wound Healing Center*, Terre Haute, Indiana, Case Study 2004-2006, 1 page.
Miller, M.S., APWCA Case #3: Using Negative Pressure for Wound Therapy, *Podiatry Management*, Jun./Jul. 2005, 121-126.
Miller, M.S., Commentary: New Microvascular Blood Flow Research Challenges Practice Protocols in Negative Pressure Wound Therapy, *Wounds* 2005, 17(10) 290-294.
Miller, M.S., et al., Negative Pressure Wound Therapy Options Promote Patient Care, Biomech, Sep. 2005, Downloaded from internet http://www.biomech.com , Jan. 19, 2007.
Milsom, I. and A. Gustafsson, An Evaluation of a Post-Operative Vacuum Drainage System, *Curr. Med. Res. Opin.* (1979), 6, 160-164.
Moloney, G. E., "Apposition and Drainage of Large Skin Flaps by Suction", ANZ Journal of Surgery vol. 26, Issue 3, Feb. 1957, pp. 173-179.
Morykwas, M.J., et al., Effects of Varying Levels of Subatmospheric Pressure on the Rate of Granulation Tissue Formation in Experimental Wounds in Swine, *Abs., Ann. Plast. Surg.* 2001, 47: 547.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Moserova, J. and E. Houskova, The Healing and Treatment of Skin Defects, 1989, 116-143.
Moss, W., What is Cellulitis? Describe Some Forms of Treatment You Would Expect to be Used for Cellulitis of the Arm, *Brit. Journ. Nurs.*, Nov. 1935, 282.
Mulder, G.D., Ed., et al., Clinicians' Pocket Guide to Chronic Wound Repair, *Wound Healing Publications*, Spartanburg, SC, 1991, 54-55.
Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.
Nakayama et al., Ann. Plast. Surg., 26: 499-502 (1991), "A New Dressing Method for Free Skin Grafting in Hands.".
Nakayama, Y., et al., "A New Method for the Dressing of Free Skin Grafts", Plastic and Reconstructive Surgery, Dec. 1990 pp. 1216-1219, UK
Nasser, A.N., The Use of the Mini-Flap Wound Suction Drain in maxillofacial Surgery, *Annals of the Royal College of Surgeons of England*, 1986, 68, 151-153.
Navsaria, P.H., et al., Temporary Closure of Open Abdominal Wounds by the Modified Sandwich-Vacuum Pack Technique, *Br. Journ. Surg.*, 2003, 90, 718-722.
Nghiem, D.D., A Technique of Catheter insertion for Uncomplicated Peritoneal Dialysis, Surgery, *Gynecology & Obstetrics*, Dec. 1983, 157, 575-576.
Nicholas, J.M., Options for Management of the Open Abdomen, Presentation from Emory University School of Medicine, 66 pgs.

(56) References Cited

OTHER PUBLICATIONS

Invited Speaker American College of Surgeons 32nd Annual Spring Meeting, General Session 12—Presentation and Panel Discussion on the Open Abdomen in General Surgery—How Do You Close the Abdomen When You Can't—Bostom Marriott Copley Place Hotel, Boston, MA Apr. 26, 2004.

Nightingale, K., Making Sense of wound Drainage, Nursing time Jul. 5, 1989, 85(27), 40-42.

O'Byrne, C., Clinical Detection and Management of Postoperative Wound Sepsis, Nursing Clinics of North American, Dec. 1979, 14(4), 727-741.

Ohotskii, V.P., et al., Usage of Vacuum Suction During the Primary Surgical Debridement of Open Limb Injuries, Sovetskaya Medicina, Jan. 1973, 17-20 (in Russian with English translation).

Olenius et al., "Mitotic Activity in Expanded Human Skin." Plastic and Reconstructive Surgery. Feb. 1993. 213-215.

Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.

Orgill, D. P., et al., Microdeformational Wound Therapy—A New Era in Wound Healing, Tissue Engin. and Wound Healing Laboratory, Brigham and Women's Hospital, Business Briefing: Global Surgery—Future Direction 2005, 22.

Orgill, D., et al., Current Concepts and Approaches to Wound Healing, Critical Care Medicine, Sep. 1988, 16(9), 899-908.

Orringer et al., "Management of Wounds in Patients with Complex Enterocutaneous Fistulas," Surgery, Gynecology, & Obstetrics, Jul. 1987, vol. 165, pp. 79-80.

Oschsner, A.J., Surgical Diagnosis and Treatment, 1921, 11, 266-269.

Parker, M.J. and C. Roberts, Closed suction Surgical Wound Drainage after Orthopaedic Surgery, Cochran Database of Systematic Review 2005, 3, 3 pages.

Parulkar, B.G., et al., Dextranomer Dressing in the Treatment of Infected Wounds and Cutaneous Ulcers, J. Postgrad. Med., 1985, 31(1), 28-33.

Putney F. Johnson, "The Use of Continuous Negative Pressure after Laryngectomy and Radical Neck Dissection", Surgery, Gynecology & Obstetrics, Aug. 1956, pp. 244-246, USA.

Raffl, Arthur B., "Use of Negative Pressure Under Skin Flaps After Radical Mastectomy," Dept. of Surgery, State Univ. of N.Y., College of Medicine, Syracuse, NY, Submitted for publication Apr. 1953, p. 1048, USA.

Ramirez, O.M., et al., Optimal Wound Healing under Op-Site Dressing, Ideas and Innovations, 73(3), pp. 474-475.

Rammensee, H.G., Untersuchung der Lymphozytenin filtrate in Implantierte PVA-Schwämme nach der Therapie infizierter Wunden mit Vakuumversiegelung, Aus dem Interfakulatären Institut für Zellbiologie der Universität Tübingen Abeilung Immunologie Abteilungsleter, 2004, 119 pgs.

Ranson, John H. M.D., Safer Intraperitoneal Sump Drainage, Surgery Gynnecology and Obstetrics, pp. 841-42, 1973 vol. 137.

Redon, H. and J. Troques, La Fermeture Sous Depression des Plaies Etendues, Academe de Chirurgie, Mar. 1954, 304-306. (in French).

Redon, H., Closure of Large Wounds under a Partial Vacuum, Paris, Notes on Practical Medicine, published under L. Rouques, 1-3.

Reedy, J., The Science Behind Wound Healing, UW Health Sciences/UW Medicine News and Community Relations, Winter/Spring 2005, 4 pages.

Reimann, D., et al., Successful Treatment Due to Vacuum Seal Technique of a Severe Scedosporium Apiospermum Skin Infection in a Renal Transplant Recipient, Nephrol. Dial. Transplant, 2004, 19 (1), 245-248.

Retro Search, Wound Drainage citations, Biological Abstracts, Downloaded from Internet, http://www.nerac.com, Dec. 4, 2001, 1-213.

Richter, Treatment of Inflammatory Conditions of the Skin with Hot Baths, Brit. Journ. Nurs., Aug. 25, 1906, 149.

Roberts, R.H., et al., Randomised Trial of Medinorm LVS and Surgivac Drainage System after Operations for Breast Cancer May 1999, Amer. Journ. Surg., Feb. 1997, 2 pgs.

Robertson, "The Influence upon Wound Contraction of a Negative Interstitial Fluid Pressure Within Granulation Tissue, " Journal of Anatomy, 1969, vol. 105, No. 1, pp. 189.

Rosser, C.J., et al., A New Technique to Manage Perineal Wounds, Infections in Urology, Mar./Apr. 2000, 4 pgs.

Royle, G.T. and B.J. Britton, Disposable Drains, Articles of the Royal College of Surgeons of England, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, burns, 1988, 14(4), 323-325.

Sames, C.P., Sealing of Wounds with Vacuum Drainage, Br. Med. Journ., Nov. 5, 1977, p. 1223, Correspondence.

Samson, D., et al., Wound-Healing Technologies: Low-Level Laser and Vacuum-Assisted Closure, Evidence report/Technology Assessment, No. 111, Dec. 2004, AHRQ Publication No. 05-E005-2 97 pages.

Schaffer, D.B., Closed Suction Wound Drainage, Nursing97, Nov., Downloaded from internet www.springnet.com, 62-64. 1997.

Schaum, K.D. Payment Strategies: a New Medicare Part B Wound Care Policy, Advance in Skin and Wound Care, Sep./Oct. 2001, 14(5), 238-240.

Schumann, D., Preoperative Measures to Promote Wound Healing, Nursing Clinics of North America, Dec. 1979, 14(4), 683-699.

Schwab, Peter M. and Kelly, Keith A., "Primary closure of the Perineal Wound After Proctectomy," Mayo Clinic Proc., Mar. 1974, pp. 176-179, vol. 49, US.

Senyutovich, R.V., Napkin Preventing Abdominal Contamination in Performance of Colonic Anastomosis, Abstracts, Downloaded from internet, http://www.mediasphera.ru/surgery/97/1/el-97ref.htm—1997, 1 page.

Shaer, W.D., et al., Inexpensive Vacuum-Assisted Closure Employing a Conventional Disposable Closed-Suction Drainage System, Plastic and Reconstructive Surgery, Jan. 2001, 292.

Sheen, A.W., Some Experiences of Shell Wounds in the Present War, (excerpt), Brit. Journ. Nurs., Jan. 16, 1915, 42.

Sheppard, M.D., "Sealed Drainage of Wounds", The Lancet, Jun. 14, 1952, pp. 1174-1176.

Smith, L.A., et al., Vacuum Pack Technique of Temporary Abdominal Closure: A Four-Year Experience, Amer. Surg., Dec. 1997, 63(12), 1102-1108.

Spengler, Michael D., el al, "Performance of Filtered Sump Wound Drainage Tubes", Surgery, Gynecology & Obstetrics, Mar. 1982, pp. 333-336, vol. 54, USA.

Steenvoorde, P., et al., Failure of the Topical Negative Pressure Abdominal Dressing System in the "Fat" Open Abdomen: Report of a Case and Review of the Literature, Wounds, 2006, 18(2), 44-50.

Stewart, M. F., et al., Cleaning v Healing, Community Outlook, Aug. 1985, 22-26.

Suarez, L., NPWT vs Standard Care: Which is the Better Treatment for Complex Wounds?, Diabetic Microvascular Complications Today, Jan./Feb. 2006, 26-27.

Surgidyne, Closed Systems for Management of Wound Drainage, Brochure and Catalog, Downloaded from internet, www.sterion.com, 6 pages (date N/A).

Svedman, "Irrigation Treatment of Leg Ulcers," The Lancet, Sep. 3, 1983, pp. 532-534.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swanson, L., Solving Stubborn-Wound problem Could Save Millions, Team Says, JAMC, 23 FEVR, 1999: 160(4), p. 556.

Taylor, Virginia, Meeting the Challenge of Fistulas & Draining Wounds, Nursing, Jun. 1980, pp. 45-51, USA.

Teder and Svedman et al., "Continuous Wound Irrigation in the Pig," Journal of Investigative Surgery, 1990, vol. 3, pp. 399-407.

(56) References Cited

OTHER PUBLICATIONS

Tennant, C.E., "The Use of Hyperemia in the Postoperative Treatment of Lesions of the Extremities and Thorax," Jour. A. M. A., May 8, 1915, pp. 1548-1549.
Tenta, L.T., et al., Suction Drainage of Wounds of the Head and Neck, *Surg. Gyn. & Ob.*, Dec. 1989, 169, p. 558.
The Bier Treatment, *Brit. Journ. Nurs.*, Jun. 6, 1908, 452.
The British Journal of Nursing, Nov. 4, 1911, 368.
Thomas, Stephen "Wound Management and Dressings" 35-42 (1990).
Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (in German with English Translation).
Tribble, David E. M.D., An Improved Sump Drain-Irrigation Device of Simple Construction, Archives of Surgery New York, pp. 511-513, 1972 vol. 105.
Tricenturion, Article for Negative Pressure Wound Therapy Pumps—Policy Article, CMS, Jan. 2006, Downloaded from Internet www.hhs.gov.
Tuberculous Joints, *Nursing record & Hospital World*, Apr. 28, 1894, 280.
Urschel, J.D., et al., The Effect of Mechanical Stress on Soft and Hard Tissue Repair; A Review, *Br. Journ. Plast. Surg.*, 1988, 41, 182-186.
Usypov, Y. N. and M.V. Ephfanov, Active Drainage of wounds, Dept. of Hospital Surgery, Army Medical Academy, Leningrad, *Vestnik Chirurgia* 1987, Apr. Edition, 42-45 (in Russian with English translation).
Valenta, A.L., Using the Vacuum Dressing Alternative for Difficult Wounds, *AIN*, Apr. 1994, 44-45.
Van Heurn, L.W.E. and P.R.G. Brink, Prospective Randomized Trial of High versus Low Vacuum Drainage after Axillary Lymphadenectomy, *Br. Journ. Surg.* 1995, 82, 931-932.
Van Way III, C.W., Prevention of Suction-Induced Gastric mucosal damage in Dogs, *Critical Care Medicine*, Aug. 1987, 15(8), 774-777.
Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.
Vijanto, J. and J. Raekallio, Local Hyperalimentation of Open Wounds, *Br. J. Surg.*, 1976, 63, 427-430.
Waymack, J. P., et al.: "An evaluation of Aquaphor Gauze dressing in burned children", Burns Include therm Inj. Aug. 1986;12(6):443-8.
Wayne, M.A., Cook Pneumothorax Catheter Set, Wayne Pneumothorax Catheter Set, *Cook Critical Care, Cook Incorporated* 1997, 3 pgs.
Webster's Revised Unabridged Dictionary, published 1913 by C. & G. Merriam Co., definition of Flapper Valve, downloaded from Free Online Dictionary.
Wells Johnson Company, 2045 N. Forbes Blvd., Suite 106, Tuscon, AZ. Point 5 Aspirator, 1 page.
Westaby, S., et al., "A Wound Irrigation Device", The Lancet, Sep. 2, 1978, pp. 503-504.
Westaby, S., Wound Care No. 11, *Nursing Times*, Jul. 21, 1982, 41-48.
White, R.A., et al., Vacuum-Assisted Closure Complicated by Erosion and Hemorrhage of the Anterior Tibial Artery, *Journal of Orthopaedic Trauma*, Jan. 2005, 19(1), 56-59, Nov. 9, 2005.
Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from internet Nov. 30, 2003.
Windows on Medical Technology, Vacuum-Assisted Wound Closure for Chronic and Acute Wounds, *ECRI Health Technology Assessment Information Service*, Oct. 2000, 38, 1-21.
Witkowski, J.A. and Parish, L.C., Synthetic Dressings: Wound Healing in the '80s, *Hospital Therapy*, Nov. 1986, 75-84.
Wolthuis, Roger A., et al, "Physiological Effects of Locally Applied Reduced Pressure in Man," Physiological Reviews, Jul. 1974, pp. 566-595 vol. 54, No. 3, USA.
Wooding-Scott, Margaret, et.al, "No Wound is Too Big for Resourceful Nurses," RN, Dec. 1988, pp. 22-25, USA.
Worth, M.H. and H.W. Andersen, The Effectiveness of Bacterial Filtration in Vented Wound Drains, *Journ. of Surg. Research*, 1979, 27, 405-407.
Wright, P., Sales Soar for BlueSky's Wound-Healing Device, *North County Times*, Nov. 2006, D-1 and D-6 (newspaper article).
Wu, P., et al., In Vitro Assessment of Water Vapour Transmission of Synthetic Wound Dressings, *Biomaterials*, 1995, 16(3), 171-175.
Wu, W.S., et al. Vacuum therapy as an intermediate phase in wound closure: a clinical experience, Eur J Past Surg (2000) 23: 174-177.
Wysocki et al., "Wound Fluid form Chronic Leg Ulcers Contains Elevated Levels of Metalloproteinases MMP-2 and MMP-9." The Society for Investigative Dermatology, Inc. Jul. 1993. 64-68.
Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm, 1 page.
Zamierowski, David S., Letter:"All Foam Sponges are not Equal in Vacuum Dressings," British Journal of Plastic Surgery, 1999, 52, 78-81, p. 79, United Kingdom.
Zhetimkarimov, D.S. and V.K. Ostrovsky, The Applied Significance of Anatomic Pecularities of Greater Momentum, Contents, Surg. No. 6, 1997, Downloaded from internet http://www.mediasphera.ru/surgery/97/6/e6-97ref.htm, 1 page.
Zivadinovic, Gorica, Veljko Dukic, and Sava Filipovic, Our Experience in the Treatment of Patients with Arterial Failure of the Extremities Using the Vacusac Unit, Timocki Medicinski Glasnik, Year XII, Zajecar, 1987 No. 1, pp. 55-65.
Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajecar, 1986, No. 3-4, pp. 161-164.

\* cited by examiner

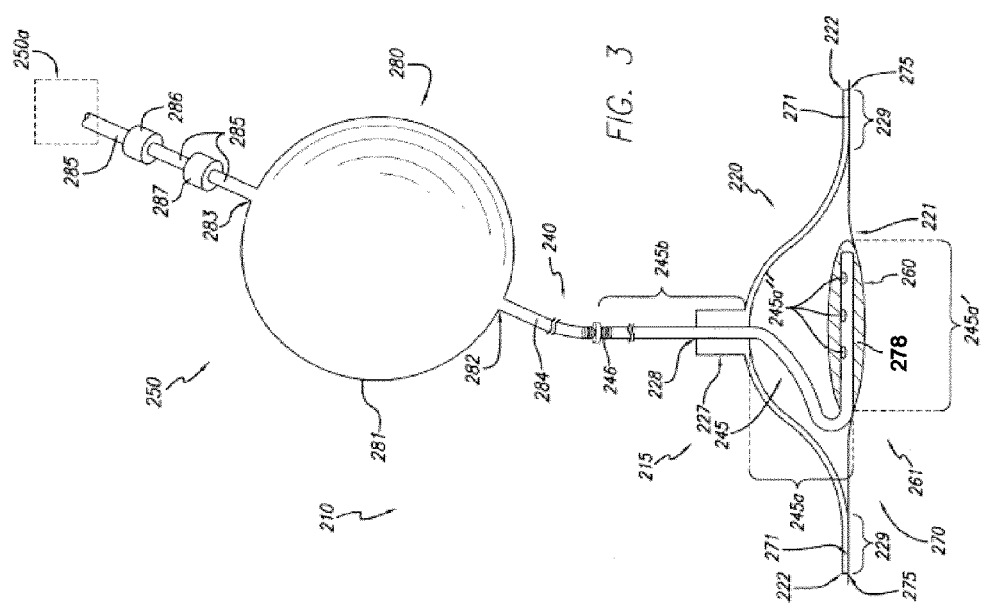

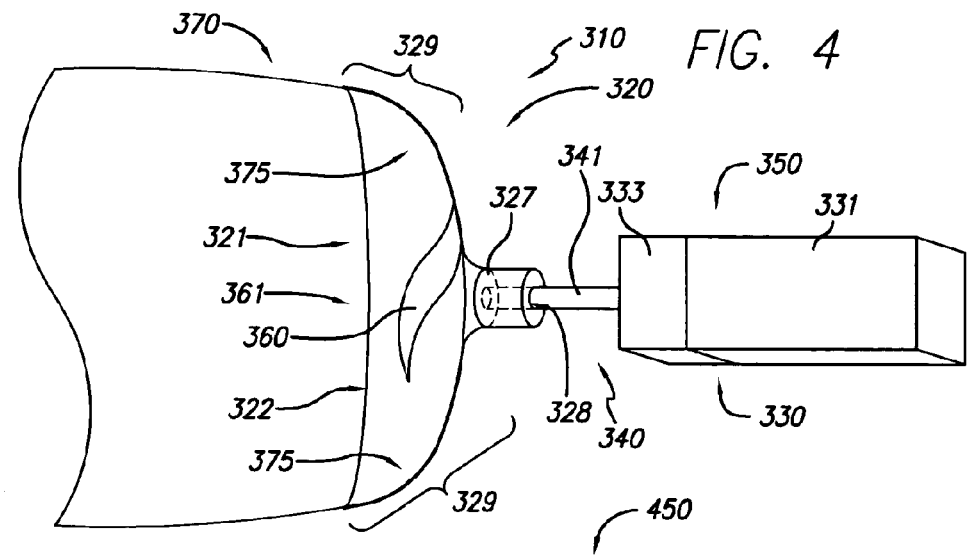
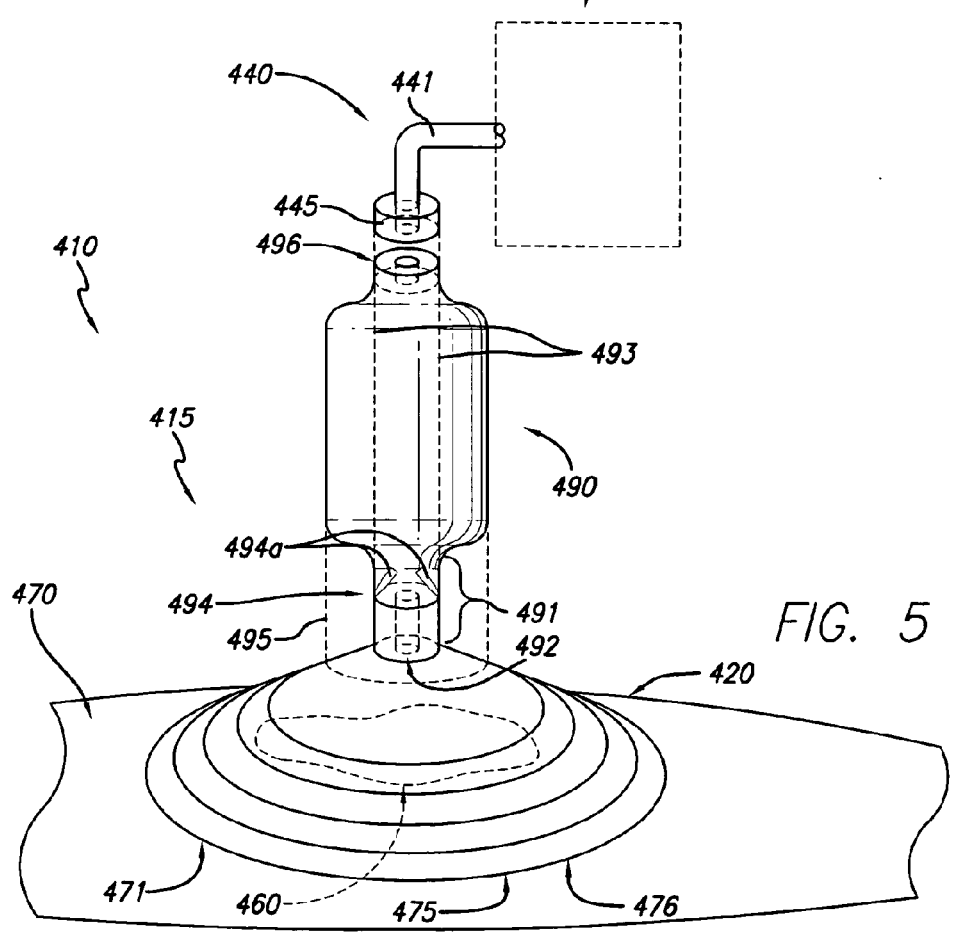

REDUCED PRESSURE TREATMENT SYSTEM

CROSS-REFERENCE TO RELATED APPLICATIONS

This application is a continuation-in-part of U.S. application Ser. No. 12/719,715, filed on Mar. 8, 2010, which is a continuation of U.S. application Ser. No. 11/098,203, filed on Apr. 4, 2005, now U.S. Pat. No. 7,708,724, which claims the benefit of U.S. Application No. 60/559,727, filed on Apr. 5, 2004, each of which is incorporated herein by reference in its entirety. This application is also a continuation-in-part of U.S. application Ser. No. 11/064,813, filed on Feb. 24, 2005, which claims the benefit of U.S. Application No. 60/573,655, filed on May 21, 2004, each of which is incorporated herein by reference in its entirety. This application is also a continuation-in-part of U.S. application Ser. No. 11/098,265, filed on Apr. 4, 2005, which is a continuation-in-part of U.S. application Ser. No. 11/064,813, filed on Feb. 24, 2005, and which claims the benefit of U.S. Application No. 60/559,727, filed on Apr. 5, 2004, each of which is incorporated herein by reference in its entirety.

BACKGROUND OF THE INVENTION

The present invention generally relates to treatment of wounds, and more specifically to improved apparatus and methods for treating a wound or a portion of a wound on a body by applying reduced pressure to the body at the site of the wound. In this context, the terms "wound" and "body" are to be interpreted broadly, to include any wound, body, or body part that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed with the U.S. Patent and Trademark Office on Aug. 28, 2003 and published as U.S. Publication No. 2004/0073151 A1. The disclosure of this U.S. patent application is incorporated herein by reference. Another system is disclosed in U.S. patent application Ser. No. 11/026,733, entitled "Improved Reduced Pressure Wound Treatment Appliance," which was filed with the U.S. Patent and Trademark Office on Dec. 30, 2004, now U.S. Pat. No. 7,128,735. The disclosure of this U.S. patent application is also incorporated herein by reference. Yet another system is disclosed in U.S. patent application Ser. No. 11/064,813, entitled "Improved Flexible Reduced Pressure Wound Treatment Appliance," which was filed with the U.S. Patent and Trademark Office on Feb. 24, 2005 and published as U.S. Publication No. 2005/0261642 A1. The disclosure of this U.S. patent application is also incorporated herein by reference.

Reduced pressure wound treatment systems currently known in the art commonly involve placing a treatment device that is impermeable to liquids over the wound, using various means to seal the treatment device to the tissue of the patient surrounding the wound, and connecting a source of reduced pressure (such as a vacuum pump) to the treatment device in a manner so that an area of reduced pressure is created under the treatment device in the area of the wound. The systems also typically act to remove exudate that may be aspirated from the wound. Thus, such systems also typically have a separate collection device located between the reduced pressure source and the treatment device to collect. This collection device represents a separate source of expense in reduced pressure wound treatment. In addition, it is advantageous in some circumstances to remove exudate from the wound so that the exudate does not remain in the presence of the wound. For example, healing of the wound may be enhanced by the removal of exudate from the wound in some circumstances. In yet other cases, it may be advantageous to be able to gain physical access to the wound without having to remove the treatment device from the body surrounding the wound. For example, it may be desirable to monitor or treat the condition of the wound during the treatment process. If the treatment device is sealed to the body using an adhesive tape, removing the adhesive tape to monitor or treat the wound may cause discomfort and pain for the patient.

Therefore, there is a need for a wound treatment device that can eliminate the requirement for a separate collection device to collect exudate from the wound. This type of device could reduce the expense involved in wound treatment by eliminating the need for the collection device. There is also a need for such a treatment device to remove exudate from the presence of the wound to aid in wound healing. It may also be desirable for this type of treatment device to be disposable in certain circumstances. Further, there is a need for a treatment device that would allow for physical access to the wound without the need for removing the treatment device from the body. This type of device could enhance patient comfort. In addition, where the access is simple and quickly obtained, it could also decrease the cost of wound treatment by reducing the time required of healthcare practitioners to be involved in wound treatment. Finally, there is also a need for a reduced pressure treatment system that is relatively inexpensive, while meeting the needs described above.

Reduced pressure wound treatment systems currently known in the art also commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. However, the covers currently known and used in the art have a number of disadvantages. For example, in one version they tend to be in the form of a flexible sheet of material that is placed over the wound and sealed to the surrounding tissue using an adhesive, adhesive tape, or other similar means. As tissue swelling in the area of the wound decreases during the healing process, the adhesive may begin to stretch the surrounding tissue, as well as tissue within the wound, resulting in discomfort and pain to the patient. This may necessitate more frequent cover changes, increasing the time medical staff must expend in treating the wound. This additional time, of course, also tends to increase the expense involved in treating the wound. In addition, these types of covers can typically only be used where there is normal tissue adjacent to the wound to which the adhesive seal can be attached. Otherwise, the seal must be made in a portion of the area of the wound, and exudate from the wound tends to break the seal so that reduced pressure cannot be maintained beneath the wound cover. Thus, such covers (and many other covers requiring adhesive seals) may typically only be used to treat an entire wound, as opposed to only a portion of a wound. Further, the adhesive seal creates discomfort for the patient when the sheet cover is removed. In other versions, the covers tend to be rigid or semi-rigid in nature so that they are held away from the surface of the wound. In these versions, the covers are sometimes difficult to use because the shape and contour of the patient's body in the area of the wound do not readily adapt to the shape of the cover. In such cases, additional time is required for the medical staff to adapt the cover for its intended use. This also increases the expense of wound treatment. In addition, it is also often necessary to use an adhesive, adhesive tape, or other similar means to seal the rigid or semi-rigid cover to the tissue surrounding the wound. In these instances, the same disadvantages discussed above with respect to the first version also apply to this version as well. In still other cases, the rigid and semi-rigid covers must be used with padding in the area where the cover is adjacent to the patient to prevent the edges of the cover from exerting undue pressure on the tissue surrounding the wound. Without the padding, the patient may experience pain and discomfort. The additional padding, which may make the cover itself more expensive, may also take a greater amount of time to place on the patient for treatment purposes. These covers may also have the problem of placing tension on the surrounding tissue as the swelling in the area of the wound decreases during the healing process. In yet another version, covers are constructed of combinations of flexible materials and rigid materials. In these versions, a flexible member, such as a flexible sheet, is typically supported by a rigid or semi-rigid structure that is either placed between the flexible member and the wound or in the area above and outside the flexible member. In either case, the flexible member must usually be sealed to the tissue surrounding the wound using an adhesive, adhesive tape, or other similar means. This seal creates the same problems described above. In addition, the same problems described above with respect to rigid and semi-rigid structures are also often present. In all of the versions described above, it may be difficult to tell if reduced pressure in the area of the wound under the cover has been lost because the cover itself does not generally provide a visual clue of such loss.

Therefore, there is a need for a reduced pressure wound treatment system that has a means to enclose all or a portion of a wound without the need for an adhesive seal. There is also a need for such enclosing means to be flexible, so that it adapts to changing shapes and contours of the patient's body as wound healing progresses. Further, there is a need for an enclosing means that is adaptable to a wide variety of patient body shapes and contours. There is also a need for an enclosing means that is simple to apply to the patient's body, and simple to remove from the patient's body. Such enclosing means would also take less time to apply and remove, reducing the expense involved in wound treatment. There is also a need for an enclosing means that is relatively inexpensive, while meeting the needs described above. In addition, there is a need for an enclosing means that may be used within the wound (or a portion thereof), without the need to seal the enclosing means to normal tissue surrounding the wound. Further, there is a need for an enclosing means that flexes with movement of the portion of the body surrounding the wound, without the need for an adhesive seal or rigid or semi-rigid structure. Finally, there is a need for an enclosing means that provides a visual clue of loss of reduced pressure in the area of the wound under the enclosing means.

SUMMARY OF THE INVENTION

The present invention is directed to reduced pressure treatment appliances and methods that satisfy the needs described above. As described in greater detail below, they have many advantages over existing reduced pressure treatment apparatus and methods when used for their intended purpose, as well as novel features that result in new reduced pressure treatment appliances and methods that are not anticipated, rendered obvious, suggested, or even implied by any of the prior art apparatus or methods, either alone or in any combination thereof.

One embodiment of the present invention is directed to a reduced pressure wound treatment appliance and methods that satisfy the needs described above. As described in greater detail below, they have many advantages over existing reduced pressure wound treatment apparatus and methods when used for their intended purpose, as well as novel features that result in a new reduced pressure wound treatment appliance and methods that are not anticipated, rendered obvious, suggested, or even implied by any of the prior art apparatus or methods, either alone or in any combination thereof.

In accordance with one embodiment, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In some embodiments, the wound treatment appliance is comprised of an impermeable flexible overlay and reduced pressure supply means, which are described in more detail below and are used to connect the flexible overlay to a reduced pressure supply source that provides a supply of reduced pressure to the flexible overlay. In some embodiments, the flexible overlay is adapted to be placed over and enclose all or a portion of a wound on the surface of the body of a patient. The flexible overlay is also adapted to maintain reduced pressure under the flexible overlay in the area of the wound. The flexible overlay collapses in the approximate direction of the area of the wound to be treated when reduced pressure is supplied to the volume under the flexible overlay in the area of the wound. This collapse causes the formation of an approximately hermetic seal (described in more detail below) between the flexible overlay and the body in the area of the wound. In some embodiments, the flexible overlay is further comprised of an interior surface facing the area of the wound to be treated, wherein the surface area of the interior surface is greater than the surface area of the portion of the body to be enclosed by the flexible overlay. In other embodiments, the flexible overlay is further comprised of a bottom portion having an approximately elongated conical shape with an approximately elliptically-shaped open end at the base of the elongated conical bottom portion. In these embodiments, the approximately elliptically-shaped open end at the base is sized to be placed over and enclose the area of the wound to be treated. In yet other embodiments, the flexible overlay (as opposed to only the bottom portion thereof) has an approximately elongated conical shape having an approximately elliptically-shaped open end at its base. In these embodiments, the approximately elliptically-shaped perimeter of the open end at the base of the flexible overlay is positioned over all or a portion of the wound on the surface of the body. In some of these embodiments, the flexible overlay further comprises a port located approximately at the apex of the elongated conically-shaped flexible overlay. In these embodiments, the reduced pressure supply means is operably connected to the port. In yet other embodiments, the flexible overlay is comprised of at least three cover portions, each of such cover portions being approximately triangular in shape. One point of each of the at least three triangular-shaped cover portions are joined to form an apex of the flexible overlay and one side of each at least three triangular-shaped cover portions adjacent to the apex is joined to an adjacent side of another of such at least three triangular-shaped cover portions so that the bases of the at least three triangular-shaped cover portions form an opening sized to be placed over and enclose the area of the wound to be treated. In some of these embodiments, the flexible overlay is further comprised of a port located approximately at the apex of the flexible overlay and the reduced pressure supply means is operably connected to the port. In yet other embodiments, the flexible overlay may be cup-shaped. In still other embodiments, at least one fold forms in the surface of the flexible overlay when it collapses, so that fluids aspirated by the wound flow along the at least one fold to the reduced pressure supply means, where they are removed from the flexible overlay by means of the reduced pressure supply means cooperating with the reduced pressure supply source. In other embodiments, the flexible overlay is further comprised of suction assist means, which assist in the application of reduced pressure to the area of the wound and removal of exudate from the wound. In some of these embodiments, the suction assist means may be channels disposed in, or raised portions disposed on, the surface of the flexible overlay. In other embodiments, the appliance further comprises supplemental sealing means, which are described in more detail below, to form a seal between the flexible overlay and the body in the area of the wound. In yet other embodiments, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the flexible overlay in the area of the wound by means of the suction drain. The suction drain extends from the reduced pressure supply means into the volume under the flexible overlay in the area of the wound.

In some embodiments, the wound treatment appliance is comprised of a wound treatment device and a vacuum system. In some embodiments, the vacuum system is further comprised of a reduced pressure supply source that provides a supply of reduced pressure and reduced pressure supply means to operably connect the wound treatment device to the reduced pressure supply source, so that the volume under the wound treatment device in the area of the wound is supplied with reduced pressure by the reduced pressure supply source. In various embodiments, the wound treatment device and the reduced pressure supply means may generally have substantially the same structure, features, characteristics and operation as the appliance described above in connection with other embodiments previously described.

In some embodiments, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments, the reduced pressure supply means is comprised of flexible tubing. In other embodiments, the reduced pressure supply means is further comprised of a collection system that is operably positioned between the wound treatment device and the reduced pressure supply source. In some of these embodiments, the collection system comprises a container to receive and hold fluid aspirated from the wound and pressure halting means to halt the application of reduced pressure to the wound when the fluid in the container exceeds a predetermined amount. In other embodiments, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments, the wound treatment appliance further comprises tissue protection means, which are described in more detail below, to protect and strengthen the body tissue that is adjacent to the flexible overlay at the wound site. In some of these embodiments, the tissue protection means is a hydrocolloid material.

In some embodiments, the wound treatment appliance is comprised of a wound treatment device, a vacuum system, and wound packing means, which are described in more detail below, that are positioned between the wound treatment device and the portion of the wound to be treated. In various embodiments, the wound treatment device and the vacuum system may generally have substantially the same structure, features, characteristics and operations as the wound treatment device and the vacuum system, respectively, described above in connection with the other embodiments of the invention. In some embodiments, the flexible overlay of the wound treatment device is placed over all or a portion of the wound and the wound packing means when the flexible overlay is positioned on the surface of the body at the wound site. In some embodiments, the wound packing means is comprised of absorbent dressings, antiseptic dressings, nonadherent dressings, water dressings, or combinations of such dressings. In some embodiments, the wound packing means is preferably comprised of gauze or cotton or any combination of gauze and cotton. In still other embodiments, the wound packing means is comprised of an absorbable matrix adapted to encourage growth of the tissue in the area of the wound under the flexible overlay into the matrix. The absorbable matrix is constructed of an absorbable material that is absorbed into the epithelial and subcutaneous tissue in the wound as the wound heals. Because of the absorbable nature of the absorbable matrix, the matrix should require less frequent changing than other dressing types during the treatment process. In other circumstances, the matrix may not need to be changed at all during the treatment process. In some embodiments, the absorbable matrix is comprised of collagen or other absorbable material. In some embodiments, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the impermeable flexible overlay in the area of the wound by means of the suction drain. In these embodiments, the suction drain extends from the reduced pressure supply means into the volume under the impermeable flexible overlay in the area of the wound. In some embodiments, the suction drain is further comprised of a distal end portion and the distal end portion has at least one perforation in the surface thereof. In some embodiments, the distal end portion of the suction drain is positioned within the interior volume of the wound packing means.

In some embodiments, the wound treatment appliance is comprised of a wound treatment device and a vacuum system. In various embodiments, the wound treatment device is comprised of an impermeable flexible overlay and a seal. The impermeable flexible overlay is sized to be placed over and enclose the area of the wound to be treated and is adapted to maintain reduced pressure in the area of the wound to be treated. The seal seals the impermeable flexible overlay to the body in the area of the wound in a manner so that reduced pressure is maintained under the impermeable overlay in the area of the wound to be treated. In addition, in various embodiments of the invention, the vacuum system is comprised of a suction bulb, which may (but not necessarily) provide a source of reduced pressure, and reduced pressure supply means, which are described in more detail below, to operably connect the impermeable flexible overlay to the suction bulb, so that the area of the wound under the impermeable flexible overlay may be supplied with reduced pressure by the suction bulb. In some embodiments, the flexible wound cover may be comprised of a flexible overlay that has substantially the same structure, features, characteristics and operation as the flexible overlay described above in connection with other embodiments. In some embodiments, the suction bulb is further comprised of an inlet port and an outlet port, wherein the inlet port is operably connected to the reduced pressure supply means, and the vacuum system further comprises an exhaust tubing member operably connected to the outlet port. In some embodiments, the vacuum system further comprises an exhaust control valve operably connected to the exhaust tubing member. In other embodiments, the vacuum system is further comprised of a filter operably connected to the exhaust tubing member, which prevents the venting of micro-organisms aspirated from the wound or fluids aspirated from the wound or both. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with other embodiments of the invention.

Another embodiment involves a method of treating a wound on a body. In one embodiment, the method comprises the following steps. First, positioning a flexible overlay on the body over the area of the wound to be treated, wherein the flexible overlay is sized to be placed over and enclose the area of the wound to be treated and adapted to maintain reduced pressure in the area of the wound to be treated. Second, operably connecting the flexible overlay with a vacuum system for producing reduced pressure in the volume under the flexible overlay in the area of the wound to be treated. Third, collapsing the flexible overlay in the approximate direction of the wound when reduced pressure is supplied to the volume under the flexible overlay in the area of the wound so that an approximately hermetic seal (described in more detail below) is formed between the impermeable flexible overlay and the body in the area of the wound. Fourth, maintaining the reduced pressure until the area of the wound being treated has progressed toward a selected stage of healing.

In other embodiments, the method further comprises the step of placing tissue protection means on the tissue of the body that is to be approximately adjacent to the flexible overlay, such step being performed prior to positioning the flexible overlay over the area of the wound to be treated. The tissue protection means, which is described in more detail below, protects and strengthens the tissue of the body adjacent to the flexible overlay at the wound site. In yet other embodiments, the method further comprises the step of placing wound packing means (described in more detail above) between the wound and the flexible overlay in the area of the wound to be treated, such step being performed prior to positioning the flexible overlay over the area of the wound to be treated. In still other embodiments, the vacuum system is comprised of a suction bulb and the method further comprises the step of squeezing the suction bulb to reduce its volume and then releasing the suction bulb, so that reduced pressure is produced in the volume under the flexible overlay in the area of the wound. In other embodiments, the reduced pressure under the impermeable overlay in the area of the wound is in the range from approximately 20 mm of Hg below atmospheric pressure to approximately 125 mm of Hg below atmospheric pressure. In still other embodiments, the reduced pressure is applied in a cyclic nature, the cyclic nature providing alternating time periods of application of reduced pressure and without application of reduced pressure.

As is illustrated in the detailed descriptions herein, embodiments of the wound treatment appliance of the present invention meet the needs discussed above in the Background section. For example, in one embodiment of a flexible overlay having a bottom portion with an approximately elongated conical shape, the flexible overlay is placed over and encloses all or a portion of the wound. When the flexible overlay is enclosing all or a portion of the wound, the portions of the flexible overlay positioned adjacent to the surface of the body at the wound site are at (or can be deformed to be at) a relatively acute angle relative to such surface of the body. When reduced pressure is applied to the area under the flexible overlay, the flexible overlay is drawn downward, collapsing the flexible overlay in the approximate direction of the wound. As the flexible overlay collapses, the portions of the flexible overlay adjacent to the perimeter of the opening of the flexible overlay are drawn tightly against the surface of the body at the wound site, thus forming an approximately hermetic seal. References to an "approximately hermetic seal" herein refer generally to a seal that is gas-tight and liquid-tight for purposes of the reduced pressure treatment of the wound. It is to be noted that this seal need not be entirely gas-tight and liquid-tight. For example, the approximately hermetic seal may allow for a relatively small degree of leakage, so that outside air may enter the volume under the flexible overlay in the area of the wound, as long as the degree of leakage is small enough so that the vacuum system can maintain the desired degree of reduced pressure in the volume under the flexible overlay in the area of the wound. In some uses where the collapsing flexible overlay may not produce an approximately hermetic seal that is solely capable of maintaining the reduced pressure in the volume under the impermeable overlay in the area of the wound, it may be necessary to provide supplemental sealing means, which are described in more detail below, and which are used to provide a seal between the portions of the flexible overlay and the body where the approximately hermetic seal is not adequate. As a result, the flexible overlay is simple to apply to the patient. There is also often no need for any other sealing means in most cases, which means that there is usually no need for medical staff to take the time to make a separate seal. Even where the geometry of the surface of the body surrounding the wound may require that supplemental sealing means be used to provide some limited assistance to ensure a seal, the amount of such assistance (such as by applying an adhesive) is limited, especially when compared to current covers in the art. In addition, as swelling of tissue at the wound site decreases, the flexible nature of the flexible overlay allows it to further deform to conform to the changing shape and contours at the wound site. This prevents the patient from being discomforted as the swelling decreases. It also reduces the need to change the covering over the wound as healing progresses. This is generally not true in cases involving flexible, semi-rigid and rigid covers that exist in the art. For example, even where semi-rigid and rigid covers do not utilize an adhesive seal and rely solely upon the reduced pressure to hold them in place, they do not generally change shape enough to flex with substantial changes in the shape and contour of the surrounding body surface. Thus, they may not be appropriate for use with body portions that are subject to such changes, while the flexible nature of the flexible overlay, along with its increased surface area that can bend and flex, allow it to be used in such circumstances without the need for an adhesive seal. In the same way, the flexible overlay may generally be used for unusual geometries of the body at or surrounding the wound because of the overlay's flexible nature and relatively large surface area. In contrast, flexible sheets and semi-rigid and rigid covers may require substantial modification and means to provide an adequate seal. In addition, such covers may require that the patient be partially or wholly immobilized during the treatment process to avoid movement in the area of the body surrounding the wound to avoid breaking the seal. And such covers must usually be sealed to normal tissue surrounding the wound. The flexible overlay, however, may be used within the perimeter of a wound in many cases because there is not typically a need to seal the flexible overlay to normal tissue surrounding the wound. Further, because there is typically no need for an adhesive seal, removal of the flexible overlay merely requires removal of the reduced pressure from the area under the flexible overlay. It is thus simple to remove from the patient. For this reason, it will tend to reduce the time required of medical staff for wound treatment, which will also tend to reduce the cost of wound treatment.

In addition, there is no pain and discomfort for the patient when the flexible overlay is removed. Even if a limited amount of supplemental sealing means (such as an adhesive) are required to provide a seal at a portion of the flexible overlay that is adjacent to the surface surrounding the wound, the reduced amount of supplemental sealing means will cause a corresponding reduction in the amount of such pain and discomfort. Further, some embodiments of the collapsed flexible overlay will have folds in its surface while in the collapsed state, so that fluid aspirated by the wound may flow along the folds to be removed from under the flexible overlay. In some embodiments, the flexible overlay is further comprised of suction assist means, which also assist in the application of reduced pressure to the area of the wound and removal of exudate from the wound. In some of these embodiments, the suction assist means may be channels disposed in, or raised portions disposed on, the surface of the flexible overlay. In addition, if reduced pressure is lost under the flexible overlay, the flexible overlay will expand outward from the wound, providing a visual indication that reduced pressure has been lost. Finally, in some embodiments, the flexible overlay is relatively inexpensive to manufacture, even though it meets the described needs.

In some embodiments, the wound treatment appliance is comprised of a fluid impermeable flexible overlay, a collection chamber to receive and hold fluid aspirated from the wound, collection chamber attachment means to operably attach the collection chamber to the flexible overlay, as described in more detail below, and reduced pressure supply means, which are described in more detail below. In some embodiments, the flexible overlay is adapted to be placed over and enclose all or a portion of the wound. In various embodiments, except as described in more detail below, the flexible overlay has substantially the same structure, features characteristics and operation as the flexible overlay described above in connection with other embodiments. In addition, in some embodiments, the reduced pressure supply means is used to operably connect the collection chamber to a reduced pressure supply source that provides a supply of reduced pressure to the collection chamber, so that the volume within the collection chamber and under the impermeable overlay in the area of the wound to be treated are supplied with reduced pressure by the reduced pressure supply source. In various embodiments, except as described in more detail below, the reduced pressure supply means to connect the reduced pressure supply source to the collection chamber in the embodiments of the invention may have substantially the same structure, features, characteristics, and operation as the reduced pressure supply means described above in connection with other embodiments.

In some embodiments, the flexible overlay is attached by collection chamber attachment means to a collection chamber that receives and holds fluid aspirated from the wound. In some embodiments, the collection chamber may be approximately cylindrical in shape. In various embodiments, the collection chamber attachment means operably attaches the collection chamber to the flexible overlay in a manner so that the fluid and reduced pressure are permitted to flow between the collection chamber and the volume under the flexible overlay in the area of the wound. In some embodiments, the collection chamber is positioned approximately adjacent to the impermeable flexible overlay on the side of the impermeable flexible overlay opposite the wound and the collection chamber attachment means is a rigid or semi-rigid connecting member positioned between the collection chamber and the impermeable flexible overlay. In these embodiments, the connecting member has a port therein that extends between the collection chamber and the flexible overlay. In embodiments where the flexible overlay is approximately elongated-conically shaped, the collection chamber and the collection chamber attachment means may be positioned approximately at the apex of the flexible overlay on the side of the impermeable flexible overlay opposite the wound. In some embodiments, the collection chamber may be approximately cylindrical in shape. In other embodiments, the collection chamber attachment means may be further comprised of a flow control means, which is described in more detail below, operably positioned between the collection chamber and the flexible overlay. In these embodiments, the flow control means permit the fluid to flow from the volume under the flexible overlay in the area of the wound into the collection chamber, but not in the opposite direction. In some of these embodiments, the flow control means may be comprised of a valve. In some of these embodiments, the valve may be comprised of a flapper-type valve. In yet other embodiments, the collection chamber is positioned approximately adjacent to the impermeable flexible overlay on the side of the impermeable flexible overlay opposite the wound and the collection chamber attachment means is comprised of a membrane. In these embodiments, the membrane acts as a barrier separating the collection chamber and the impermeable flexible overlay, so that the membrane acts as a portion of the surface of the collection chamber and a portion of the surface of the impermeable flexible overlay. In addition, the membrane has at least one port therein so that the volume within the collection chamber is in fluid communication with the volume under the impermeable flexible overlay in the area of the wound. In embodiments where the impermeable flexible overlay has an approximately conical shape or approximately elongated conical shape, the impermeable flexible overlay may have a base end opening and a top end opening opposite the base end opening. In these embodiments, the base end opening may have an either approximately circular shape or approximately elliptical shape sized to be placed over and enclose the area of the wound to be treated. The top end opening may have either an approximately circular shape or approximately elliptical shape. In these embodiments, the membrane is sized to be of the same shape and size as the top end opening and the membrane is positioned so that it is attached to the entire perimeter of the top end opening and covers the entire top end opening.

In some embodiments, the collection chamber may have an approximately conical shape or approximately elongated conical shape with a chamber bottom end opening and a reduced pressure supply port positioned at the apex of the collection chamber opposite the chamber bottom end opening. In various embodiments, the chamber bottom end opening may have an either approximately circular shape or approximately elliptical shape adapted to be of approximately the same size and shape as the top end opening of the impermeable flexible overlay. In some of these embodiments, the perimeter of the chamber bottom end opening is attached to the membrane in a manner so that the collection chamber is airtight, except for the port in the membrane and the reduced pressure supply port. The reduced pressure supply port operably connects the reduced pressure supply means to the collection chamber. In some embodiments, the collection chamber attachment means is further comprised of flow control means operably connected with the at least one port, wherein the flow control means permits fluid aspirated from the wound to flow from the volume under the impermeable flexible overlay in the area of the wound through the at least one port to the collection chamber, but not in the opposite direction. In some of these embodiments, the flow control means is comprised of a valve. Preferably, this valve is comprised of a flapper-type valve.

In another embodiment, the wound treatment appliance is comprised of a wound treatment device and a vacuum system, which is further comprised of a reduced pressure supply source that provides a supply of reduced pressure and reduced pressure supply means to operably connect the wound treatment device to the reduced pressure supply source. In various embodiments, except as described below, the wound treatment device and the reduced pressure supply means may generally have substantially the same structure, features, characteristics and operations as the appliance described above in connection with other embodiments. In these embodiments, the reduced pressure supply means operably connect the wound treatment device to the reduced pressure supply source so that the volume within the collection chamber and under the wound treatment device in the area of the wound is supplied with reduced pressure by the reduced pressure supply source.

In some embodiments, the reduced pressure supply source is comprised of a vacuum pump. In some of these embodiments, the reduced pressure supply source further comprises a control system for the vacuum pump, wherein the control system controls the operation of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments, the reduced pressure supply means is comprised of flexible tubing. In other embodiments, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments, the wound treatment appliance further comprises tissue protection means, which are described in more detail below, to protect and strengthen the body tissue that is adjacent to the flexible overlay at the wound site. In some of these embodiments, the tissue protection means is a hydrocolloid material. In still other embodiments, wound packing means, which are described in more detail herein, are positioned between the wound treatment device and the portion of the wound to be treated.

Another embodiment of the present invention involves a method of treating a wound on a body. In one embodiment, the method comprises the following steps. First, a wound treatment device is positioned on the body over the area of the wound to be treated, wherein the wound treatment device is comprised of an impermeable flexible overlay, a collection chamber, and collection chamber attachment means, which are described in more detail below. In this embodiment, the flexible overlay is sized to be placed over and enclose the area of the wound to be treated and adapted to maintain reduced pressure in the area of the wound to be treated. In addition, in this embodiment, the collection chamber receives and holds fluid aspirated from the wound and the collection chamber attachment means, which is described in more detail below, operably attaches the collection chamber to the impermeable flexible overlay in a manner so that reduced pressure and the fluid are permitted to flow between the collection chamber and the impermeable flexible overlay. Second, the collection chamber is operably connected with a vacuum system for producing reduced pressure in the volume within the collection chamber and in the volume under the flexible overlay in the area of the wound to be treated. Third, the flexible overlay is collapsed in the approximate direction of the wound when reduced pressure is supplied to the volume under the flexible overlay in the area of the wound so that an approximately hermetic seal (described in more detail herein) is formed between the impermeable flexible overlay and the body in the area of the wound. Fourth, reduced pressure is maintained until the area of the wound being treated has progressed toward a selected stage of healing.

In other embodiments, the method further comprises the step of placing tissue protection means on the tissue of the body that is to be approximately adjacent to the impermeable flexible overlay, such step being performed prior to positioning the impermeable flexible overlay over the area of the wound to be treated. The tissue protection means, which is described in more detail below, protects and strengthens the tissue of the body adjacent to the flexible overlay at the wound site. In yet other embodiments of the invention, the method further comprises the step of placing wound packing means (described in more detail herein) between the wound and the impermeable flexible overlay in the area of the wound to be treated, such step being performed prior to positioning the impermeable flexible overlay over the area of the wound to be treated. In still other embodiments, the reduced pressure under the impermeable overlay in the area of the wound is in the range from approximately 20 mm of Hg below atmospheric pressure to approximately 125 mm of Hg below atmospheric pressure. In still other embodiments, the reduced pressure is applied in a cyclic nature, the cyclic nature providing alternating time periods of application of reduced pressure and without application of reduced pressure.

In accordance with one embodiment, a treatment appliance is provided for treating a wound on a body by applying reduced pressure (i.e., pressure that is below ambient atmospheric pressure) to the wound in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In one embodiment, an appliance for treating a wound on a body is comprised of a cover, sealing means to seal the cover to the body, which are described in more detail below, and reduced pressure supply means, which are also described in more detail below. The cover, which is sized to be placed over and enclose the wound, is further comprised of a top cup member, an interface member, and interface attachment means for removably attaching the top cup member to the interface member. The interface member is further comprised of flow control means that permit exudate from the wound to flow from the wound into the top cup member, but not in the opposite direction. Thus, in this embodiment, the interface member is sealed to the body by the sealing means and exudate from the wound flows from the wound through the flow control means in the interface member into the volume of the cover above the interface member. The flow control means do not allow the exudate to flow back into the area of the wound under the interface member. The cover and the sealing means allow reduced pressure to be maintained in the volume under the cover at the site of the wound. The reduced pressure supply means operably connect the cover to a reduced pressure supply source that provides a supply of reduced pressure to the cover, so that the volume under the cover at the site of the wound is supplied with reduced pressure by the reduced pressure supply source.

In some embodiments, the cover may be approximately cylindrical in shape. In other embodiments, the cover may be approximately cup-shaped. In some embodiments, the sealing means may be comprised of the suction of the interface member against the body, such suction being produced by the presence of reduced pressure in the volume under the cover at the site of the wound. In still other embodiments, the top cup member and the interface member are each comprised of materials from the group consisting of semi-rigid materials, rigid materials, and combinations of such materials. Further, in some embodiments, the interface member is further comprised of a membrane portion that is disposed approximately adjacent to the body and the flow control means is comprised of at least one one-way valve operably disposed in the membrane portion. In other embodiments, the interface member may be further comprised of a membrane portion that is disposed approximately adjacent to the body and that permits fluid to flow in only one direction, and the flow control means is comprised of all or a portion of the membrane. In some embodiments, the interface attachment means may be comprised of an o-ring seal or a magnetic seal. In other embodiments, a portion of the interface member may be of a size and shape adapted to fit tightly against a portion of the top cup member, wherein an operable seal (described in more detail below) is created between the interface member and the top cup member. In yet other embodiments, the sealing means may be comprised of an adhesive that is disposed between a portion of the cover and the portion of the body adjacent to said portion of the cover. In still other embodiments, the sealing means may be comprised of an adhesive tape that is disposed over a portion of the cover and the portion of the body adjacent to said portion of the cover. In other embodiments, the top cup member is further comprised of a port and flow shutoff means operably connected to the port, wherein the flow shutoff means halt or inhibit the supply of reduced pressure to the cover when the level of exudate under the cover at the site of the wound reaches a predetermined level. In yet other embodiments, the interface attachment means does not provide for removal of the top cup member from the interface member.

In some embodiments, the top cup member of the cover may be further comprised of a lid member, a cup body member, and lid attachment means to removably attach the lid member to the cup body member. In some of these embodiments, the cover is approximately cylindrical in shape. In other embodiments, the interface attachment means provides for removable attachment of the top cup member to the interface member, but does not provide for permanent attachment of the top cup member to the interface member. In some embodiments, the interface attachment means may be comprised of an o-ring seal or a magnetic seal. In other embodiments, a portion of the interface member may be of a size and shape adapted to fit tightly against a portion of the top cup member, wherein an operable seal is created between the interface member and the top cup member. In still other embodiments, the interface attachment means provides for permanent attachment of the top cup member to the interface member, but does not provide for removable attachment of the top cup member to the interface member. In yet other embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member.

In other embodiments of the present invention, the cover is comprised of a lid member, a cup body member, and lid attachment means to removably attach the lid member to the cup body member. In these embodiments, the cover is sized to be placed over and enclose the wound and adapted to maintain reduced pressure in the volume under the cover at the site of the wound. Also in these embodiments, the sealing means, which are described in more detail below, are used to seal the cup body member of the cover to the body so that reduced pressure may be maintained in the volume under the cover at the site of the wound. Reduced pressure supply means operably connect the cover to a reduced pressure supply source, which provides a supply of reduced pressure to the cover so that the volume under the cover at the site of the wound is supplied with reduced pressure by the reduced pressure supply source. In some embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member. In some embodiments, a portion of the lid member is approximately cylindrical in shape and a portion of the cup body member is approximately cylindrical in shape and said portions have threads and means to receive threads, so that when such portions are screwed together an operable seal is created between the lid member and the cup body member.

In some embodiments, an appliance for administering reduced pressure treatment to a wound on a body is comprised of a treatment device and a vacuum system. In various embodiments, the treatment device is also comprised of a cover and sealing means, which may have substantially the same structure, features, characteristics and operation as the cover and sealing means, respectively, described above in connection with other embodiments of the present invention. In some embodiments, the vacuum system is further comprised of a reduced pressure supply source that provides a supply of reduced pressure and reduced pressure supply means (which are described in more detail below) to operably connect the treatment device to the reduced pressure supply source, so that the volume under the treatment device at the site of the wound is supplied with reduced pressure by the reduced pressure supply source. In various embodiments, the reduced pressure supply means may generally have substantially the same structure, features, characteristics, and operation as the reduced pressure supply means described above in connection with other embodiments of the invention.

In some embodiments, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms or fluids (or both) aspirated from the wound. In yet other embodiments, the vacuum pump is comprised of a portable vacuum pump. In still other embodiments of the invention, the reduced pressure supply means is comprised of flexible tubing. In other embodiments, the cover is further comprised of a port and flow shutoff means, wherein the flow shutoff means halts or inhibits the application of reduced pressure to the cover when exudate from the wound reaches a predetermined level within the cover. In yet other embodiments, the reduced pressure under the cover at the site of the wound is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure.

In some embodiments, an appliance for administering reduced pressure treatment to a wound on a body is comprised of a treatment device and a vacuum system. In various embodiments, the treatment device is also comprised of a cover and sealing means, which may have substantially the same structure, features, characteristics and operation as the cover and sealing means, respectively, described above in connection with other embodiments of the present invention. In various embodiments of the invention, the vacuum system is comprised of a suction bulb, which may (but not necessarily) provide a source of reduced pressure, and reduced pressure supply means, which are described in more detail below, to operably connect the cover to the suction bulb, so that the site of the wound in the volume under the cover may be supplied with reduced pressure by the suction bulb. In some embodiments, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms or fluids (or both) aspirated from the wound. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with other embodiments of the invention.

Another embodiment of the present invention discloses a method of treating a wound. In one embodiment, the method comprises the following steps. First, a cover is positioned on the body over the wound, wherein the cover may have substantially the same structure, features, characteristics and operation as the embodiments of the cover described above in connection with other embodiments of the invention. Second, the cover is operably sealed to the body so that reduced pressure may be maintained in the volume under the cover at the site of the wound. Third, the cover is operably connected with a vacuum system for producing reduced pressure in the volume under the cover at the site of the wound. Fourth, the reduced pressure is maintained until the wound has progressed toward a selected stage of healing.

In other embodiments, the vacuum system is comprised of a suction bulb and the method further comprises the step of squeezing the suction bulb to reduce its volume and then releasing the suction bulb, so that reduced pressure is produced in the volume under the cover at the site of the wound. In other embodiments, the reduced pressure under the cover at the site of the wound is in the range from approximately 20 mm of Hg below atmospheric pressure to approximately 125 mm of Hg below atmospheric pressure. In still other embodiments, the reduced pressure is applied in a cyclic nature, the cyclic nature providing alternating time periods of application of reduced pressure and without application of reduced pressure. In other embodiments, the cover is further comprised of a lid member, a cup body member, and lid attachment means to removably attach the lid member to the cup body member, and the method further comprises the steps of halting the application of reduced pressure to the cover, removing the lid member from the cup body member, and attending to the wound. In some of these embodiments, the method further comprises the steps of re-attaching the lid member to the cup body member after attending to the wound and then reapplying reduced pressure to the volume under the cover in the area of the wound. In still other embodiments, the top cup member further comprises a port and flow shutoff means operably connected to the port, wherein the flow shutoff means halts or hinders the supply of reduced pressure to the volume under the cover in the area of the wound when the level of exudate within the cover reaches a predetermined level. In these embodiments, the method may further comprise the steps of monitoring the level of exudate aspirated from the wound that accumulates within the volume of the cover and removing the cover from the body when the level of exudate aspirated from the wound causes the flow shutoff means to halt or hinder the supply of reduced pressure to the volume under the cover in the area of the wound. It is to be noted that in various other embodiments the steps described above may be performed in a different order than that presented.

Embodiments of the present invention therefore meet the needs discussed above in the Background section. For example, some embodiments of the present invention can eliminate the requirement for a separate collection device to collect exudate from the wound because the exudate is collected and retained within the volume under the cover. In these embodiments, the interface member is sealed to the body by the sealing means and exudate from the wound flows from the wound through the flow control means in the interface member into the volume of the cover above the interface member. The flow control means do not allow the exudate to flow back into the area of the wound under the interface member. Thus, this type of device could reduce the expense involved in wound treatment by eliminating the need for the collection device. This treatment device also removes exudate from the presence of the wound to aid in wound healing. It is also possible for this type of treatment device to be disposable. Further, some embodiments allow for physical access to the wound without the need for removing the treatment device from the body. In these embodiments, the lid member may be removed from the cup body member of the cover, exposing the area of the wound if an interface member is not utilized. This embodiment of the device could enhance patient comfort because it would not be necessary to remove the sealing means to access the wound. In addition, because access is simple and quickly obtained, embodiments of the present invention may also decrease the cost of wound treatment by reducing the time required of healthcare practitioners to be involved in wound treatment. Embodiments of the present invention should also be relatively inexpensive to produce, while meeting the needs described above. As can be observed from the foregoing discussion, embodiments of the present invention have great flexibility. In various embodiments, it may be used with or without the interface member, as well as with or without the removable lid feature.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 3 is a view of an embodiment of a wound treatment appliance of, in which an embodiment of an impermeable flexible overlay, shown in cross-sectional elevational view from the side of the flexible overlay, covers a wound and wound packing means, and in which an embodiment of a vacuum system, shown in elevational view, provides reduced pressure within the area under the flexible overlay;

FIG. 4 is a view of an embodiment of a wound treatment appliance, in which an embodiment of an impermeable flexible overlay, shown in cross-sectional elevational view from the side of the flexible overlay, covers a wound, and in which an embodiment of a vacuum system, shown in perspective view from the side of and below the vacuum system, provides reduced pressure within the area under the flexible overlay;

FIG. 5 is a view of an embodiment of a wound treatment appliance, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay.

DETAILED DESCRIPTION OF THE PREFERRED EMBODIMENTS

Figure 1A:
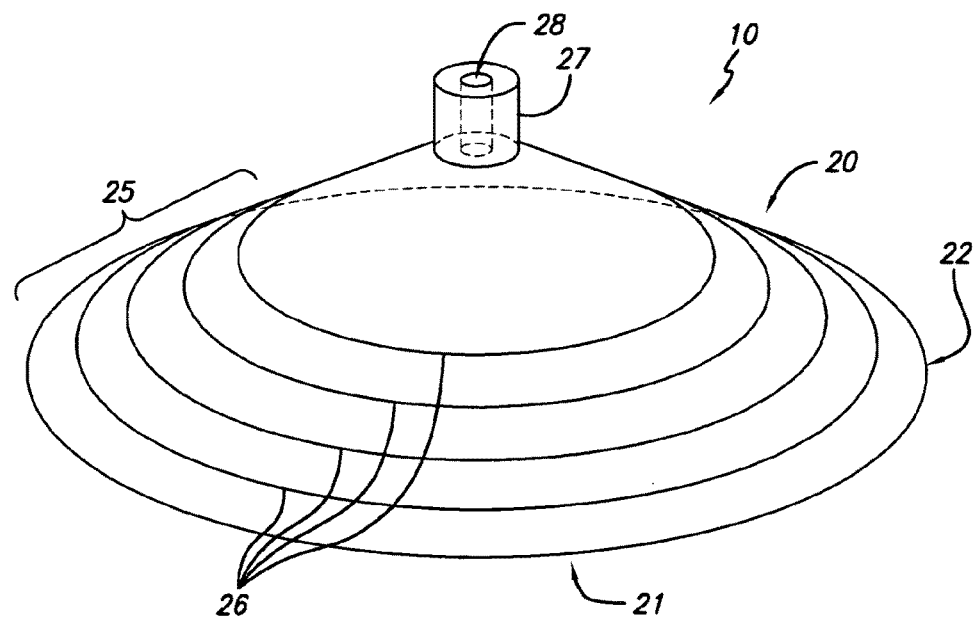
FIG. 1A is a perspective view of an embodiment of an impermeable flexible overlay of a wound treatment appliance, as viewed from the side of and above the flexible overlay comprising the wound treatment appliance (as the flexible overlay would be oriented when placed on the body of a patient)
Figure 1B:
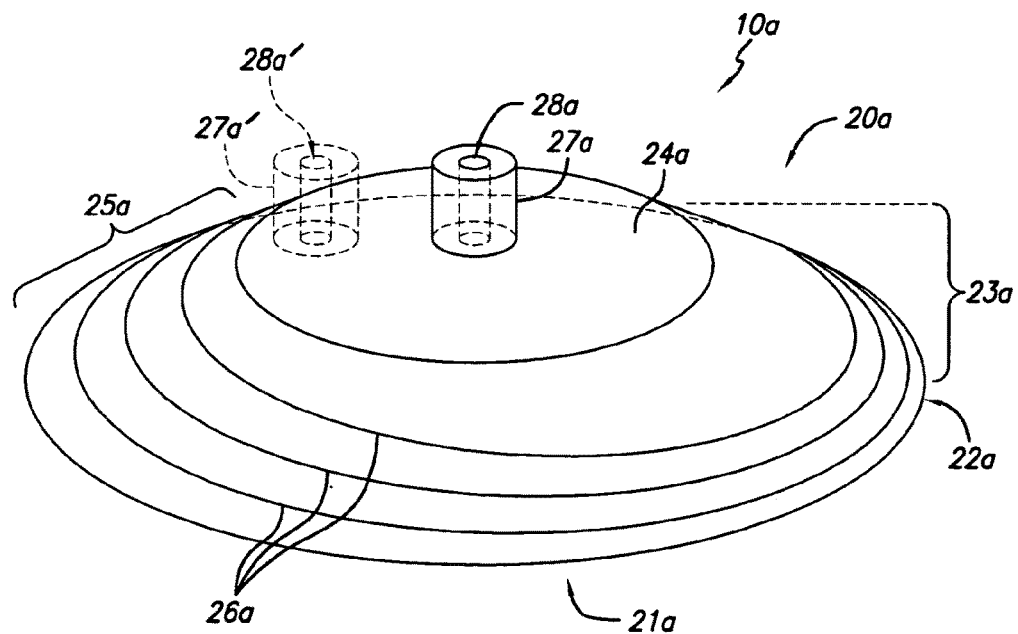
FIG. 1B is a perspective view of another embodiment of an impermeable flexible overlay of a wound treatment appliance, as viewed from the side of and above the flexible overlay comprising the wound treatment appliance (as the flexible overlay would be oriented when placed on the body of a patient)
Figure 1C:
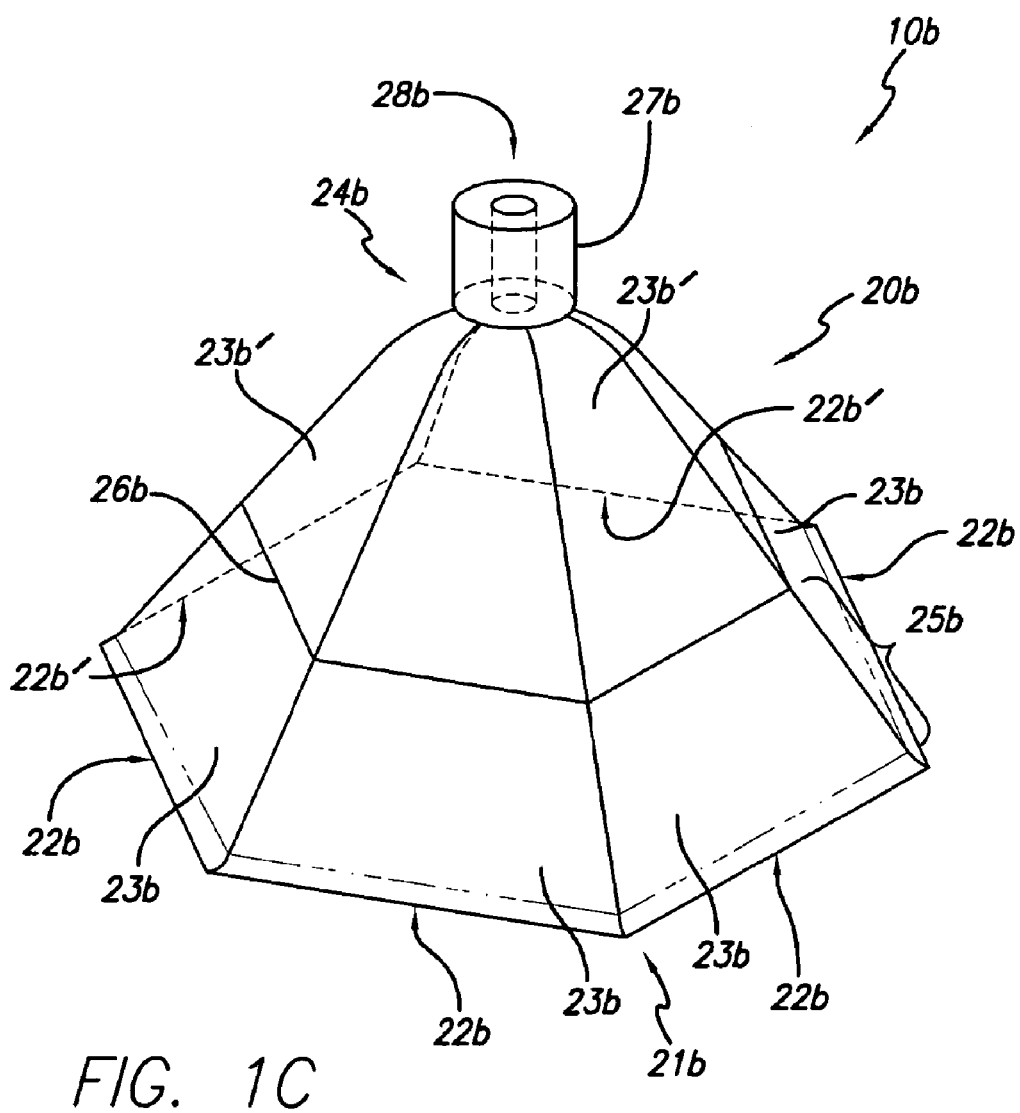
FIG. 1C is a perspective view of another embodiment of an impermeable flexible overlay of a wound treatment appliance, as viewed from the side of and above the flexible overlay comprising the wound treatment appliance (as the flexible overlay would be oriented when placed on the body of a patient)
Figure 1D:
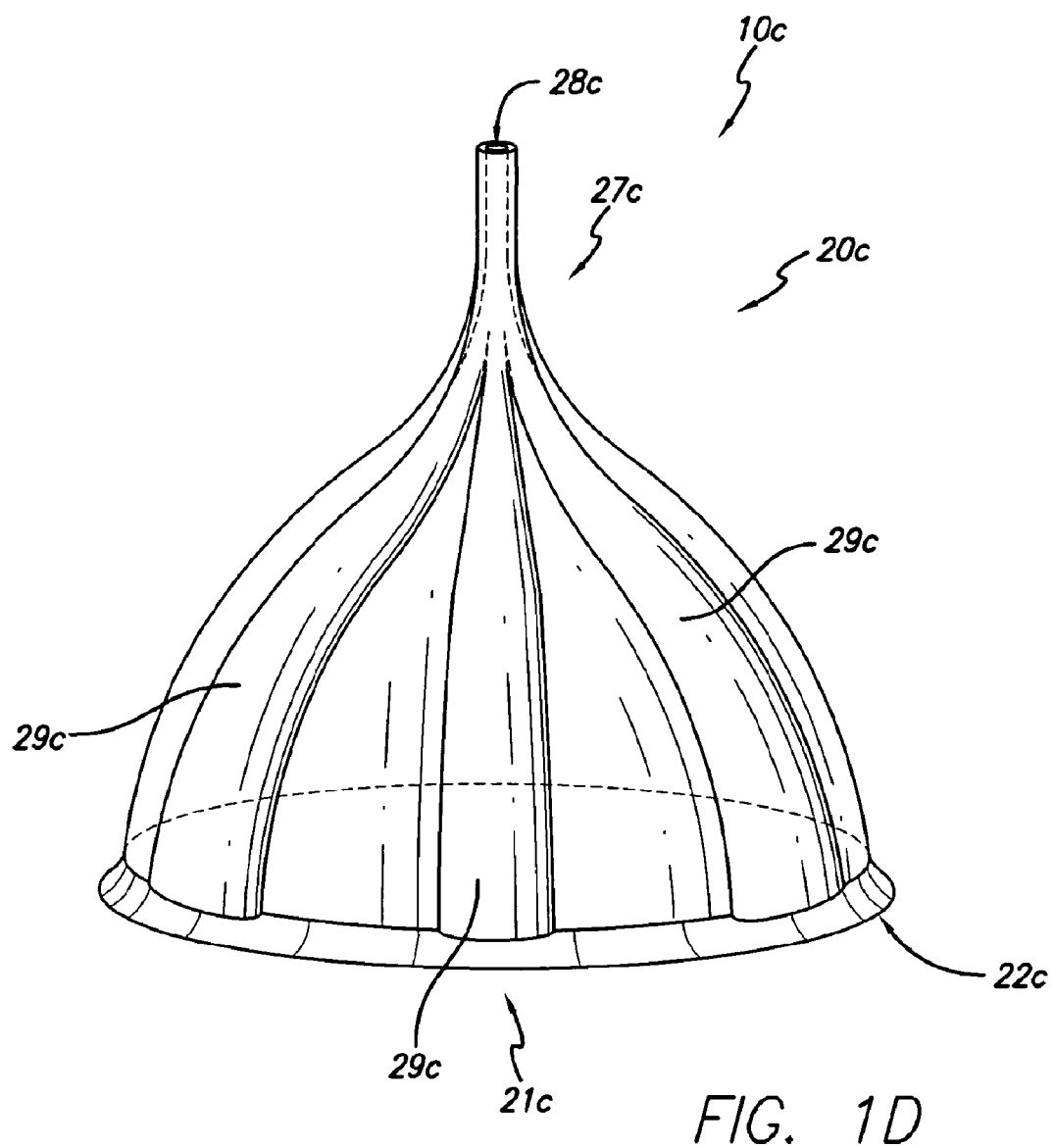
FIG. 1D is a perspective view of another embodiment of an impermeable flexible overlay of a wound treatment appliance, as viewed from the side of and above the flexible overlay comprising the wound treatment appliance (as the flexible overlay would be oriented when placed on the body of a patient)

In accordance with one embodiment of the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. One embodiment is a wound treatment appliance 10 that is comprised of the fluid impermeable flexible overlay 20 illustrated in FIG. 1A and reduced pressure supply means, which are described in more detail below. In this embodiment, the flexible overlay 20 has an approximately elongated conical shape, having an opening 21 with an opening perimeter 22 adjacent to the opening 21 (at the base of the elongated conical shape) that is approximately elliptical in shape. The flexible overlay 20 illustrated in FIG. 1A is in its natural shape, as it exists prior to being applied to a patient for treatment of all or a portion of a wound. In other embodiments, the flexible overlay 20 may have other shapes. For example, the flexible overlay 20 may be approximately conical in shape, rather than the approximately elongated conical shape illustrated in FIG. 1A. As another example, as illustrated in FIG. 1B, only the bottom portion 23a of the flexible overlay 20a may have an approximately elongated conical shape. In this embodiment, and in the same manner as illustrated in FIG. 1A, the bottom portion 23a has an opening 21a with an opening perimeter 22a adjacent to the opening 21a (at the base of the elongated conical shape) that is approximately elliptical in shape. In the embodiment of the flexible overlay illustrated in FIG. 1B, the top portion 24a is flatter than the comparable portion of the flexible overlay 20 in the embodiment illustrated in FIG. 1A. In other embodiments, the top portion 24a of the flexible overlay 20a may have almost any shape that is adaptable to a bottom portion 23a having an approximately elongated conical shape. In addition, in yet other embodiments of the invention, the bottom portion 23a of the flexible overlay 20a may be in the approximate shape of a cone, rather than the elongated conical shape illustrated in FIG. 1B. In yet another embodiment, as illustrated in FIG. 1C, the flexible overlay 20b is comprised of six cover portions 23b, 23b', where the cover portions 23b are viewable in FIG. 1C and the cover portions 23b' are illustrated by phantom lines. In this embodiment, each of such cover portions 23b, 23b' is approximately triangular in shape, and one point of each of the at least three cover portions 23b, 23b' is joined to form an apex 24b of the impermeable flexible overlay 20b. One side of each cover portion 23b, 23b' adjacent to the apex 24b is joined to an adjacent side of another of such cover portions 23b, 23b' so that the bases 22b, 22b' of the cover portions 23b, 23b', respectively, form an opening 21b sized to be placed over and enclose the area of the wound to be treated. In other embodiments, the flexible overlay 20b may have a different number of cover portions 23b, 23b'. Preferably, in these embodiments, there are at least three cover portions 23b, 23b'. In addition, in yet other embodiments, the flexible overlay 20b may have cover portions 23b, 23b' having a different shape, such as trapezoidal or parabolic. Another embodiment of the present invention is illustrated in FIG. 1D. In this embodiment, the overlay 20c is approximately cup-shaped with an approximately circular opening 21c, which has an opening perimeter 22c adjacent to the opening 21c. The overlay 20c of this embodiment also has a plurality of channels 29c disposed in the surface thereof as suction assist means, which are described in more detail below. In still other embodiments, the flexible overlay 20, 20a, 20b, 20c may be of almost any shape that may be adaptable for treating all or a portion of a wound, as long as the flexible overlay 20, 20a, 20b, 20c is flexible, as described in more detail below, and the interior surface of the flexible overlay 20, 20a, 20b, 20c is adapted to make an approximately hermetic seal with the body of the patient at the site of the wound, as described in more detail below. For example, and as clarification, the flexible overlay 20, 20a, 20b, 20c or portions thereof may have an approximately tetrahedral, hexahedral, polyhedral, spherical, spheroidal, arcuate, or other shape or combination of all such shapes. Referring again to FIG. 1A as an example, in some embodiments, the interior surface of the flexible overlay 20 is adapted to make an approximately hermetic seal with the body of the patient at the site of the wound by having a surface area larger than the surface area of the portion of the body of the patient covered by the flexible overlay 20, as described in more detail below.

The preferred shape and size of the flexible overlay 20, 20a, 20b, 20c is dependent upon the size of the portion of the wound to be treated, the shape and contour of the portion of the body that is to be covered by the flexible overlay 20, 20a, 20b, 20c at the site of the wound, the magnitude of the reduced pressure to be maintained under the flexible overlay 20, 20a, 20b, 20c. More preferred, as illustrated in FIG. 1B, the flexible overlay 20a has an approximately elongated conically shaped bottom portion 23a. Most preferred, as illustrated in FIG. 1A, the flexible overlay 20 is shaped approximately as an elongated cone. The preferred thickness of the portion 25, 25a, 25b, 20c of the flexible overlay 20, 20a, 20b, 20c adjacent to the open end 21, 21a, 21b, 20c of the flexible overlay 20, 20a, 20b, 20c is dependent upon the size and shape of the flexible overlay 20, 20a, 20b, 20c, the shape and contour of the portion of the body that is to be covered by the flexible overlay 20, 20a, 20b, 20c at the site of the wound, the magnitude of the reduced pressure to be maintained under the flexible overlay 20, 20a, 20b, 20c, and other factors, such as the depth of the wound and the amount of the desired collapse of the flexible overlay 20, 20a, 20b, 20c. For example, in the embodiment illustrated in FIG. 1A, for a flexible overlay 20 constructed of silicone and having an approximately elongated conical shape with an opening 21 having a major diameter of approximately 7 inches and a minor diameter of approximately 4 inches, the preferred thickness of the portion 25 of the flexible overlay 20 adjacent to the open end 21 of the flexible overlay 20 is in the range from $\frac{1}{32}$ inches to $\frac{3}{32}$ inches. More preferred in this embodiment, the thickness of the portion 25 of the flexible overlay 20 adjacent to the open end 21 of the flexible overlay 20 is approximately $\frac{1}{16}$ inches. It is to be noted that in other embodiments the thickness of the flexible overlay 20, including the portion 25 of the flexible overlay 20 adjacent to the open end 21 of the flexible overlay 20, may vary from location to location on the flexible overlay 20.

In the embodiment of the flexible overlay 20 illustrated in FIG. 1A, the flexible overlay 20 has a series of raised beads 26 on the outside surface of the flexible overlay 20. In this embodiment, the raised beads 26 are generally parallel to the perimeter 22 of the opening 21 of the flexible overlay 20. The same is also true of the raised bead 26b of the flexible overlay 20b of the embodiment illustrated in FIG. 1C. In other embodiments, such as that illustrated in FIG. 1B, the raised beads 26a may have a different orientation. In still other embodiments, the raised beads 26, 26a, 26b may be in almost any orientation desired by the user of the wound treatment appliance 10, 10a, 10b. In various embodiments, as illustrated in FIG. 1A, the raised beads 26 may provide a guide for the user administering the reduced pressure treatment to cut away a portion of the flexible overlay 20, so that the perimeter 22 of the opening 21 of the flexible overlay 20 is smaller than it was originally. For example, by cutting along the parallel raised beads 26 of the flexible overlay 20 of FIG. 1A, the size of the opening 21 of the flexible overlay 20 can be made smaller while the shape of the perimeter 22 remains approximately the same. It is to noted, however, that in various embodiments of the invention, as described in more detail below, the flexible overlay 20 may be cut into different shapes in order to adapt the flexible overlay 20 for use with different shapes and contours of the surface of the body at the site of the wound.

In other embodiments of the present invention, as illustrated in FIG. 1D, the flexible overlay 20c may be further comprised of suction assist means to assist in the application of reduced pressure to the portion of the wound to be treated, as well as removal of exudate from the wound. For example, in the illustrated embodiment, the overlay 20c has a plurality of channels 29c disposed in the surface thereof. The channels 29c may generally provide a conduit for reduced pressure to reach the various portions of the wound to be treated. In addition, exudate aspirated from the various portions of the wound to be treated may flow along the channels 29c to the reduced pressure supply means (not illustrated), where the exudate may be removed from the flexible overlay 20c by means of the reduced pressure supply means cooperating with the reduced pressure supply source, as described in more detail below. In some of these embodiments, the channels 29c may be operably connected to the reduced pressure supply means through a port 27c, as described in more detail below. In the illustrated embodiment, there are three continuous channels 29c recessed into the surface of the overlay 20c, which are joined together near the apex of the flexible overlay 20c at the port 27c. In other embodiments, there may be more or fewer channels 29c. For example, in other embodiments, there may be fewer channels 29c and the channels 29c may be of the same size or of a different size. In yet other embodiments, there may be many channels 29c, in which case the channels 29c may generally be of a smaller size. In addition, the channels 29c may be disposed in other positions relative to the flexible overlay 20c. For example, the channels 29c may be located at different locations on the flexible overlay 20c and may have a different orientation, such as being curved in a "corkscrew" pattern or crossed in a "checkerboard" pattern, rather than being oriented as illustrated in FIG. 1D. In still other embodiments, the channels 29c, as suction assist means, may have a different structure and form. For example, the channels 29c may be in the form of tubes positioned within the volume of the flexible overlay 20c, wherein the tubes have one or more perforations so that the channels 29c are in fluid communication with the volume under the flexible overlay 20c in the area of the wound to be treated. As another example, the channels 29c may have stiffening members, such as raised beads ("ribs") of material, so that the channels 29c have a greater stiffness than the remaining portions of the flexible overlay 20c. In other embodiments, the channels 29c, as suction assist means, may be in the form of portions that are raised above the surface of the flexible overlay 20c. Such raised portions may appear as "dimples" when viewed from above the flexible overlay 20c. The channels 29c, as suction assist means, may also be of almost any size, shape and pattern to accomplish their intended purpose. The preferred size, shape and pattern are dependent upon the size and shape of the flexible overlay 20c, the type of wound to be treated, the level of reduced pressure to be used in the treatment, the amount of exudate anticipated, the type of reduced pressure supply means utilized, and the individual preference of the user of the appliance 10c. Where utilized, channels 29c may be molded or cut into the surface of the flexible overlay 20c or, if in the shape of tubes, may be molded as a part of the surface of the flexible overlay 20c or may be welded or fused to the surface of the flexible overlay 20c. It is to be noted that the various embodiments of the flexible overlays 20, 20a, 20b illustrated and described above in connection with FIG. 1A, FIG. 1B, and FIG. 1C, respectively, may each also comprise suction assist means, and therefore may also comprise any of the various embodiments of the channels 29c illustrated and described above in connection with FIG. 1D.

In various embodiments, the flexible overlay 20, 20a, 20b, 20c may be comprised of almost any medical grade flexible material that is currently known in the art or that may be developed in the art in the future, as long as such material is fluid-impermeable, suitable for purposes of wound treatment (e.g., can be sterilized and does not absorb significant amounts of wound exudate), and is capable of forming an approximately hermetic seal with the surface of the body at the site of the wound, as described in more detail below. For example, the flexible overlay 20, 20a, 20b, 20c may be comprised of rubber (including neoprene), and flexible polymer materials, such as silicone, silicone blends, silicone substitutes, polyester, vinyl, polyimide, polyethylene napthalate, polycarbonates, polyester-polycarbonate blends, or a similar polymer, or combinations of all such materials. Preferably, the flexible overlay 20, 20a, 20b, 20c is comprised of silicone. Although the raised beads 26, 26a, 26b may be constructed of a material different from the material comprising the remainder of the flexible overlay 20, 20a, 20b in various embodiments of the invention, the raised beads 26, 26a, 26b are preferably constructed from the same material comprising the remainder of the flexible overlay 20, 20a, 20b. In other embodiments, the raised beads 26, 26a, 26b may be placed on the flexible overlay 20, 20a, 20b by means of a mark, such as indelible ink, on the surface of the flexible overlay 20, 20a, 20b. In some embodiments, the channels 29c (and all other suction assist means) may be constructed of a material different from the material comprising the remainder of the flexible overlay 20c. For example, one or more of the channels 29c may be constructed of a slightly more rigid material than the remainder of the flexible overlay 20c so that such channel 29c or channels 29c better retain their shape. In other embodiments, the channels 29c may be constructed of the same material comprising the remainder of the flexible overlay 20c, but the channels 29c may have a different thickness than the remainder of the flexible overlay 29c. For example, one or more of the channels 29c may be slightly thicker than the remainder of the flexible overlay 20c so that such channel 29c or channels 29c better retain their shape. In still other embodiments, the channels 29c may be constructed of the same material comprising, and have the same thickness as, the remainder of the flexible overlay 20c. Preferably, the channels 29c are constructed of the same material as, but have a slightly greater thickness than, the remaining portions of the flexible overlay 20c. It is to be noted that in various embodiments of the invention, the flexible overlay 20, 20a, 20b, 20c may be constructed in whole or in part of gas-permeable materials, allowing limited amounts of oxygen to penetrate the flexible overlay 20, 20a, 20b, 20c so that the area of the wound under the flexible overlay 20, 20a, 20b, 20c can "breathe." It is also to be noted that all portions of the flexible overlay 20, 20a, 20b, 20c are preferably constructed of one type of polymer material, such as silicone. The flexible overlay 20, 20a, 20b, 20c may be constructed using any suitable means currently known in the art or that may be developed in the art in the future. For example, a flexible overlay 20, 20a, 20b, 20c constructed of silicone may be manufactured by means of injection molding. As another example, where the channels 29c are constructed of a different material from the remainder of the flexible overlay 20c, the channels 29c may be welded or fused to the remaining portions of the flexible overlay 20c.

In the embodiments of the flexible overlay 20, 20a, 20b, 20c illustrated in FIG. 1A, FIG. 1B, FIG. 1C, and FIG. 1D, respectively, each of the flexible overlays 20, 20a, 20b, 20c further comprises a port 27, 27a, 27b, 27c adapted to receive a reduced pressure supply means to supply reduced pressure to the area of the wound under the flexible overlay 20, 20a, 20b, 20c. Although the port 27 is positioned at approximately the apex of the elongated cone-shaped flexible overlay 20 in the embodiment illustrated in FIG. 1A, and the port 27b is positioned at approximately the apex 24b of the triangular-shaped cover portions 23b, 23b' in the embodiment illustrated in FIG. 1C, which is the preferred location, the port may be located at another location on the flexible overlay in other embodiments. In such embodiments, and referring to FIG. 1B as an example, the port 27a (and alternate port 27a') may be located at almost any location on the surface of the flexible overlay 20a as long as the port 27a, 27a' does not adversely affect the ability of the flexible overlay 20a to make an approximately hermetic seal with the surface of the body at the wound site, as described in more detail below. For example, the port 27a, 27a' may not be located too close to the perimeter 22a of the opening 21a of the flexible overlay 20a because the approximately hermetic seal with the surface of the body is typically formed at that location. In the embodiment of the flexible overlay 20a illustrated in FIG. 1B, the alternate port 27a' may preferably be located at any location on the top portion 24a of the flexible overlay 20a, and more preferably, the port 27a is located at the center of the top portion 24a of the flexible overlay 20a. Referring again to FIG. 1A as an example, although the port 27 may be constructed of a material different from the material comprising the remainder of the flexible overlay 20 in various embodiments of the invention, the port 27 is preferably constructed from the same material comprising the remainder of the flexible overlay 20. In the embodiments of the flexible overlay 20, 20a, 20b illustrated in FIG. 1A, FIG. 1B, and FIG. 1C, respectively, the ports 27, 27a, 27b are generally cylindrical in shape and are further comprised of an approximately cylindrical duct 28, 28a, 28a', 28b, respectively, that extends from the top of each of the ports 27, 27a, 27b, respectively, to the bottom of the ports 27, 27a, 27b, respectively. The ports 27, 27a, 27b of these embodiments are thus able to receive a vacuum system or reduced pressure supply means, which are described in more detail below, adapted to be connected to this shape of port 27, 27a, 27b, respectively, and channel 28, 28a, 28a' 28b, respectively. In other embodiments of the invention, the ports 27, 27a, 27b, 27c or the port ducts 28, 28a, 28a' 28b, respectively, or both may have different shapes and configurations as may be desired to adapt and connect the ports 27, 27a, 27b, respectively, and the port ducts 28, 28a, 28a' 28b, respectively, to the vacuum system or reduced pressure supply means, which are described in more detail below. For example, the port 27c of the flexible overlay 20c illustrated in FIG. 1D is formed as a single piece with the remainder of the flexible overlay 20c. In this example, the port 27c has a cylindrical duct 28c that extends through the port 27c and generally follows the contours of the channels 29c at its lower end.

Figure 2A:
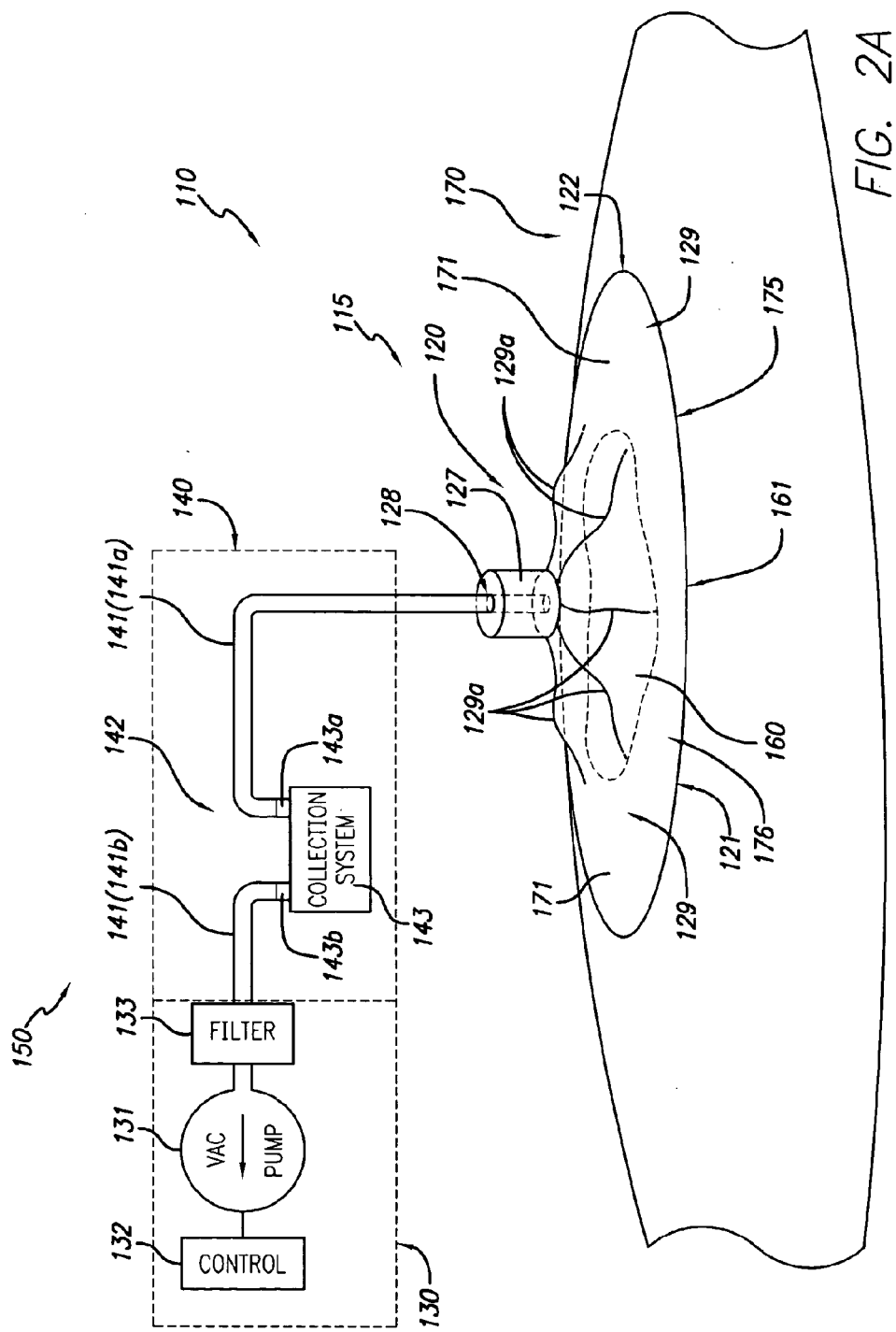
FIG. 2A is a view of an embodiment of a wound treatment appliance, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay.

Another embodiment of the present invention is the wound treatment appliance 110 illustrated in FIG. 2A. In this embodiment, the wound treatment appliance 110 is comprised of a wound treatment device 115 and a vacuum system, generally designated 150, that is operably connected to, and provides a supply of reduced pressure to, the wound treatment device 115. Also in this embodiment, the wound treatment device 115 is comprised of a flexible overlay 120. In addition, in this embodiment, the vacuum system 150 is further comprised of a reduced pressure supply source, generally designated 130, which is illustrated schematically and described in more detail below, and reduced pressure supply means, generally designated 140, which are illustrated schematically and described in more detail below. Also in this embodiment, the reduced pressure supply means 140 are used to connect the reduced pressure supply source 130 to the flexible overlay 120 in a manner so that reduced pressure is supplied to the volume under the flexible overlay 120 in the area of the wound 160, as described in more detail below. In the embodiment illustrated in FIG. 2A, the flexible overlay 120 has substantially the same structure, features, characteristics and operation as the flexible overlay 20 described above and illustrated in connection with FIG. 1A. It is to be noted, however, that in other embodiments, the flexible overlay 120 may have substantially the same structure, features and characteristics as any embodiment of all of the flexible overlays 20, 20a, 20b, 20c of the embodiments described above and illustrated in connection with FIG. 1A, FIG. 1B, FIG. 1C, and FIG. 1D. FIG. 2A also illustrates an example of how the embodiment of the flexible overlay 20 illustrated in FIG. 1A may be used to provide reduced pressure treatment for a wound 160 on the body 170 of a patient. In this example, the flexible overlay 120 is placed over and encloses the entire wound 160, as described in more detail below. In other embodiments, the flexible overlay 120 need not enclose the entire wound 160.

In the embodiment illustrated in FIG. 2A, the reduced pressure supply source 130 of the vacuum system 150, which produces a source of reduced pressure or suction that is supplied to the flexible overlay 120, is comprised of a vacuum pump 131, a control device 132, and a filter 133. Although the preferred means of producing the reduced pressure or suction is a vacuum pump 131 in this embodiment, in other embodiments of the invention other means may be used, such as an outlet port of a centralized hospital vacuum system. In the illustrated embodiment, predetermined amounts of suction or reduced pressure are produced by the vacuum pump 131. The vacuum pump 131 is preferably controlled by a control device 132, such as a switch or a timer that may be set to provide cyclic on/off operation of the vacuum pump 131 according to user-selected intervals. Alternatively, the vacuum pump 131 may be operated continuously without the use of a cyclical timer. In addition, in some embodiments the control device 132 may provide for separate control of the level of reduced pressure applied to the wound 160 and the flow rate of fluid aspirated from the wound 160. In these embodiments, relatively low levels of reduced pressure may be maintained in the area of the wound 160 under the wound treatment device 115, while still providing for the removal of a relatively large volume of exudate from the wound 160. A filter 133, such as a micropore filter, is preferably attached to the inlet of the vacuum pump 131 to prevent potentially pathogenic microbes or aerosols from contaminating, and then being vented to atmosphere by, the vacuum pump 131. In other embodiments, the filter 133 may also be a hydrophobic filter that prevents any exudate from the wound from contaminating, and then being vented to atmosphere by, the vacuum pump 131. It is to be noted that in other embodiments of the invention, the reduced pressure supply source 130 may not have a filter 133 or a control 132 or any combination of the same.

In the embodiment illustrated in FIG. 2A, the reduced pressure supply means 140 of the vacuum system 150, which are used to connect the reduced pressure supply source 130 to the flexible overlay 120 so that reduced pressure is supplied to the volume under the flexible overlay 120 in the area of the wound 160 is comprised of at least one tubing member 141. In this embodiment, the at least one tubing member 141 is sufficiently flexible to permit movement of the at least one tubing member 141, but is sufficiently rigid to resist constriction when reduced pressure is supplied to the flexible overlay 120 or when the location of the wound 160 is such that the patient must sit or lie upon the at least one tubing member 141 or upon the wound treatment device 115. In the embodiment illustrated in FIG. 2A, the at least one tubing member 141 is connected to the flexible overlay 120 by inserting one end of the at least one tubing member 141 into the opening 128 of the port 127 of the flexible overlay 120. In this embodiment, the at least one tubing member is held in place in the opening 128 by means of an adhesive. It is to be noted that in other embodiments of the invention, the at least one tubing member 141 may be connected to the port 127 of the flexible overlay 120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 127 and the at least one tubing member 141 may be fabricated as a single piece, as is the case with the port 27c of the flexible overlay 20c, as illustrated and described above in connection with FIG. 1D. Similar means may be used to connect the other end of the at least one tubing member 141 to the vacuum pump 131 or other reduced pressure supply source 130 providing the reduced pressure.

Figure 2B:
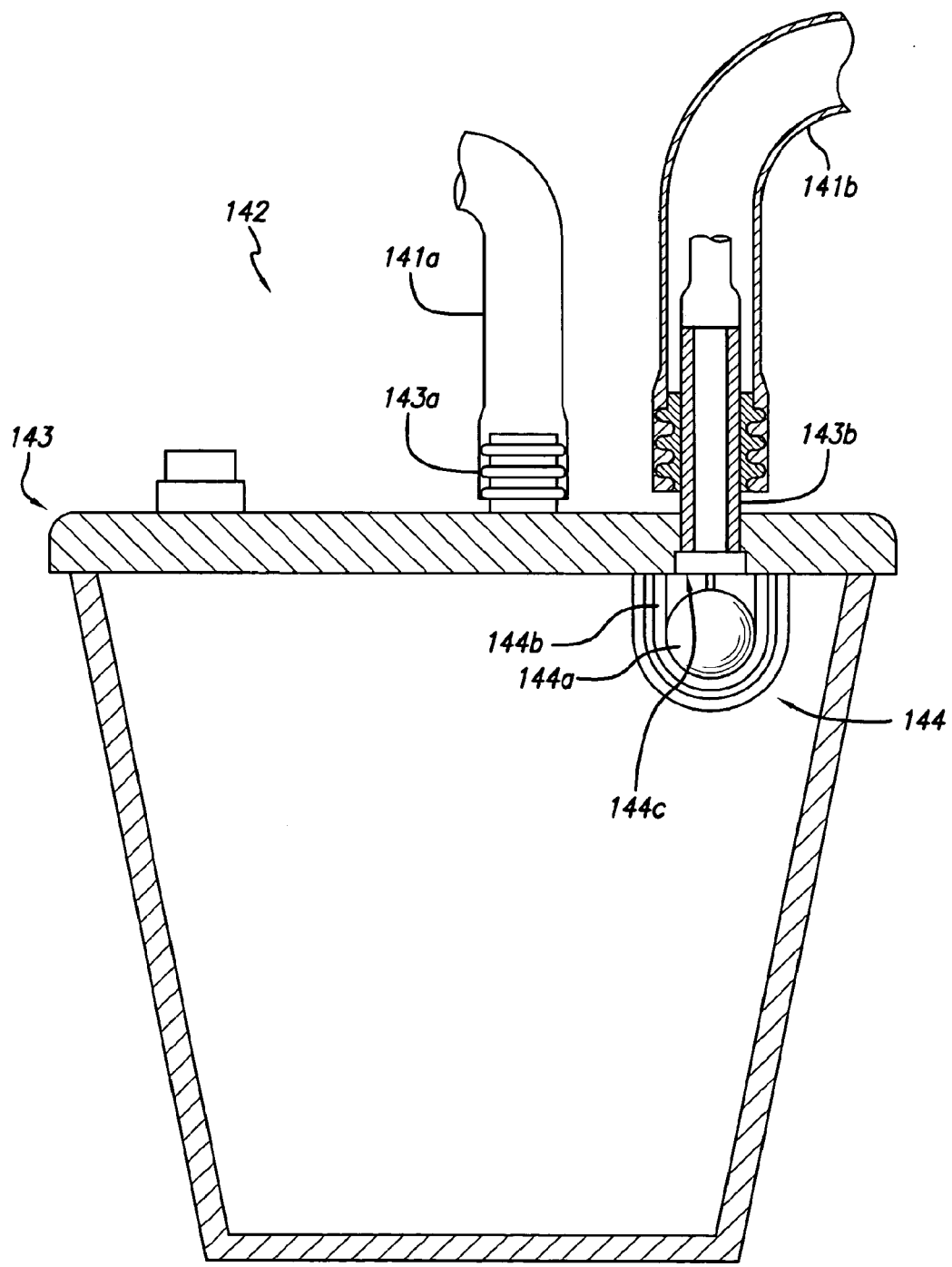
FIG. 2B is a sectional elevational detailed view of an embodiment of a collection container and the shutoff mechanism portion of the collection system of FIG. 2A.

In the embodiment illustrated in FIG. 2A, the reduced pressure supply means 140 further comprises a fluid collection system, generally designated 142, that is interconnected between the suction pump 131 and the flexible overlay 120 to remove and collect any exudate that may be aspirated from the wound 160 and collected by the flexible overlay 120. The flexible overlay 120 functions to actively draw fluid or exudate from the wound 160. Collection of exudate in a fluid collection system 142 intermediate the pump 131 and the flexible overlay 120 is desirable to prevent clogging of the pump 131. The fluid collection system 142 is comprised of a fluid-impermeable collection container 143 and a shutoff mechanism 144, which are described in more detail below in connection with FIG. 2B. The container 143 may be of any size and shape capable of intercepting and retaining a predetermined amount of exudate. Many examples of such containers are available in the relevant art. Referring to FIG. 2B, which is an enlarged elevational cross-sectional view of the preferred embodiment of the container 143, the container 143 includes a first port 143a at the top opening of the container 143 for sealed connection to tubing member 141a, where the other end of the tubing member 141a is connected to the flexible overlay 120. The first port 143a enables suction to be applied to the flexible overlay 120 through the tubing 141a and also enables exudate from the portion of the wound 160 covered by the flexible overlay 120 to be drained into the container 143. The container 143 provides a means for containing and temporarily storing the collected exudate. A second port 143b is also provided on the top of the container 143 to enable the application of suction from the vacuum pump 131. The second port 143b of the collection system 142 is connected to the vacuum pump 131 by tubing member 141b. The collection system 142 is sealed generally gas-tight to enable the suction pump 131 to supply suction to the flexible overlay 120 through the collection system 142.

The embodiment of the collection system 142 illustrated in FIG. 2B also includes a shutoff mechanism for halting or inhibiting the supply of the reduced pressure to the flexible overlay 120 in the event that the exudate aspirated from the wound 160 exceeds a predetermined quantity. Interrupting the application of suction to the flexible overlay 120 is desirable to prevent exsanguination in the unlikely event a blood vessel ruptures under the flexible overlay 120 during treatment. If, for example, a blood vessel ruptures in the vicinity of the wound 160, a shut-off mechanism would be useful to prevent the vacuum system 150 from aspirating any significant quantity of blood from the patient. In one embodiment of the shutoff mechanism 144, as illustrated in FIG. 2B, the shutoff mechanism 144 is a float valve assembly in the form of a ball 144a which is held and suspended within a cage 144b positioned below a valve seat 144c disposed within the opening at the top of the container below the second port 143b that will float upon the exudate and will be lifted against the valve seat 144c as the container 143 fills with exudate. When the ball 144a is firmly seated against the valve seat 144c, the float valve blocks the second port 143b and thereby shuts off the source of suction from the vacuum system 150. In other embodiments of the container 143, other types of mechanisms may also be employed to detect the liquid level within the container 143 in order to arrest operation of the vacuum system 50. In addition, in various embodiments, the shutoff mechanism 144 may be comprised of any means that enables the vacuum system 150 to halt the supply of reduced pressure to the flexible overlay 120 at any time that the volume of exudate from the wound 160 exceeds a predetermined amount. Such means may include mechanical switches, electrical switches operably connected to the vacuum system controller 132, optical, thermal, or weight sensors operably connected to the vacuum system controller 132, and any other means that are currently known in the relevant art or that may be developed in the art in the future.

In some embodiments, the wound treatment appliance 110 further comprises tissue protection means 175 to protect and strengthen the body tissue 171 that is adjacent to the flexible overlay 120 at the wound site 161. The tissue protection means 175 protects the tissue 171 by preventing abrasion and maceration of the tissue. Preferably, the tissue protection means 175 is a hydrocolloid material, such as COLOPAST Hydrocolloid 2655, anhydrous lanoline, or any combination of such hydrocolloid materials. More preferably, the tissue protection means 175 is COLOPAST Hydrocolloid 2655. The tissue protection means 175 may be applied to the body tissue 171 to be protected, or it may be applied to the surface of the flexible overlay 120 that is to be in contact with the body tissue 171, or both, prior to placing the flexible overlay 120 on the surface of the body 170 at the wound site 161. It is to be noted that application of the tissue protection means 175 to the body tissue 171 that is adjacent to the flexible overlay 120 at the wound site 161 may only entail application of the tissue protection means 175 to the portion of the body tissue 171 adjacent to the flexible overlay 120 that requires such protection.

FIG. 2A also illustrates an example of how the embodiment of the flexible overlay 20 illustrated in FIG. 1A (which is flexible overlay 120 in FIG. 2A) may be used to provide reduced pressure treatment for a wound 160 on the body 170 of a patient. In this example, the flexible overlay 120 is removed from an aseptic package in which it is stored. The flexible overlay 120 is then placed over and encloses the portion of the wound 160 to be treated, which is the entire wound 160 in this example. The flexible overlay 120 is also connected to the vacuum system 150 by means of the port 127 on the flexible overlay 120 either before, after or during the placement of the flexible overlay 120 over the wound 160. Where it is deemed necessary by the user of the wound treatment appliance 110, tissue protection means 175, as described above, may be placed on a portion of the flexible overlay 120, on the body tissue 171 to be protected, or both, prior to placing the flexible overlay 120 over the wound 160. In the example illustrated in FIG. 2A, the interior surface portions 129 of the flexible overlay 120 positioned around and adjacent to the perimeter 122 of the opening 121 of the flexible overlay 120 are at (or can be deformed to be at) a relatively acute angle relative to the surrounding surface of the body 170. Such deformation may be caused by the user of the wound treatment appliance 110 exerting mild pressure on the portions 129 of the flexible overlay 120 positioned around and adjacent to the perimeter 122 of the opening 121 of the flexible overlay 120 so that they are in contact with the surface of the body 170 surrounding the wound 160. Reduced pressure is then supplied to the flexible overlay 120 by the vacuum system 150. When reduced pressure is applied to the volume under the flexible overlay 120 in the area of the wound 160, the flexible overlay 120 is drawn downward by the reduced pressure, collapsing the flexible overlay 120 in the approximate direction of the wound 160. As the flexible overlay 120 collapses, the portions 129 of the flexible overlay 120 adjacent to the perimeter 122 of the opening 121 of the flexible overlay 120 are drawn tightly against the surface of the body 170 surrounding the wound 160, thus forming an approximately hermetic seal between the portions 129 of the flexible overlay 120 adjacent to the perimeter 122 of the opening 121 of the flexible overlay 120 and the portion of the body 170 adjacent to such portions 129. References to an "approximately hermetic seal" herein refer generally to a seal that may be made gas-tight and liquid-tight for purposes of the reduced pressure treatment of the wound 160. It is to be noted that this seal need not be entirely gas-tight and liquid-tight. For example, the approximately hermetic seal may allow for a relatively small degree of leakage, so that outside air may enter the volume under the flexible overlay 120 in the area of the wound 160, as long as the degree of leakage is small enough so that the vacuum system 150 can maintain the desired degree of reduced pressure in the volume under the flexible overlay 120 in the area of the wound 160. As another example, the approximately hermetic seal formed by the collapsing flexible overlay 120 may not be solely capable of maintaining the reduced pressure in the volume under the flexible overlay 120 in the area of the wound 160. This may be the case if the shape of the body 170 at the site of the wound 160 does not allow for such a seal. In other instances, as may be the case with the flexible overlay 20c illustrated and described above in connection with FIG. 1D, the perimeter 22c adjacent to the opening 21c may not have a relatively acute angle relative to the surrounding tissue, so that additional means is required to make an approximately hermetic seal. In these cases, it may be necessary to provide supplemental sealing means, which are used to provide a seal between the portions of the flexible overlay 120 and the body 170 where the approximately hermetic seal is not adequate to permit reduced pressure to be maintained in the volume under the flexible overlay 120 in the area of the wound 160. For example, in the illustrated embodiment, the supplemental sealing means 176 may be an adhesive applied to a portion of the impermeable overlay 120 or a portion of the body 170 in a manner similar to the application of the tissue protection means 175 described above. In other embodiments, the supplemental sealing means 176 may be comprised of almost any suitable means to provide an adequate seal. For example, the supplemental sealing means 176 may be comprised of an adhesive, an adhesive tape, a stretch fabric that covers the wound treatment device 115 and is wrapped around a portion of the body 170 of the patient in the area of the wound 160, lanoline, or any combination of such means. It is also to be noted that in this embodiment at least one fold 129a forms in the surface of the flexible overlay 120 when it collapses, so that exudate aspirated by the wound 160 flows along the at least one fold 129a to the port 127, where the exudate is removed from the flexible overlay 120 by means of the reduced pressure supply means 140 cooperating with the reduced pressure supply source 130. Thus, in some embodiments, the impermeable overlay 120 is constructed of a material, and has a size, shape and thickness, that permits the flexible overlay 120 to collapse in the direction of the wound 160 and form an approximately hermetic seal with the body 170 when reduced pressure is applied to the volume under the flexible overlay 120 in the area of the wound 160, while still being rigid enough to support the approximately hermetic seal with the body 170 and to support the at least one fold 129a. In embodiments of the overlay 120 comprising suction assist means, such as the channels 29c of the flexible overlay 20c illustrated and described above in connection with FIG. 1D, exudate from the wound 160 may also flow along such channels to the port 127. It is also to be noted that the volume under the flexible overlay 120 in the area of the wound 160 may be minimal while the flexible overlay 120 is in its collapsed state over the wound 160. In some embodiments, the reduced pressure maintained in the volume under the flexible overlay 120 in the area of the wound 160 is in the range from approximately 20 mm of Hg below atmospheric pressure to approximately 125 mm of Hg below atmospheric pressure. In yet other embodiments, the reduced pressure is applied to the flexible overlay 120 in a cyclic nature, the cyclic nature providing alternating time periods of application of reduced pressure and non-application of reduced pressure. In all of these embodiments, the reduced pressure is maintained in the volume under the flexible overlay 120 in the area of the wound 160 until the wound 160 has progressed toward a selected stage of healing.

Another embodiment of the invention is the wound treatment appliance 210 illustrated in FIG. 3. In this embodiment, the wound treatment appliance 210 is comprised of a wound treatment device 215 and a vacuum system, generally designated 250, that is operably connected to, and provides a supply of reduced pressure to, the wound treatment device 215. In addition, in this embodiment, the vacuum system 250 is further comprised of a reduced pressure supply source, generally designated 280, which is described in more detail below, and reduced pressure supply means, generally designated 240, which are described in more detail below. Also in this embodiment, the wound treatment device 215 is further comprised of a flexible overlay 220, wound packing means 278, and a suction drain 245. In the embodiment illustrated in FIG. 3, the flexible overlay 220 has substantially the same structure, features, characteristics and operation as the flexible overlay 20 described above and illustrated in connection with FIG. 1A. It is to be noted, however, that in other embodiments, the flexible overlay 220 may have substantially the same structure, features, characteristics, and operation as any embodiment of all of the flexible overlays 20, 20a, 20b, 20c described above and illustrated in connection with FIG. 1A, FIG. 1B, FIG. 1C, and FIG. 1D, respectively. It is also to be noted that in other embodiments the wound treatment device 220 may be comprised of almost any type of flexible, semi-rigid, or rigid wound covering apparatus currently known in the relevant art or that may be developed in the relevant art in the future that has a port and is designed to cover and enclose a wound and maintain reduced pressure in the area of the wound under the wound covering apparatus. For example, the overlay 220 may generally have substantially the same structure, features and characteristics as the embodiments of the rigid, semi-rigid or flexible wound covers described in U.S. patent application Ser. No. 10/652,100, which was filed by the present inventor with the U.S. Patent and Trademark Office on Aug. 28, 2003, and U.S. patent application Ser. No. 11/026,733, now U.S. Pat. No. 7,128,735, entitled "Improved Reduced Pressure Wound Treatment Appliance," which was filed by the present inventor with the U.S. Patent and Trademark Office on Dec. 30, 2004, the disclosures of which are incorporated herein by reference. In these embodiments, the overlay 220 may be sealed to the body in the area of the wound using any means disclosed in such applications or using the supplemental sealing means 176 described above and illustrated in connection with FIG. 2A. In the embodiment illustrated in FIG. 3, the flexible overlay 220 is placed over and encloses the entire wound 260 and is illustrated in a state of partial collapse, with the portion 229 of the flexible overlay 220 adjacent to the opening 221 in the perimeter 222 of the flexible overlay 220 forming an approximately hermetic seal with the adjacent portions 271 of the body 270. It is to be noted that in various embodiments, the wound treatment appliance 210 may also be comprised of tissue protection means 275, which may be substantially the same as the tissue protection means 175 described above and illustrated in connection with FIG. 2A.

In the embodiment of the invention illustrated in FIG. 3, the wound treatment device 215 is further comprised of wound packing means 278, which is placed in the area of the wound 260 under the flexible overlay 220. In this embodiment, the flexible overlay 220 is placed over the area of the wound 260 to be treated and the wound packing means 278 when the flexible overlay 220 is positioned on the surface of the body 270 at the site of the wound 260. In some embodiments, the wound packing means 278 may be placed within the wound 260 to prevent overgrowth of the tissue in the area of the wound 260. For example, and preferably in these cases, the wound packing means 278 may comprised of absorbent dressings, antiseptic dressings, nonadherent dressings, water dressings, or combinations of such dressings. More preferably, the wound packing means 278 may be comprised of gauze or cotton or any combination of gauze and cotton. In still other embodiments, the wound packing means 278 may be comprised of an absorbable matrix adapted to encourage growth of the tissue in the area of the wound 260 into the matrix. In these embodiments, the absorbable matrix (as wound packing means 278) is constructed of an absorbable material that is absorbed into the epithelial and subcutaneous tissue in the wound 260 as the wound 260 heals. The matrix (as wound packing means 278) may vary in thickness and rigidity, and it may be desirable to use a spongy absorbable material for the patient's comfort if the patient must lie upon the wound treatment device 215 during treatment. The matrix (as wound packing means 278) may also be perforated and constructed in a sponge-type or foam-type structure to enhance gas flow and to reduce the weight of the matrix. Because of the absorbable nature of the absorbable matrix (as wound packing means 278), the matrix should require less frequent changing than other dressing types during the treatment process. In other circumstances, the matrix (as wound packing means 278) may not need to be changed at all during the treatment process.

In some embodiments, the absorbable matrix (as wound packing means 278) may be comprised of collagens or other absorbable materials or combinations of all such materials. U.S. patent application Ser. No. 10/652,100, which was filed by the present inventor with the U.S. Patent and Trademark Office on Aug. 28, 2003 and published as U.S. Publication No. 2004/0073151 A1, and is hereby incorporated by reference, also discloses various embodiments of an absorbable matrix that may be utilized with various embodiments of the present invention. It is to be noted, however, that wound packing means 278 may not be utilized in other embodiments of the invention.

In the embodiment illustrated in FIG. 3, the wound treatment device 215 is also comprised of a suction drain 245 and suction drain connection means, which are described in more detail below, to operably connect the reduced pressure supply means 240 to the suction drain 245 so that the suction drain 245 is in fluid communication with the reduced pressure supply means 240 and reduced pressure is supplied to the volume under the flexible overlay 220 in the area of the wound 260 by means of the suction drain 245. In this embodiment, the suction drain 245 is further comprised of a bottom drain portion 245a extending into the area of the wound 260 under the impermeable overlay 220 from a top drain portion 245b positioned within the port 227. In various embodiments, the top drain portion 245b may be permanently or removably attached to the interior surface of the opening 228 of the port 227 using any suitable means, such as an adhesive, or by the top drain portion 245b having a shape adapted so that all or a portion of it fits tightly against all or a portion of the interior surface of the opening 228 in the port 227. It is to be noted that the top drain portion 245b must be sufficiently sealed against the surface of the port 227 in a manner so that reduced pressure can be maintained in the volume under the impermeable overlay 220 in the area of the wound 260. In the embodiment illustrated in FIG. 3, the top drain portion 245b and the bottom drain portion 245a of the suction drain 245 are comprised of polymer tubing that is flexible enough to allow the tubing to easily bend, but rigid enough to prevent the tubing from collapsing during use. In other embodiments, portions of the top drain portion 245b and the bottom drain portion 245a of the suction drain 245 may be comprised of other materials, such as flexible or semi-rigid polymers, plastics, rubber, silicone, or combinations of such materials. In yet other embodiments, the suction drain 245 may have different cross-sectional shapes, such as elliptical, square, rectangular, pentagonal, hexagonal, or other shapes, as long as the suction drain 245 is adapted to provide an approximately hermetic seal with the port 227, as described in more detail above. In still other embodiments, the bottom drain portion 245a of the suction drain 245 may be further comprised of wound suction means that may be used to remove debris, exudate and other matter from the wound 260. In the embodiment illustrated in FIG. 3, the wound suction means is comprised of a distal end portion 245a' of the tubing comprising the bottom drain portion 245a having a plurality of perforations 245a" in the surface of the distal end portion 245a'. In other embodiments, the distal end portion 245a' of the bottom drain portion 245a may have almost any shape or combination of shapes (e.g., circular, elliptical, square, pentagonal, or hexagonal), including a shape different from the remaining portion of the bottom drain portion 245a, may be of almost any size relative to the remaining bottom drain portion 245a (e.g., may be longer or shorter than the remaining bottom drain portion 245a or have a cross-section smaller or larger than the remaining bottom drain portion 245a, or both), may have more or fewer perforations 245a", may have different sizes and shapes of perforations 245a", may extend along different portions of the bottom drain portion 245a, and may be constructed in whole or in part of materials that are not flexible. In embodiments that have a distal end portion 245a', the distal end portion 245a' may be attached to the remaining portion of the bottom drain portion 245a in almost any manner, as long as the remaining bottom drain portion 245a is in fluid communication with the wound suction means 245a'. Examples include an adhesive in some embodiments and a fastening collar in other embodiments. In still other embodiments, the distal end portion 245a' may be fused or welded to the remaining portion of the bottom drain portion 245a. In yet other embodiments, the distal end portion 245a' and the remaining portion of the bottom drain portion 245a may be fabricated as a single piece.

In some embodiments, as illustrated in FIG. 3, the top drain portion 245b may extend beyond the top of the port 227 into the area outside the volume of the flexible overlay 220. In some of these embodiments, as is also illustrated in FIG. 3, the suction drain connection means, which may be used to removably connect the reduced pressure supply means 240 to the top drain portion 245b of the suction drain 245 is a variable descending diameter adapter 246 (commonly referred to as a "Christmas tree" adapter) that is placed into the interior volume of the top drain portion 245b at its distal end. In other embodiments, the suction drain connection means may be clamps, fastening collars, or other fasteners or combinations thereof. In yet other embodiments, the top drain portion 245b may be fused or welded to the reduced pressure supply means 240. In still other embodiments, the top drain portion 245b and the portion of the reduced pressure supply means 240 adjacent to the top drain portion 245b may be fabricated as a single piece. In other embodiments, the top drain portion 245b may not extend beyond the top of the port 227 and the reduced pressure supply means 240 may connect directly to the port 227 using any suitable means, such as an adhesive, welding, fusing, clamps, collars or other fasteners, or any combination of such means.

In the embodiment illustrated in FIG. 3, the distal end portion 245a' of the suction drain 245 extends into the interior volume of the wound packing means 278. In this embodiment, the wound packing means 278 and the suction drain 245 may be fabricated by snaking the distal end portion 245a' of the suction drain 245 through an internal passageway in the wound packing means 278, such as by pulling the distal end portion 245a' of the suction drain 245 through the passageway using forceps. Alternatively, the wound packing means 278 and the suction drain 245 may be manufactured as a single piece in sterile conditions and then be stored in an aseptic package until ready for use. In other embodiments, the distal end portion 245a' of the suction drain 245 may be placed adjacent or close to the wound packing means 278 in the area of the wound 260. The preferred means of placement of the suction drain 245 relative to the wound packing means 278 is dependent upon the type of wound 260, the wound packing means 278, and the type of treatment desired. Referring to FIG. 3 as an example, it is therefore to be noted that in some embodiments, the wound treatment device 215 may utilize a suction drain 245 without utilizing wound packing means 278, while in other embodiments a suction drain 245 may be utilized with wound packing means 278. In addition, in other embodiments, the wound treatment device 215 may utilize wound packing means 278 without utilizing a suction drain 245, while in other embodiments wound packing means 278 may be utilized with a suction drain 245.

In the embodiment illustrated in FIG. 3, the vacuum system 250, which in conjunction with the wound treatment device 215 also represents another embodiment of the invention, is generally comprised of a suction bulb 281 having an inlet port 282 and an outlet port 283, a bulb connection tubing member 284, an exhaust tubing member 285, an exhaust control valve 286, a filter 287, and a supplemental vacuum system (illustrated schematically and generally designated 250a). In this embodiment, the suction bulb 281 is a hollow sphere that may be used to produce a supply of reduced pressure for use with the wound treatment device 215. In addition, the suction bulb 281 may also be used to receive and store fluid aspirated from the wound 260. The inlet port 282 of the suction bulb 281 is connected to one end of the bulb connection tubing member 284, which is also the reduced pressure supply means 240 in this embodiment. The connection tubing member 284 is connected by suction drain connection means to the top drain portion 245b at its other end in a manner so that the interior volume of the suction bulb 281 is in fluid communication with the suction drain 245. In this embodiment, the bulb connection tubing member 284 is sufficiently flexible to permit movement of the bulb connection tubing member 284, but is sufficiently rigid to resist constriction when reduced pressure is supplied to the suction drain 245 or when the location of the wound 260 is such that the patient must sit or lie upon the bulb connection tubing member 284 or upon the wound treatment device 215. The outlet port 283 of the suction bulb 281 is connected to the exhaust tubing member 285. In this embodiment, the exhaust tubing member 285 is sufficiently flexible to permit movement of the exhaust tubing member 285, but is sufficiently rigid to resist constriction when reduced pressure is supplied to the suction drain 245. The inlet port 282 of the suction bulb 281 may be connected to the bulb connection tubing member 284 and the outlet port 283 of the suction bulb 281 may be connected to the exhaust tubing member 285 using any suitable means, such as by welding, fusing, adhesives, clamps, or any combination of such means. In addition, in some embodiments, the suction bulb 281, the bulb connection tubing member 284, and the exhaust tubing member 285 may be fabricated as a single piece. In the illustrated embodiment, the exhaust control valve 286 and the filter 287 are operably connected to the exhaust tubing member 285. In this embodiment, the exhaust control valve 286 is used to regulate the flow of fluids (gases and liquids) to and from the suction bulb 281 and the supplemental vacuum system 250a. In embodiments of the invention that do not have a supplemental vacuum system 250a, the exhaust control valve 286 regulates flow of fluids to and from the suction bulb 281 and the outside atmosphere. Generally, the exhaust control valve 286 allows fluids to flow out of the suction bulb 281 through the outlet port 283, but not to flow in the reverse direction unless permitted by the user of the appliance 210. Any type of flow control valve may be used as the exhaust control valve 286, as long as the valve is capable of operating in the anticipated environment involving reduced pressure and wound 260 exudate. Such valves are well known in the relevant art, such as sprung and unsprung flapper-type valves and disc-type valves. In this embodiment, the filter 287 is operably attached to the exhaust tubing member 285 between the outlet port 283 of the suction bulb 281 and the exhaust control valve 286. The filter 287 prevents potentially pathogenic microbes or aerosols from contaminating the exhaust control valve 286 (and supplemental vacuum system 250a), and then being vented to atmosphere. The filter 287 may be any suitable type of filter, such as a micropore filter. In other embodiments, the filter 287 may also be a hydrophobic filter that prevents any exudate from the wound 260 from contaminating the exhaust control valve 286 (and the supplemental vacuum system 250a) and then being vented to atmosphere. In still other embodiments, the filter 287 may perform both functions. It is to be noted, however, that the outlet port 283, the exhaust control valve 286, the filter 287, or any combination of the exhaust control valve 286 and the filter 287, need not be utilized in connection with the vacuum system 250 in other embodiments of the invention.

In some embodiments of the invention illustrated in FIG. 3 that do not utilize a supplemental vacuum system 250a, the suction bulb 281 may be used to produce a supply of reduced pressure in the following manner. First, the user of the appliance 210 appropriately seals all of the component parts of the appliance 210 in the manner described herein. For example, the impermeable overlay 220 is sealed (or placed adjacent) to the body 170 and the suction drain 245 is sealed to the bulb connection tubing member 284 and the surface of the port 227. The user then opens the exhaust control valve 286 and applies force to the outside surface of the suction bulb 281, deforming it in a manner that causes its interior volume to be reduced. When the suction bulb 281 is deformed, the gas in the interior volume is expelled to atmosphere through the outlet port 283, the exhaust tubing member 285, the filter 287, and the exhaust control valve 286. The user then closes the exhaust control valve 286 and releases the force on the suction bulb 286. The suction bulb 281 then expands, drawing fluid from the area of the wound 260 under the wound treatment device 215 into the suction bulb 281 through the suction drain 245 and causing the pressure in such area to decrease. To release the reduced pressure, the user of the appliance 210 may open the exhaust control valve 286, allowing atmospheric air into the interior volume of the suction bulb 281. The level of reduced pressure may also be regulated by momentarily opening the exhaust control valve 286.

The suction bulb 281 may be constructed of almost any fluid impermeable flexible or semi-rigid material that is suitable for medical use and that can be readily deformed by application of pressure to the outside surface of the suction bulb 281 by users of the appliance 210 and still return to its original shape upon release of the pressure. For example, the suction bulb 281 may be constructed of rubber, neoprene, silicone, or other flexible or semi-rigid polymers, or any combination of all such materials. In addition, the suction bulb 281 may be of almost any shape, such as cubical, ellipsoidal, or polygonal. The suction bulb 281 may also be of varying size depending upon the anticipated use of the suction bulb 281, the size of the wound treatment device 215, use of a supplemental vacuum system 250a, the level of reduced pressure desired, and the preference of the user of the appliance 210. In the embodiment of the invention illustrated in FIG. 3, the supplemental vacuum system 250a is connected to the exhaust tubing member 285 and is used to provide a supplemental supply of reduced pressure to the suction bulb 281 and wound treatment device 215. In this embodiment, the supplemental vacuum system 250a may have substantially the same structure, features, characteristics, and operation of the various embodiments of the vacuum system 50 described above and illustrated in connection with FIG. 2A and FIG. 2B. It is to be noted, however, that the supplemental vacuum system 250a need not be used in connection with the vacuum system 280 in other embodiments of the invention.

Except as described below, the wound treatment appliance 210 described above and illustrated in connection with FIG. 3 may generally be used in a manner similar to the wound treatment appliance 110 described above and illustrated in connection with FIG. 2A and FIG. 2B. As a result, except as described below, the example of how the embodiment of the wound treatment appliance 110 and the flexible overlay 120 described above and illustrated in connection FIG. 2A may be used in treatment of a wound 160 also applies to the embodiment of the appliance 210 described above and illustrated in connection with FIG. 3. In the case of the embodiment illustrated in FIG. 3, however, the wound packing means 278 is placed into the wound 260 prior to placement of the flexible overlay 220 over the portion of the wound 260 to be treated. In addition, the flexible overlay 220 is placed over the wound packing means 278. In embodiments where the distal end portion 245a' of a suction drain 245 is placed into the interior volume of, or adjacent to, the wound packing means 278, the distal end portion 245a' of the suction drain 245 is also placed in the appropriate position before the flexible overlay 220 is placed over the wound 260. In embodiments utilizing a suction drain 245 without wound packing means 278, the suction drain 245 is installed in the flexible overlay 220 before the flexible overlay 220 is placed over the wound 260.

Another embodiment of the invention is the wound treatment appliance 310 illustrated in FIG. 4. FIG. 4 also illustrates another example of how the embodiment of the flexible overlay 20 described above and illustrated in connection with FIG. 1A may be used to provide reduced pressure treatment for a wound 360 on the body 370 of a patient. In this embodiment, the wound treatment appliance 310 is comprised of a flexible overlay 320 and a vacuum system, generally designated 350, that is operably connected to, and provides a supply of reduced pressure to, the flexible overlay 320. In addition, in this embodiment, the vacuum system 350 is further comprised of a reduced pressure supply source, generally designated 330, which is described in more detail below, and reduced pressure supply means, generally designated 340, which are described in more detail below. In this embodiment, the reduced pressure supply means 340 are used to connect the reduced pressure supply source 330 to the flexible overlay 320 in a manner so that reduced pressure is supplied to the area under the flexible overlay 320, as described in more detail below. In the embodiment illustrated in FIG. 4, the flexible overlay 320 has substantially the same structure, features, and characteristics as the flexible overlay 20 described above and illustrated in connection with FIG. 1A. It is to be noted, however, that in other embodiments, the flexible overlay 320 may have substantially the same structure, features, and characteristics as any embodiment of all of the flexible overlays 20, 20a, 20b, 20c of the other embodiments described above and illustrated in connection with FIG. 1A, FIG. 1B, FIG. 1C, and FIG. 1D, respectively. In this example, the flexible overlay 320 is placed over and encloses the entire wound 360, which is at the distal end of an amputated limb. It is to be noted that in other embodiments, the appliance 310 may also be comprised of tissue protection means 375, which may be substantially the same as the tissue protection means 175 of the embodiment described above and illustrated in connection with FIG. 2A. In other embodiments, the appliance 310 may also be comprised of wound packing means (not illustrated), which may be substantially the same as the wound packing means 278 of the embodiment described above and illustrated in connection with FIG. 3.

In the embodiment illustrated in FIG. 4, the reduced pressure supply source 330 of the vacuum system 350, which produces a source of reduced pressure or suction that is supplied to the flexible overlay 320, includes a small, portable vacuum pump 331, a filter 333, and a power source (not illustrated) that is contained within the housing for the portable vacuum pump 331. In the illustrated embodiment, predetermined amounts of suction or reduced pressure are produced by the portable vacuum pump 331. The portable vacuum pump 331 is preferably controlled by a control device (not illustrated) that is also located within the housing for the portable vacuum pump 331, which may provide substantially the same functions as the control device 132 described above and illustrated in connection with FIG. 2A and FIG. 2B. Except for its smaller size, the portable vacuum pump 331 may operate in substantially the same manner as the vacuum pump 131 of the invention described above and illustrated in connection with FIG. 2A and FIG. 2B. In the embodiment illustrated in FIG. 4, the filter 333 may have the same structure, features, characteristics, and operation, and provide substantially the same functions, as the filter 133 described above and illustrated in connection with FIG. 2A and FIG. 2B. The power source may be any source of energy currently known in the art or that may be developed in the art in the future that may be used to power the portable vacuum pump 331. For example, in some embodiments, the power source may be a fuel cell, battery or connection to a standard electrical outlet. In the illustrated embodiment, the filter 333 is rigidly connected to the portable vacuum pump 331. It is to be noted that in other embodiments, the reduced pressure supply source 330 may not have a filter 333.

In the embodiment illustrated in FIG. 4, the reduced pressure supply means 340 of the vacuum system 350, which is used to connect the reduced pressure supply source 330 to a port 327 on the flexible overlay 320 so that reduced pressure is supplied to the area of the wound 360 under the flexible overlay 320, is comprised of at least one tubing member 341. In this embodiment, the at least one tubing member 341 is a rigid tubing member. In other embodiments, the at least one tubing member 341 may be sufficiently flexible to permit movement of the at least one tubing member 341, but is sufficiently rigid to resist constriction when reduced pressure is supplied to the port 327 or when the location of the wound 360 is such that the patient must sit or lie upon the at least one tubing member 341 or upon the flexible overlay 320. In the embodiment illustrated in FIG. 4, the at least one tubing member 341 is connected to the port 327 by inserting one end of the at least one tubing member 341 into an opening 328 in the port 484 and sealing (such as with an adhesive) the at least one tubing member 341 to the port 327. It is to be noted that in other embodiments, the at least one tubing member 341 may be connected to the port 327 using any suitable means currently known in the relevant art or developed in the relevant art in the future. Examples include the suction drain connection means of the embodiment discussed above and illustrated in connection with FIG. 3. Similar means may be used to connect the other end of the at least one tubing member 341 to the reduced pressure supply source 330 providing the reduced pressure. In other embodiments, the reduced pressure supply means 340 may further comprise a fluid collection system (not illustrated), which may generally have the same structure, features, characteristics, and operation, and perform the same functions, as the fluid collection system 142 of the embodiment described above and illustrated in connection with FIG. 2A and FIG. 2B.

Another embodiment of the current invention is the wound treatment appliance 410 illustrated in FIG. 5. In this embodiment, the appliance 410 is comprised of a wound treatment device 415, which is further comprised of a flexible overlay 420, a collection chamber 490 to receive and hold fluid aspirated from the wound 460, collection chamber attachment means to operably attach the collection chamber 490 to the overlay 420, as described in more detail below, and reduced pressure supply means, generally designated 440, which are described in more detail below. In this embodiment, the flexible overlay 420 is adapted to be placed over and enclose all or a portion of the wound 460 in the same manner as the flexible overlay 20 described in detail above and illustrated in connection with FIG. 1A. It is to be noted, however, that the flexible overlay 420 illustrated in FIG. 5 is shown in position on the body 470 over the wound 460, but not in its collapsed state. In the illustrated embodiment, and except as described in more detail below, the flexible overlay 420 has substantially the same structure, features and characteristics as the flexible overlay 20 described in detail above and illustrated in connection with FIG. 1A. In various embodiments, except as described in more detail below, the flexible overlay 420 may have substantially the same structure, features, characteristics and operation as the embodiments of the flexible overlays 20, 20a, 20b, 20c, 120, 220 described in more detail above and illustrated in connection with FIG. 1A, FIG. 1B, FIG. 1C, FIG. 1D, FIG. 2A, and FIG. 3, respectively. In addition, the overlay 420 may be almost any type of semi-rigid or rigid wound covering apparatus currently known in the relevant art or that may be developed in the relevant art in the future that has a port and is designed to cover and enclose a wound and maintain reduced pressure in the area of the wound under the wound covering apparatus. For example, the overlay 420 may generally have substantially the same structure, features and characteristics as the embodiments of the rigid or semi-rigid generally conically-shaped or cup-shaped wound covers described in U.S. patent application Ser. No. 10/652,100, which was filed by the present inventor with the U.S. Patent and Trademark Office on Aug. 28, 2003, and published as U.S. Publication No. 2004/0073151 A1, and U.S. patent application Ser. No. 11/026,733, now U.S. Pat. No. 7,128,735, entitled "Improved Reduced Pressure Wound Treatment Appliance," which was filed by the present inventor with the U.S. Patent and Trademark Office on Dec. 30, 2004, the disclosures of which are incorporated herein by reference. In the illustrated embodiment, reduced pressure supply means, generally designated 440, which are described in more detail below, are used to operably connect the collection chamber 490 to a reduced pressure supply source, generally designated 430, which is described in more detail below, that provides a supply of reduced pressure to the collection chamber 490, so that the volume within the collection chamber 490 and under the flexible overlay 420 in the area of the wound 460 to be treated are supplied with reduced pressure by the reduced pressure supply source 430. Together, the reduced pressure supply means 440 and the reduced pressure supply source 430 comprise a vacuum system, generally designated 450. In various embodiments, except as described in more detail below, the reduced pressure supply means 440 used to connect the reduced pressure supply source 430 to the collection chamber 490 may have substantially the same structure, features, characteristics, and operation as the reduced pressure supply means 140, 240, 340 described above and illustrated in connection with FIG. 2A, FIG. 2B, FIG. 3, and FIG. 4, respectively. In addition, in various embodiments, except as described in more detail below, the reduced pressure supply source 430 used to provide the supply of reduced pressure to the collection chamber 490 may have substantially the same structure, features, characteristics, and operation as the reduced pressure supply source 130, 280, 330 described above and illustrated in connection with FIG. 2A, FIG. 2B, FIG. 3, and FIG. 4, respectively.

In the embodiment of the appliance 410 illustrated in FIG. 5, the collection chamber 490 is approximately cylindrical in shape. In other embodiments, the collection chamber 490 may have other shapes. For example, the collection chamber may be shaped approximately as a sphere, ellipsoid, cube, polyhedron, or other shape or combination of such shapes, as long as the collection chamber 490 has an interior volume to receive and hold fluid aspirated from the wound 460. The collection chamber 490 may also be of almost any size. For example, the collection chamber 490 may be relatively small where the wound 460 is expected to aspirate only a small volume of fluid. On the other hand, the collection chamber 490 may be relatively large where it is expected that the wound 460 will aspirate a large volume of fluid. As a result, the preferred size of the collection chamber 490 is dependent upon the size of the wound 460 to be treated, the size of the flexible overlay 420, the type of wound 460 to be treated, and the preference of the user of the appliance 410. In various embodiments, the collection chamber 490 may be comprised of almost any medical grade material that is currently known in the art or that may be developed in the art in the future, as long as such material is fluid-impermeable and suitable for purposes of wound treatment (e.g., can be sterilized and does not absorb significant amounts of wound 460 exudate). For example, the collection chamber 490 may be comprised of rubber (including neoprene) and polymer materials, such as silicone, silicone blends, silicon substitutes, polyvinyl chloride, polycarbonates, polyester-polycarbonate blends, or a similar polymer, or combinations of all such materials. It is to be noted that the collection chamber 490 may have a rigid or semi-rigid structure in some embodiments. In other embodiments, the collection chamber 490 may be more flexible so that it can be squeezed in a manner similar to the suction bulb 281, as described above and illustrated in connection with FIG. 3. Although the collection chamber 490 may be constructed of a material different from the material comprising the flexible overlay 420 in various embodiments of the invention, the collection chamber 490 is preferably constructed from the same material comprising the flexible overlay 420. The collection chamber 490 may be constructed using any suitable means currently known in the art or that may be developed in the art in the future. For example, a collection chamber 490 constructed of silicone may be manufactured by means of injection molding.

In various embodiments, the collection chamber attachment means operably attaches the collection chamber 490 to the flexible overlay 420 in a manner so that exudate and reduced pressure are permitted to flow between the collection chamber 490 and the volume under the flexible overlay 420 in the area of the wound 460. Also, in various embodiments, as illustrated by the appliance 410 in FIG. 5, the collection chamber 490 is positioned approximately adjacent to the flexible overlay 420 on the side of the flexible overlay 420 opposite the wound 460. Although the collection chamber 490 and the collection chamber attachment means are positioned approximately at the apex of the flexible overlay 420 in the illustrated embodiment, in other embodiments the collection chamber 490 and collection chamber attachment means may be positioned at almost any location on the surface of the impermeable overlay 420 opposite the wound 460, as long as the collection chamber 490 and collection chamber attachment means do not materially interfere with the operation of the flexible overlay 420. As illustrated in FIG. 5, the collection chamber attachment means may be a rigid or semi-rigid connecting member 491 between the collection chamber 490 and the flexible overlay 420. In this embodiment, the connecting member 491 is approximately cylindrical in shape and has a port 492 therein, which is also approximately cylindrical in shape and extends between the collection chamber 490 and the flexible overlay 420 so that fluids can flow between the collection chamber 490 and the flexible overlay 420. In other embodiments, the connecting member 491 and the port 492 may be of almost any shape or combination of shapes. For example, the connecting member 491 and the port 492 may be shaped approximately as a sphere, ellipsoid, cube, polygon, paraboloid, or any other shape or combination of shapes, as long as the connecting member 491 provides a rigid or semi-rigid connection between the collection chamber 490 and the flexible overlay 420 that is adequate to support the collection chamber 490 when it is filled with exudate from the wound 460, and the port 492 is of a size and shape adequate to allow the flow of exudate from the wound 460 between the collection chamber 490 and the flexible overlay 420. For example, the collection chamber 490 in some embodiments may have approximately the same outside diameter as the connecting member 491, as illustrated by the phantom lines 493 in FIG. 5. The connecting member 491 may generally be constructed of any material that is suitable for construction of the collection chamber 490 or the flexible overlay 420, and is preferably constructed from the same materials as the collection chamber 490 and the flexible overlay 420. In various embodiments, the collection chamber 490 and the flexible overlay 420 may be connected to the connecting member 491 using any suitable means, such as by adhesives, welding, fusing, clamps, and other fastening means or combinations of such means. In yet other embodiments, the collection chamber 490, the flexible overlay 420, and the connecting member 491 may be fabricated as a single piece. In still other embodiments, one or more of the connections between the collection chamber 490, the flexible overlay 420, and the connecting member 491 may provide for removing one component from another to empty fluid from the collection chamber 490. For example, the collection chamber 490, the flexible overlay 420, and the connecting member 491 may each be threaded at their points of connection so that they can be screwed together and then unscrewed when desired. In still other embodiments, the collection chamber 490 and the flexible overlay 420 may be directly connected together without a connecting member 491, as long as the connection allows fluid to flow between the collection chamber 490 and the flexible overlay 420. Such connection may be made using any of the means described above in this paragraph.

In some embodiments, as illustrated in FIG. 5, the connecting member 491, as the collection chamber attachment means, may be further comprised of a flow control means, which is described in more detail below, operably positioned between the collection chamber 490 and the flexible overlay 420. In these embodiments, the flow control means permits fluid aspirated from the wound 460 to flow from the volume under the flexible overlay 420 in the area of the wound 460 through the port 492 into the collection chamber 490, but not in the opposite direction. In the illustrated embodiment, the flow control means is comprised of a flapper-type valve 494. In this embodiment, the valve 494 has two flapper members 494*a* that are hinged at their distal end to a portion of the connecting member 491, and the flapper members 494*a* are of a shape and size adapted to substantially close the port 492 when they are positioned in the closed position. In other embodiments, the flow control means may be comprised of a disc-type valve, wherein the disc of the valve moves with the flow of fluids and contacts a seat disposed around the perimeter of the port when the flow of fluids is misdirected, so that the port is sealed closed and prevents fluid flow in the wrong direction. In some embodiments, as illustrated in FIG. 5, the collection chamber 490 may be further comprised of a shroud 495 (illustrated by the phantom lines) that extends from a portion of the collection chamber 490 to the flexible overlay 420. In these embodiments, the shroud 495 is approximately tubular in shape. In other embodiments, the shroud 495 may have other shapes. The shroud 495 generally provides additional support for the collection chamber 490 and may also provide for a more aesthetically pleasing appearance for the appliance 410. In addition, in the embodiment of the appliance 410 illustrated in FIG. 5, the reduced pressure supply means 440 is connected to the collection chamber 490 by means of a stopper 445 adapted to fit into an opening 496 in the collection chamber 490. The stopper 445 forms a seal with the portion of the collection chamber 490 adjacent to the opening 496 so that reduced pressure can be maintained within the interior volume of the collection chamber 490. In this embodiment, the reduced pressure supply means is comprised of a tubular member 441 that is positioned in a port 446 in the stopper 445 at one end and is connected to the reduced pressure supply source 430 at the other end.

The embodiment of the appliance 410 illustrated in FIG. 5 may be used to treat a wound 460 on a body 470 using a method comprising the following steps. First, the wound treatment device 415 is positioned on the body 470 over the area of the wound 460 to be treated. Next, the vacuum system 450 is operably connected to the collection chamber 490. The flexible overlay 420 may then be collapsed in the approximate direction of the wound 460 when reduced pressure is supplied to the volume under the flexible overlay 420 in the area of the wound 460 so that an approximately hermetic seal (as illustrated and described in more detail above in connection with FIG. 2A) is formed between the flexible overlay 420 and the body 470 in the area of the wound 460. Next, reduced pressure is maintained in the volume of the flexible overlay 420 in the area of the wound 460 until the area of the wound 460 being treated has progressed toward a selected stage of healing. In other embodiments, the method may further comprise the step of placing tissue protection means 475, which may be substantially the same as the tissue protection means 175, as described above and illustrated in connection with FIG. 2A, on the tissue 471 of the body 470 that is to be approximately adjacent to the flexible overlay 420, such step being performed prior to positioning the flexible overlay 420 over the area of the wound 460 to be treated. In yet other embodiments, the method further comprises the step of placing wound packing means (not illustrated), which may be substantially the same as the wound packing means 278, as described above and illustrated in connection with FIG. 3, between the wound 460 and the impermeable overlay 420 in the area of the wound 460 to be treated, such step being performed prior to positioning the impermeable overlay 420 over the area of the wound 460 to be treated. In still other embodiments, the reduced pressure under the flexible overlay 420 in the area of the wound 460 is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure. In yet other embodiments, the method is further comprised of the step of emptying any fluid collected in the collection chamber 490. This step may be performed after the flexible overlay 420 is collapsed in the approximate direction of the wound 460 and may also be performed before or after the area of the wound 460 being treated has progressed toward a selected stage of healing.

Figure 6:
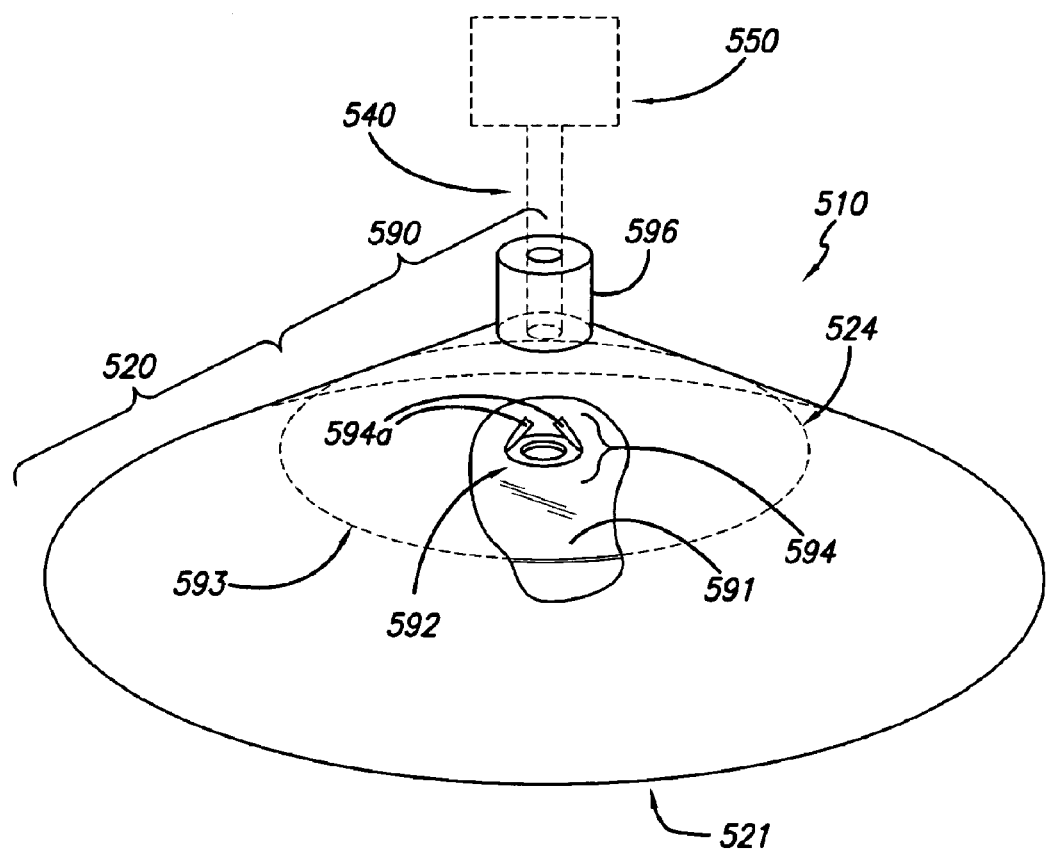
FIG. 6 is a view of another embodiment of a wound treatment appliance, in which an embodiment of an impermeable flexible overlay is shown in partially broken away perspective view from the side of and above the flexible overlay (as the flexible overlay would be oriented when placed on the body of a patient), and in which an embodiment of a vacuum system, depicted generally and shown in schematic elevation view, provides reduced pressure within the area under the flexible overlay.

Another embodiment of the invention is the wound treatment appliance 510 illustrated in FIG. 6. In this embodiment, the appliance 510 is comprised of a flexible overlay 520, a collection chamber 590 to receive and hold fluid aspirated from a wound (not shown), collection chamber attachment means to operably attach the collection chamber 590 to the flexible overlay 520, as described in more detail below, and reduced pressure supply means, generally designated 540, which are described in more detail below. In this embodiment, the flexible overlay 520 is adapted to be placed over and enclose all or a portion of a wound in the same manner as the flexible overlay 20a described in detail above and illustrated in connection with FIG. 1B. It is to be noted that the flexible overlay 520 illustrated in FIG. 6 is not shown in its collapsed state. In the illustrated embodiment, and except as described in more detail below, the flexible overlay 520 has substantially the same structure, features, and characteristics as the flexible overlay 20a described in detail above and illustrated in connection with FIG. 1B. In other embodiments, the flexible overlay 520 may be of other shapes and have other features. For example, the flexible overlay 520 may be of the shape and have the features illustrated and described above in connection with the appliance 10b and 10c of FIG. 1C and FIG. 1D, respectively. In the embodiment illustrated in FIG. 6, the reduced pressure supply means 540, which are described in more detail below, may be used to operably connect the collection chamber 590 to a reduced pressure supply source (not shown), which is described in more detail below, that provides a supply of reduced pressure to the collection chamber 590, so that the volume within the collection chamber 590 and under the flexible overlay 520 in the area of the wound to be treated are supplied with reduced pressure by the reduced pressure supply source. Together, the reduced pressure supply means 540 and the reduced pressure supply source comprise a vacuum system, generally designated 550. In this embodiment, except as described in more detail below, the reduced pressure supply means 540 used to connect the reduced pressure supply source to the collection chamber 590 may have substantially the same structure, features, characteristics, and operation as the reduced pressure supply means 140, 240, 340 described above and illustrated in connection with FIG. 2A, FIG. 2B, FIG. 3, and FIG. 4, respectively. In addition, in this embodiment, except as described in more detail below, the reduced pressure supply source used to provide the supply of reduced pressure to the collection chamber 590 may have substantially the same structure, features, characteristics, and operation as the reduced pressure supply source 130, 280, 330 described above and illustrated in connection with FIG. 2A, FIG. 2B, FIG. 3, and FIG. 4, respectively. The embodiment of the appliance 510 illustrated in FIG. 6 may be used to treat a wound on a body using substantially the same method described above in connection with the appliance 410 illustrated in FIG. 5.

In the embodiment illustrated in FIG. 6, the collection chamber 590 is positioned approximately adjacent to the flexible overlay 520 on the side of the flexible overlay 520 opposite the wound. In this embodiment, the collection chamber attachment means, as described in more detail below, is comprised of a membrane 591. In this embodiment, the membrane 591 acts as a barrier separating the collection chamber 590 and the flexible overlay 520, so that the membrane 591 acts as a portion of the surface of the collection chamber 590 and a portion of the surface of the flexible overlay 520. In addition, the membrane 591 has at least one port 592 therein so that the volume within the collection chamber 590 is in fluid communication with the volume under the flexible overlay 520 in the area of the wound. It is to be noted that there may be more than one port 592 in other embodiments. The number of ports 492 is generally dependent upon the size and shape of the collection chamber 590, the size and shape of the impermeable flexible overlay 520, the anticipated amount of exudate to be aspirated from the wound, the level of reduced pressure to be utilized, and the individual preference of the user of the appliance 510. In embodiments where the flexible overlay 520 has an approximately elongated conical shape, as illustrated in FIG. 6, the flexible overlay 520 may have a base end opening 521 and a top end opening 524 opposite the base end opening 521. In these embodiments, the base end opening 521 may have an either approximately circular shape or approximately elliptical shape sized to be placed over and enclose the area of the wound to be treated. The top end opening 524 may have either an approximately circular shape or approximately elliptical shape. In the illustrated embodiments, the membrane 591 is adapted to be of the same shape and size as the top end opening 524 and the membrane 591 is positioned so that it is attached to the entire perimeter of the top end opening 524 and covers the entire top end opening 524. The membrane 591 may be attached to the perimeter of the top end opening 524 by any suitable means currently known in the relevant art or developed in the art in the future. Examples of such means include welding or fusing the membrane 591 to the perimeter of the top end opening 524. Alternatively, the membrane 591 may be fabricated as a single piece with the flexible overlay 520.

In the embodiment of the appliance 510 illustrated in FIG. 6, the collection chamber 590 has an approximately elongated conical shape, a chamber bottom end opening 593, and a reduced pressure supply port 596 positioned at the apex of the collection chamber 590 opposite the chamber bottom end opening 593. The reduced pressure supply port 596 may be used to operably connect the reduced pressure supply means 540 to the collection chamber 590. In some embodiments, a micropore or hydrophobic filter or both (not shown) may be operably positioned within the reduced pressure supply port 596 or the connection with the reduced pressure supply means 540 to retain the exudate from the wound within the collection container 590 or to prevent exudate from contaminating portions of the vacuum system 550, or both. In the illustrated embodiment, the chamber bottom end opening 593 is adapted to be of approximately the same size and shape as the top end opening 524 of the impermeable flexible overlay 520. In other embodiments, the collection chamber 590 may be of other shapes and sizes and its bottom end opening 593 may not necessarily be of the same size and shape as the top end opening 524 of the flexible overlay 520. In all embodiments, however, the collection chamber 590 is attached to the membrane 591 in a manner so that the membrane 591 acts as a portion of the surface of the collection chamber 590 and so that the volume within the collection chamber 590 is airtight, except for the at least one port 592 and the reduced pressure supply port 596. In one embodiment, the collection chamber 590 and the flexible overlay 520 have the shapes illustrated in FIG. 6. The membrane 591 may be attached to the perimeter of the chamber bottom end opening 593 by any suitable means currently known in the relevant art or developed in the art in the future. Examples of such means include welding or fusing the membrane 591 to the perimeter of the chamber bottom end opening 593. Alternatively, the membrane 591 or the flexible overlay 520, or both, may be fabricated as a single piece with the collection chamber 590. The preferred shapes and sizes of the collection chamber 590 and the flexible overlay 520 are dependent upon the size and type of wound to be treated, the area of the body on which the wound is positioned, the level of reduced pressure to be utilized, the amount of collapse of the flexible overlay 520 desired, and the preference of the user of the appliance 510. In this embodiment of the invention, the collection chamber 590 may be comprised of almost any medical grade material that is currently known in the art or that may be developed in the art in the future, as long as such material is fluid-impermeable and suitable for purposes of wound treatment (e.g., can be sterilized and does not absorb significant amounts of wound exudate). For example, the collection chamber 590 may be comprised of rubber (including neoprene) and flexible polymer materials, such as silicone, silicone blends, silicone substitutes, polyvinyl chloride, polycarbonates, polyester-polycarbonate blends, or a similar polymer, or combinations of all such materials. It is to be noted that the collection chamber 590 may have a rigid or semi-rigid structure in some embodiments. In other embodiments, the collection chamber 590 may be more flexible so that it can be squeezed in a manner similar to the suction bulb 281, as described above and illustrated in connection with FIG. 3. Although the collection chamber 590 may be constructed of a material different from the material comprising the flexible overlay 520 in various embodiments of the invention, the collection chamber 590 is preferably constructed from the same material comprising the flexible overlay 520. The collection chamber 590 may be constructed using any suitable means currently known in the art or that may be developed in the art in the future. For example, a collection chamber 590 constructed of silicone may be manufactured by means of injection molding.

In the embodiment illustrated in FIG. 6, the membrane 591 and its means of being sealed to the perimeters of the top end opening 524 and the chamber bottom end opening 593, together as collection chamber attachment means, operably attach the collection chamber 590 to the impermeable overlay 520 in a manner so that exudate and reduced pressure are permitted to flow between the collection chamber 590 and the volume under the impermeable overlay 520 in the area of the wound. In the embodiment illustrated in FIG. 6, the at least one port 592 is approximately cylindrical in shape and extends between the collection chamber 590 and the flexible overlay 520 so that fluids can flow between the collection chamber 590 and the flexible overlay 520. In other embodiments, the at least one port 592 may be of almost any shape or combination of shapes. In some embodiments, as illustrated in FIG. 6, the membrane 591 comprising the collection chamber attachment means may be further comprised of a flow control means, which is described in more detail below, operably connected with the at least one port 592 and positioned between the collection chamber 590 and the flexible overlay 520. In these embodiments, the flow control means permits fluid aspirated from the wound to flow from the volume under the flexible overlay 520 in the area of the wound 560 through the at least one port 592 into the collection chamber 590, but not in the opposite direction. In the illustrated embodiment, the flow control means is comprised of a flapper-type valve 594. In this embodiment, the valve 594 has two flapper members 594a that are hinged at their distal end to a portion of the membrane 491 or supporting structure surrounding the at least one port 492 and the flapper members 594a are of a shape and size adapted to substantially close the at least one port 592 when they are positioned in the closed position. In other embodiments, the flow control means may be comprised of a disc-type of valve.

Figure 7:
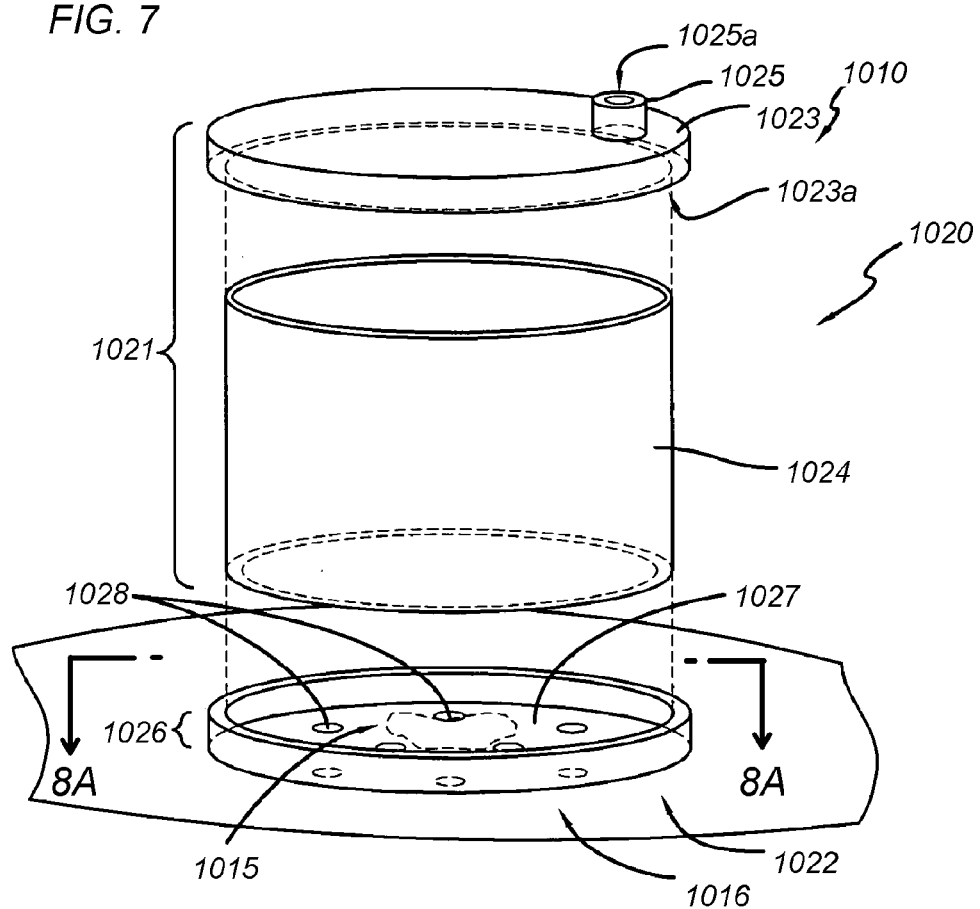
FIG. 7 is an exploded perspective view of an embodiment of a cover, as such cover would appear from above the body of a patient while the cover is positioned on the body.

One embodiment of the invention is the treatment appliance 1010 illustrated in FIG. 7. FIG. 7 is an exploded perspective view of a cover 1020 comprising the treatment appliance 1010 from the side of and above the cover 1020 as it appears when applied to a portion of the body 1016 of a patient surrounding a wound 1015. In this embodiment, the cover 1020 is comprised of a top cup member 1021, an interface member 1022, and interface attachment means, which are described in more detail below, to attach the interface member 1022 to the top cup member 1021. This embodiment also comprises sealing means to seal the cover 1020 to the portion of the body 1016 surrounding the wound 1015, which are described in more detail below, and reduced pressure supply means (not illustrated), which are also described in more detail below. The cover 1020 is generally sized to be placed over and enclose the wound 1015 to be treated. The cover 1020 and the sealing means (described in more detail below) allow reduced pressure to be maintained in the volume under the cover 1020 at the site of the wound 1015 to be treated, as described in more detail below. The reduced pressure supply means are used to operably connect the cover 1020 to a reduced pressure supply source (also not illustrated) in a manner so that the reduced pressure supply source provides a supply of reduced pressure to the cover 1020, so that the volume under the cover 1020 at the site of the wound may be maintained at reduced pressure. It is to be noted, however, that in other embodiments of the present invention, the top cup member 1021 may be used for treatment of a wound 1015 without the interface member 1022. In these embodiments, the top cup member 1021 alone is placed over the wound 1015 and reduced pressure is applied to the volume under the top cup member 1021.

Figure 11:
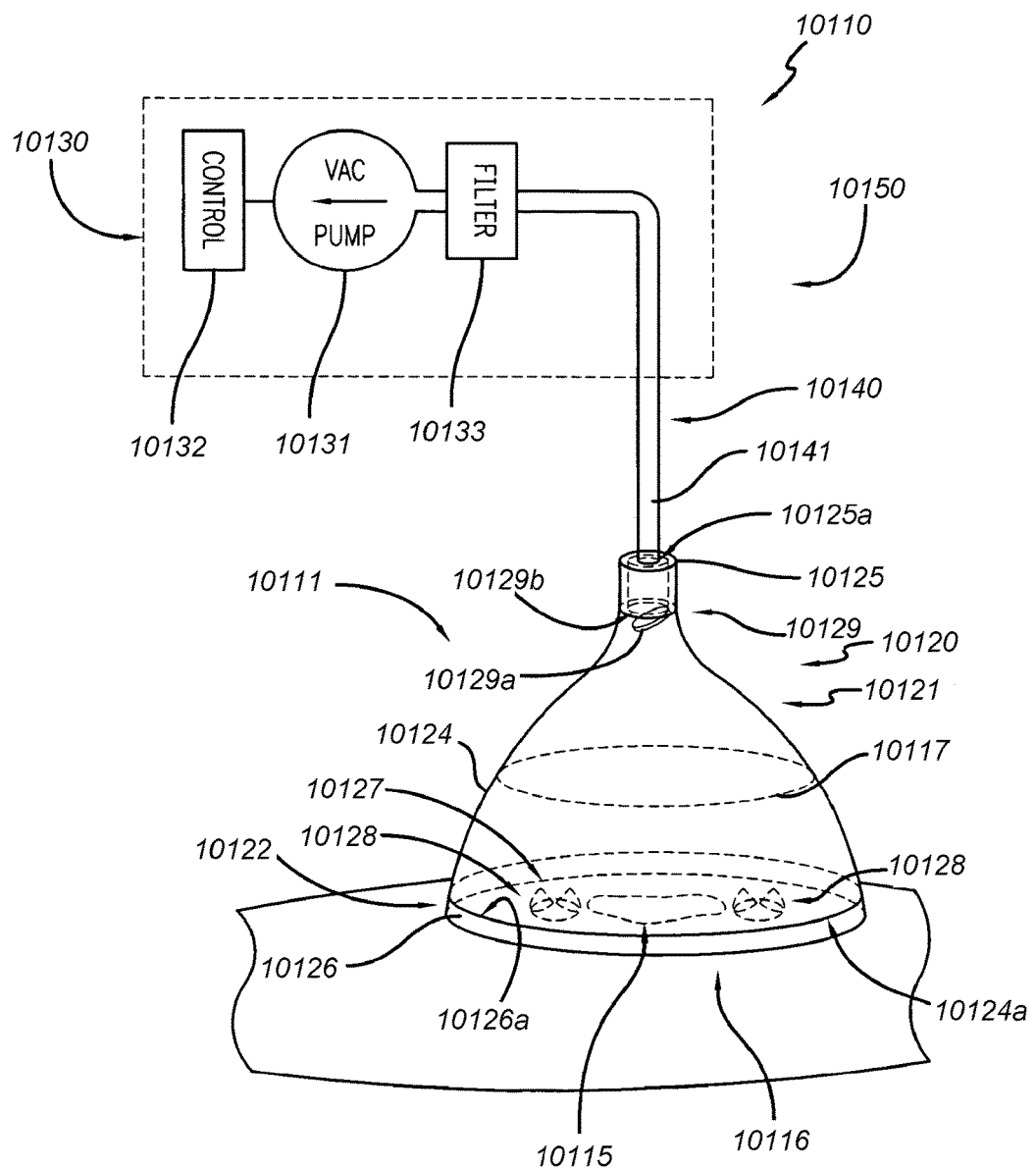
FIG. 11 is a view of an embodiment of a treatment appliance, in which an embodiment of a treatment device, shown in perspective view, is placed over a wound on a body, and in which an embodiment of a vacuum system, depicted generally and shown in schematic elevation view, provides reduced pressure within the volume under a cover comprising the treatment device.

The embodiment of the top cup member 1021 of the cover 1020 illustrated in FIG. 7 is further comprised of a lid member 1023 and a cup body member 1024. In this embodiment, the lid member 1023 is removably or permanently attached to the cup body member 1024 using lid attachment means, which may be substantially the same as any of the interface attachment means, which are described in more detail below. While the lid member 1023 is attached to the cup body member 1024, the lid attachment means provides a gas-tight and liquid-tight seal so that reduced pressure may be maintained in the volume under the cover 1020 in the area of the wound 1015. In the embodiment illustrated in FIG. 7, the top cup member 1021 is approximately cylindrical in shape. In other embodiments, the top cup member 21 may be of almost any shape or combination of shapes, as long as the open end 1023a of the lid member 1023 is of a size and shape adapted to fit against a portion of the surface of the cup body member 1024 in a manner so that an airtight and liquid-tight seal can be maintained by the use of the lid attachment means, as described in more detail below. For example, as illustrated in FIG. 11, the top cup member 10121 of the cover 10120 may be approximately cup-shaped, having an interface member 10122 disposed on its bottom surface. As other examples, the cover 1020, 10120 may be cubical, spherical, spheroidal, hexahedral, polyhedral, or arcuate in shape, or may be comprised of any combination of such shapes, in other embodiments. Thus, referring again to FIG. 7 as an example, the lid member 1023 may also be shaped approximately as a hemisphere or a cone in other embodiments. As another example, in yet other embodiments, the cup body member 1024 and the open end 1023a of the lid member 1023 may have a cross-section of approximately elliptical, square, rectangular, polygonal, arcuate or other shape or combination of all such shapes. The preferred shape and size of the top cup member 1021, 10121, as well as the size and shape of any lid member 1023 comprising it, are dependent upon the materials comprising the cover 1020, 10120, the thickness of the cover 1020, 10120, the nature of the wound to be treated, the size, shape and contour of the portion of the body to be covered by the cover 1020, 10120, the magnitude of the reduced pressure to be maintained under the cover 1020, 10120, the size, shape and other aspects of the interface portion 1022, 10122, the individual preferences of the user of the cover 1020, 10120, and other factors related to access to the wound 1015, the sealing means, and the reduced pressure supply means, as described in more detail below.

In the embodiment of the cover 1020 illustrated in FIG. 7, the lid member 1023 may be detached from the cup body member 1024. This allows the user of the appliance 1010 to have access to the area of the wound 1015 without having to break the sealing means used to operably seal the cover 1020 to the portion of the body 1016 surrounding the wound 1015. The ability to access the wound 1015 in this manner results in more efficient use of the time of healthcare practitioners and less discomfort to patients. It is to be noted that in other embodiments, the lid member 1023 and the cup body member 1024 may be permanently attached together or may be formed as a single piece. For example, the top cup member 10121 of the cover 10120 of FIG. 11 does not have a detachable lid member, but is instead formed as a single piece. In these embodiments, and referring to the cover 1020 of FIG. 7 as an example, the lid member 1023 and the cup body member 1024 may be fabricated as a single piece, such as by injection molding, or they may be attached together by any appropriate means, such as by welding, fusing, adhesives, glues, bolts, screws, pins, rivets, clamps, or other fasteners or means or combinations of all such means. In the embodiment of the present invention illustrated in FIG. 7, the lid member 1023 and the cup body member 1024 are each constructed of a material that is rigid enough to support the cover 1020 away from the wound 1015. Thus, the lid member 1023 and the cup body member 1024 of the cover 1020 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 1020 away from the wound 1015. For example, the lid member 1023 and the cup body member 1024 may each be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments, the lid member 1023 and the cup body member 1024 may be constructed in whole or in part of gas-permeable materials, allowing limited amounts of oxygen to penetrate the lid member 1023 and the cup body member 1024 so that the portion of the body under the cover 1020 in the area of the wound 1015 can "breathe." In some embodiments, all portions of the top cup member 1021 are preferably constructed of one type of semi-rigid material, such as polypropylene. In other embodiments, the top cup member 1021 may be constructed of more than one material. For example, the lid member 1023 may be constructed of silicone and the cup body member 1024 of the cover 1020 may be comprised of polyvinyl chloride, so that the lid member 1023 may be stretched enough to overlap and seal against the outer edge of the cup body member 1024 to form an operable seal, as described in more detail below. The preferred wall thickness of the cover 1020 and its various component parts is dependent upon the size and shape of the cover 1020, the size, shape and contour of the portion of the body to be covered by the cover 1020, the magnitude of the reduced pressure to be maintained under the cover 1020, the materials comprising the cover 1020, and the individual preferences of the user of the cover 1020. For example, in the embodiment of the cover 1020 illustrated in FIG. 7, for a top cup member 1021 constructed entirely of a silicone blend and having an approximate diameter of 4 inches and an approximate height of 3 inches, the preferred wall thickness of the top cup member 1021 is in the range from $\frac{1}{32}$ inches to $\frac{3}{8}$ inches. It is to be noted that in other embodiments the wall thickness of the various portions of the top cup member 1021 may vary from embodiment to embodiment, as well as from portion to portion of the top cup member 1021. Generally, the top cup member 1021 of the illustrated embodiment may be constructed using any suitable means currently known in the art or that may be developed in the art in the future. For example, a top cup member 1021 constructed entirely of a silicone blend may be manufactured by means of injection molding. As another example, embodiments of covers 1020 constructed of different types of materials may be constructed in the manner described above in this paragraph. It is to be noted that embodiments of the top cup member 10121 comprised of one piece, without separate lid member and cup body member as illustrated by the cover 10120 of FIG. 11, the top cup member may be constructed of substantially the same materials, have the same wall thicknesses, and be constructed in substantially the same manner as described above in this paragraph.

In some embodiments of the present invention, as illustrated in FIG. 7, the cover 1020 further comprises a port 1025. The port 1025 is adapted to be of a size and shape so that the reduced pressure supply means may be operably connected to the top cup member 1021 by means of the port 1025. When the port 1025 is operably connected to the reduced pressure supply means, reduced pressure may be supplied to the volume under the cover 1020 at the site of the wound 1015 to be treated. Although the port 1025 is positioned at a location near one side of the lid member 1023 of the enclosure 1020 in the embodiment illustrated in FIG. 7, the port 1025 may be located at other positions on the top cup member 1021 (on either the lid member 1023 or the cup body member 1024) in other embodiments, as long as the port 1025 does not adversely affect the ability of the cup body member 1024 to form an operable seal with the lid member 1023 or the interface member 1022, as described in more detail below. Although the port 1025 may be constructed of a material different from the material comprising the remainder of the top cup member 1021 in various embodiments of the invention, the port 1025 is preferably constructed from the same material comprising the top cup member 1021 of the cover 1020. In the embodiment of the cover 1020 illustrated in FIG. 7, the port 1025 is generally cylindrical in shape and is further comprised of an approximately cylindrical channel 1025a that extends from the top of the port 1025 to the bottom of the port 1025. The port 1025 of this embodiment is thus able to receive a vacuum system or reduced pressure supply means, which are described in more detail below, adapted to be connected to this shape of port 1025 and channel 1025a. In other embodiments of the invention, the port 1025 or the channel 1025a or both may have different shapes and configurations as may be desired to adapt and connect the port 1025 and the channel 1025a to the vacuum system or reduced pressure supply means, which are described in more detail below. In some of the embodiments comprising a port 10125, as illustrated in the embodiment of the cover 10120 of FIG. 11, the top cup member 10121 may be further comprised of flow shutoff means (a one-way valve 10129 in this embodiment), which are operably connected to the port 10125 and described in more detail below. Referring again to FIG. 7 as an example, in other embodiments, a means of connecting the top cup member 1021 to the reduced pressure supply means (described in more detail below) may be located on the top cup member 1021 in lieu of or in conjunction with the port 1025. For example, in some embodiments, the port 1025 may be combined with a variable descending diameter adapter (commonly referred to as a "Christmas tree" adapter), a luer lock fitting, or other similar adapter or fitting.

Figure 8A:
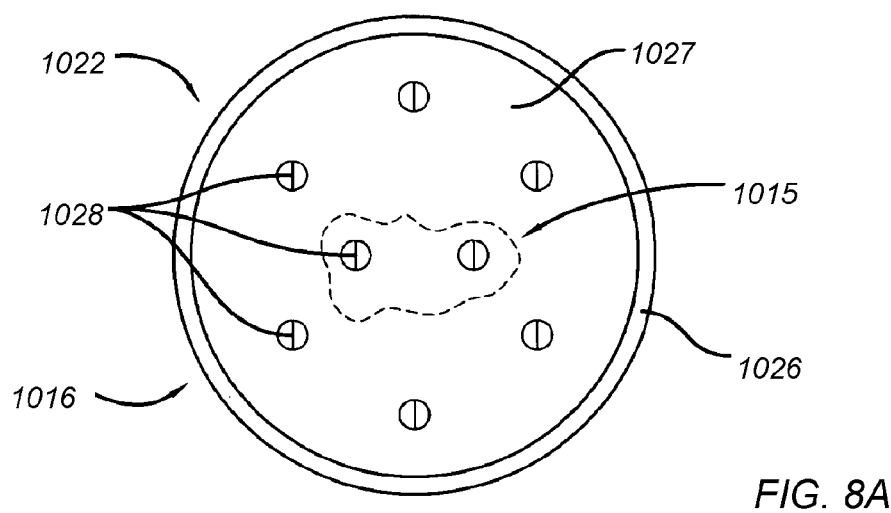
FIG. 8A is an plan view of the interface member of the embodiment of the cover illustrated in FIG. 7, as taken along the lines 8A-8A of FIG. 7.
Figure 8B:
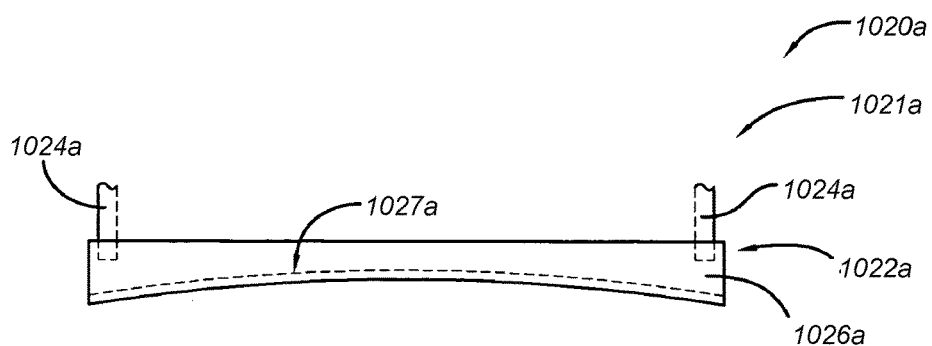
FIG. 8B is an elevation view of another embodiment of an interface member.

In the embodiment of the cover 1020 illustrated in FIG. 7, the interface member 1022 is removably attached to the cup body member 1024 by the interface attachment means (described in more detail below), which are used to make an approximately airtight and liquid-tight seal with the top cup member 1021. In the illustrated embodiment, the interface member 1022 is comprised of a border portion 1026, a membrane portion 1027, and membrane flow control means, which are described in more detail below. The membrane portion 1027 in the illustrated embodiment has an approximately flat surface and is approximately circular in shape when viewed from above. In other embodiments, the membrane portion 1027 may have other shapes. For example, the surface of the membrane portion 1027 may have a curved surface, so that it is concave (similar to a concave lens) in shape. In addition, the interface member 1022 (and its border portion 1026 and membrane portion 1027) may be of almost any shape and size, as long as the interface member 1022 is of a size and shape adapted so that it fits against a portion of the surface of the top cup member 1021 in a manner so that an approximately airtight and liquid-tight seal is maintained by the interface attachment means, as described in more detail below. For example, when viewed from above, the interface member 1022 may have an approximately elliptical, square, rectangular, polygonal, arcuate or other shape or combination of all such shapes. As another example, as illustrated in the embodiment of the interface member 1022a of the cover 1020a illustrated in FIG. 8B, when viewed from the side, the interface member 1022a may appear to have an approximately curved surface so that it may rest on portions of the body that have an approximately curved surface. Thus, in the illustrated embodiment, the border portion 1026a has a generally flat top surface and an approximately concave lower surface bounding the membrane portion 1027a. Also in this embodiment, the interface member 1022a is removably attached to the cup body portion 1024a of the top cup member 1021a using the interface attachment means, which are described in more detail below. It is to be noted that in some embodiments, as illustrated by the embodiment of the cover 10120 in FIG. 11, the top surface of the border portion 10126 of the interface member 10122 may be positioned adjacent to the bottom surface of the top cup member 10121. The preferred shape and size of the interface member 1022, 1022a, 10122, as well as the size and shape of the border portion 1026, 1026a, 10126 and membrane portion 1027, 1027a, 10127 comprising it, are dependent upon the size and shape of the top cup member 1021, 1021a, 10121, materials comprising the cover 1020, 10120, the thickness of the interface member 1022,10 22a, 10122, the nature of the wound to be treated, the size, shape and contour of the portion of the body to be covered by the cover 1020, 1020a, 10120, the magnitude of the reduced pressure to be maintained under the cover 1020, 1020a, 10120, the individual preferences of the user of the cover 1020, 1020a, 10120, and other factors related to the sealing means and interface attachment means, as described in more detail below.

In the embodiment of the present invention illustrated in FIG. 7, the border portion 1026 is constructed of a material that is rigid enough to support the interface member 1022 and the cover 1020 away from the wound. Thus, the border portion 1026 of the cover 1020 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 1020 away from the wound. For example, the border portion 1026 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. In the illustrated embodiment, the membrane portion 1027 is constructed of a material that is strong enough to support the membrane flow control means, which are described in more detail below. Thus, the membrane portion 1027 of the cover 1020 may be comprised of almost any rigid, semi-rigid, or flexible medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the membrane flow control means, which are described in more detail below. For example, the membrane portion 1027 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments, the interface member 1022 may be constructed in whole or in part of gas-permeable materials, allowing limited amounts of oxygen to penetrate the interface member 1022 so that the portion of the body under the cover 1020 can "breathe." In some embodiments, all portions of the interface member 1022 are preferably constructed of one type of semi-rigid material, such as polypropylene. In other embodiments, the interface member 1022 may be constructed of more than one material. For example, the membrane portion 1027 may be constructed of silicone and the border portion 1026 of the cover 1020 may be comprised of polyvinyl chloride, so that the membrane portion 1027 may be more flexible than the border portion 1026. The preferred wall thickness of the interface member 1022 and its various component parts is generally dependent upon the same parameters as described above for the top cup member 1021. Although the interface member 1022 need not be constructed of the same materials as the top cup member 1021, it is preferred that the interface member 1022 be constructed of the same materials as the top cup member 1021. Generally, the interface member 1022 of the illustrated embodiment may be constructed using any suitable means currently known in the art or that may be developed in the art in the future. For example, an interface member 1022 constructed entirely of one material may be manufactured by means of injection molding. As another example, the component parts of an interface member 1022 constructed of different types of materials may be attached together by any appropriate means, such as by welding, fusing, adhesives, glues, bolts, screws, pins, rivets, clamps, or other fasteners or other means or combinations of all such means.

Referring to the embodiment of the cover 1020 illustrated in FIG. 7, the interface member 1022 is further comprised of membrane flow control means, which allow exudate aspirated from the wound 1015 to flow into the volume of the top cup member 1021, but not in the opposite direction. In the illustrated embodiment, the membrane flow control means is comprised of eight flow control valves 1028. It is to be noted that in various embodiments the flow control valves 1028 may be any type of valve currently known in the relevant art or that may be developed in the relevant art in the future that is suitable for operation in reduced pressure environments that allows fluids to flow in one direction through the valve, but not in the opposite direction. For example, such valves 1028 may generally be comprised of sprung or unsprung flapper or disc-type valves. In the illustrated environment, the flow control valves 1028 are comprised of flapper-type valves, which are each further comprised of two flappers that are approximately semi-circular in shape and hinged at their outside edge so that when they fall together they form a seal that only allows fluids to flow in one direction (from the wound 1015 to the volume within the top cup member 1021 in this embodiment). Although the interface member 1022 may have at least one flow control valve 1028 in some embodiments, the interface member 1022 may have almost any number of flow control valves 1028 in other embodiments. For example, as illustrated in FIG. 11, the interface member 10122 may be comprised of two flow control valves 10128. In embodiments of the present invention comprising flow control valves 1028, the preferred number and type of valves 1028 is dependent upon the shape and size of the interface member 1022, the materials comprising the interface member 1022, the thickness of the membrane portion 1027, the nature of the wound 1015 to be treated, the amount of exudate anticipated, the size, shape and contour of the portion of the body to be covered by the cover 1020, the magnitude of the reduced pressure to be maintained under the cover 1020, the individual preferences of the user of the cover 1020, and other factors related to the sealing means, as described in more detail below. It is to be noted that in some embodiments, the flow control valves 1028 may be formed from a single piece with the membrane portion 1027, or may be attached to the membrane portion 1027 using any suitable means, such as by welding, fusing, adhesives, glues, bolts, screws, pins, rivets, clamps, or other fasteners or means or combinations of all such means. In other embodiments, the membrane flow control means may be comprised of a membrane portion 1027 that is constructed in whole or in part of a material that allows fluids to flow in one direction, but not in the opposite direction. In these embodiments, exudate from the wound 1015 flows from the wound 1015 through the membrane portion 1027 (or a portion thereof) to the volume within the top cup member 1021, but does not flow in the reverse direction back to the wound 1015.

Figure 9:
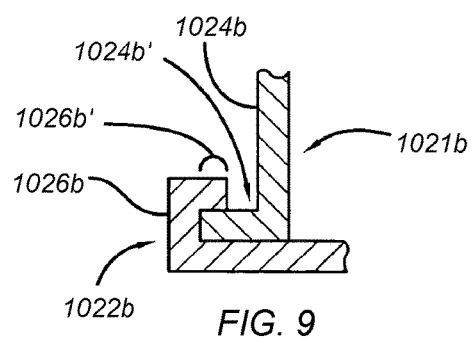
FIG. 9 is an enlarged cross-sectional elevation view of one embodiment of the interface attachment means.
Figure 10:
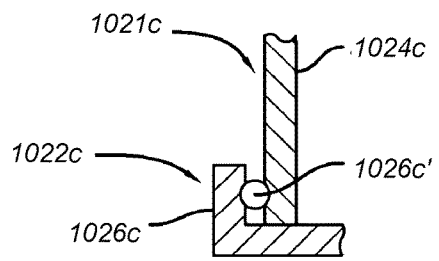
FIG. 10 is an enlarged cross-sectional elevation view of another embodiment of the interface attachment means.

In various embodiments, the interface attachment means, which may be used to removably or permanently attach the interface member 1022 to the top cup member 1021, may be any suitable means currently known in the relevant art or developed in the relevant art in the future that may be used to create an airtight and liquid-tight seal (sometimes referred to herein as an "operable seal") between the interface member 1022 and the top cup member 1021. For example, in the embodiment illustrated in FIG. 9, which is an enlarged cross-sectional elevation view of an interface attachment means, the border portion 1026$b$ is constructed of a semi-rigid material (such as silicone) and has a lip portion 1026$b$' that extends around the perimeter of the interface member 1022$b$. The cup body member 1024$b$ of the top cup member 1021$b$ also has a lip portion 1024$b$' adjacent to the bottom edge of the cup body member 1024$b$ that extends around the perimeter of the bottom edge of the cup body member 1024$b$. In this embodiment, the interface attachment means is comprised of the lip portion 1026$b$' of the interface member 1022$b$ being stretched over the lip portion 1024$b$' of the top cup member 1021, so that the lip portions are joined tightly together to form an operable seal. As another example, as illustrated in FIG. 10, the interface attachment means may be comprised of an o-ring (or gasket or similar sealing means) 1026$c$' that is positioned in a groove extending around the perimeter of the border portion 1026$c$ or the cup body member 1024$c$ or both, so that the o-ring 1026$c$' forms an operable seal between the top cup member 1021$c$ and the interface member 1022$c$. Referring again to FIG. 7 as an example, in still other embodiments, the exterior bottom portion of the cup body member 1024 may be threaded and the interior bottom portion of the border portion 1026 of the interface member 1022 may be of a structure to receive such threads, so that an operable seal is created when the cup body member 1024 is screwed into the interface member 1022. In yet other embodiments, as illustrated in FIG. 11, the interface attachment means may be comprised of a magnetic strip (not shown) attached to the bottom surface 10124$a$ of the cup body member 10124 of the top cup member 10121 and to the top surface 10126$a$ of the border portion 10126 of the interface member 10122, so that such surfaces abut against one another in the manner illustrated in FIG. 11 when the surfaces are attracted by magnetic force, creating an operable seal. Further, the interface attachment means may be comprised of a washer, gasket, o-ring or similar structure (not shown) attached to the bottom surface 10124$a$ of the cup body member 10124 of the top cup member 10121 or to the top surface 10126$a$ of the border portion 10126 of the interface member 10121, or both, so that such surfaces abut against one another in the manner illustrated in FIG. 11, creating an operable seal. In these embodiments, the top cup member 10121 may be held in place against the interface member 10122 by means of clips, brackets, pins, clamps, clasps, adhesives, adhesive tapes, quick-release or other fasteners, or combinations of such means. In addition, many types of sealing means that may be used to removably attach components of kitchenware-type items together may by used as the interface attachment means. It is also to be noted that in other embodiments the interface attachment means may be comprised of means to permanently attach the interface member 1022 to the top cup member 1021 or of forming the interface member 1022 and the top cup member 1021 as a single piece. In these embodiments, and referring to the cover 1020 of FIG. 7 as an example, the interface member 1022 and the top cup member 1021 may be fabricated as a single piece, such as by injection molding, or they may be attached together by any appropriate means, such as by welding, fusing, adhesives, glues, bolts, screws, pins, rivets, clamps, or other fasteners or means or any combinations of all such means. Referring again to FIG. 7 as an example, it is to be noted that the lid attachment means that may be used to removably or permanently attach the lid member 1023 to the cup body member 1021 may have substantially the same structure, features, characteristics and operation as any or all of the embodiments comprising the interface attachment means described above.

Another embodiment of the present invention is the treatment appliance 10110 illustrated in FIG. 11. In this embodiment, the treatment appliance 10110 is comprised of a treatment device 10111 and a vacuum system, generally designated 10150, which is operably connected to, and provides a supply of reduced pressure to, the treatment device 10111. Also in this embodiment, the treatment device 10111 is comprised of a cover 10120. In addition, in this embodiment, the vacuum system 10150 is further comprised of a reduced pressure supply source, generally designated 10130, which is illustrated schematically and described in more detail below, and reduced pressure supply means, generally designated 10140, which are described in more detail below. Also in this embodiment, the reduced pressure supply means 10140 are used to connect the reduced pressure supply source 10130 to the cover 10120 in a manner so that reduced pressure is supplied to the volume under the cover 10120 at the site of the wound 10115 to be treated, as described in more detail below. In the embodiment illustrated in FIG. 11, the illustrated cover 10120 is comprised of a top cup member 10121, an interface member 10122, and interface attachment means to removably attach the top cup member 10121 to the interface member 10122. In the illustrated embodiment, the interface attachment means is comprised of a magnetic strip (not shown) on the top surface 10126a of the border portion 10126 of the interface member 10122 and a magnetic strip (not shown) on the bottom surface 10124a of the cup body member 10124 of the top cup member 10121. An operable seal is formed between the interface member 10122 and the top cup member 10121 by the magnetic attraction of the magnetic strips. In other embodiments, the interface attachment means may be comprised of any of the interface attachment means of the embodiment illustrated and described above in connection with FIG. 7 through FIG. 11. Alternatively, the interface member 10122 and the top cup member 10121 may be formed as a single piece or permanently attached, as illustrated and described above in connection with FIG. 7 through FIG. 11. It is to be noted that in this and other embodiments of the invention, the cover 10120 may have substantially the same structure, features, characteristics, and operation as any embodiment of any of the covers 1020, 1020a, 10120 of the embodiments described above and illustrated in connection with FIG. 7 through FIG. 11. It is also to be noted that in other embodiments of the present invention, the top cup member 10121 may be used for treatment of a wound 10115 without the interface member 10126. In these embodiments, the top cup member 10121 alone is placed over the wound 10115 and reduced pressure is applied to the volume under the top cup member 10121.

In various embodiments of the present invention, as illustrated in FIG. 11, the interface member 10122 of the cover 10120 may be comprised of a semi-rigid material and the sealing means may be comprised of the suction of the interface member 10122 against the portion 10116 of the body adjacent to the interface member 10122 of the cover 10120, such suction being produced by the presence of reduced pressure in the volume under the cover 10120 at the site of the wound 10115. In other embodiments, the sealing means may be comprised of an adhesive, an adhesive tape, lanolin, or other sealant, or any combination of such means, that is disposed between the interface member 10122 and the portion 10116 of the body adjacent to the interface member 10122 or disposed over the interface member 10122 and the portion of the body outside the perimeter of the interface member 10122. In yet other embodiments, the sealing means may be comprised of a material (not illustrated) that is positioned approximately over the cover 10120 and wrapped around the portion 10116 of the body on which the cover 10120 is positioned. This material is used to hold the cover 10120 against the adjacent portion 10116 of the body. For example, if the wound 10115 were on the patient's leg, an elastic bandage or adhesive tape may be wrapped over the cover 10120 and around the leg.

In the embodiment illustrated in FIG. 11, the reduced pressure supply source 10130 of the vacuum system 10150, which produces a source of reduced pressure or suction that is supplied to the cover 10120, is comprised of a vacuum pump 10131, a control device 10132, and a filter 10133. Although the preferred means of producing the reduced pressure or suction is a vacuum pump 10131 in this embodiment, in other embodiments of the invention, other means may be used, such as an outlet port of a centralized hospital vacuum system. In the illustrated embodiment, predetermined amounts of suction or reduced pressure are produced by the vacuum pump 10131. The vacuum pump 10131 is preferably controlled by a control device 10132, such as a switch or a timer that may be set to provide cyclic on/off operation of the vacuum pump 10131 according to user-selected intervals. Alternatively, the vacuum pump 10131 may be operated continuously without the use of a cyclical timer. In addition, in some embodiments the control device 10132 may provide for separate control of the level of reduced pressure applied to the volume under the cover 10120 at the site of the wound 10115 and the flow rate of fluid aspirated from the wound 10115, if any. In these embodiments, relatively low levels of reduced pressure may be maintained at the site of the wound 10115 in the volume under the treatment device 10111, while still providing for the removal of a relatively large volume of exudate from the wound 10115. A filter 10133, such as a micropore filter, is preferably attached to the inlet of the vacuum pump 10131 to prevent potentially pathogenic microbes or aerosols from contaminating, and then being vented to atmosphere by, the vacuum pump 10131. In other embodiments, the filter 10133 may also be a hydrophobic filter that prevents any exudate from the wound 10115 from contaminating, and then being vented to atmosphere by, the vacuum pump 10131. It is to be noted that in other embodiments of the invention, the reduced pressure supply source 10130 may not have a filter 10133 or a control 10132 or any combination of the same.

In other embodiments of the invention, the reduced pressure supply source 10130 of the vacuum system 10150, may be comprised of a small, portable vacuum pump 10131. In some of these embodiments, a filter 10133 or a power source (not illustrated), or both, may also be contained within the housing for the portable vacuum pump 10131. In these embodiments, the portable vacuum pump 10131 is preferably controlled by a control device 10132 that is also located within the housing for the portable vacuum pump 10131, which may provide substantially the same functions as the control device 10132 described above. Except for its smaller size, the portable vacuum pump 10131 may operate in substantially the same manner as the vacuum pump 10131 described above. Also, in these embodiments, the filter 10133 may have the same structure, features, characteristics, and operation, and provide substantially the same functions, as the filter 10133 described above. In some of these embodiments, the filter 10133 may be rigidly connected to the portable vacuum pump 10131. The power source may be any source of energy currently known in the art or that may be developed in the art in the future that may be used to power the portable vacuum pump 10131. For example, in some embodiments, the power source may be a fuel cell, battery or connection to a standard wall electrical outlet.

In the embodiment of the invention illustrated in FIG. 11, the reduced pressure supply means 10140 of the vacuum system 10150, which are used to connect the reduced pressure supply source 10130 to the cover 10120 so that reduced pressure is supplied to the volume under the cover 10120 at the site of the wound 10115, is comprised of at least one tubing member 10141. In this embodiment, the at least one tubing member 10141 is sufficiently flexible to permit movement of the at least one tubing member 10141, but is sufficiently rigid to resist constriction when reduced pressure is supplied to the cover 10120 or when the location of the wound 10115 is such that the patient must sit or lie upon the at least one tubing member 10141 or upon the treatment device 10111. In the embodiment illustrated in FIG. 11, the at least one tubing member 10141 is connected to the cover 10120 by inserting one end of the at least one tubing member 10141 into an opening 10125*a* of a port 10125 of the cover 10120. In this embodiment, the at least one tubing member 10141 is held in place in the opening 10125*a* by means of an adhesive. It is to be noted that in other embodiments of the invention, the at least one tubing member 10141 may be connected to the port 10125 of the cover 10120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 10125 and the at least one tubing member 10141 may be fabricated as a single piece. Similar means may be used to connect the other end of the at least one tubing member 10141 to the vacuum pump 10131 or other reduced pressure supply source 10130 providing the reduced pressure.

In the embodiment of the present invention illustrated in FIG. 11, the treatment device 10111 functions to actively draw fluid or exudate from the wound 10115 through two flow control valves 10128 positioned on the membrane portion 10127 of the interface member 10122 into the interior volume of the cover 10120. In this embodiment, it is generally desirable to collect exudate in the interior volume of the cover 10120, but not to allow the exudate to flow into the reduced pressure supply means 10140 in order to prevent clogging of the vacuum pump 10131. In addition, it is desirable to halt or inhibit the supply of reduced pressure to the cover 10120 in the event that the exudate aspirated from the wound 10115 exceeds a predetermined quantity. Further, it is desirable to interrupt the application of suction to the cover 10120 to prevent exsanguination in the unlikely event a blood vessel ruptures under the cover 10120 during treatment. If, for example, a blood vessel ruptures in the vicinity of the cover 10120, a shutoff mechanism would be useful to prevent the vacuum system 10150 from aspirating any significant quantity of blood from the patient. As a result, the top cup member 10121 in the illustrated embodiment is further comprised of flow shutoff means. In this embodiment, the flow shutoff means is comprised of a flapper-type valve 10129, which is generally comprised of a flapper 10129*a* that is hinged to an interior surface of the port 10125 and seats against a stop 10129*b*. The flapper 10129*a* is buoyant when compared to the exudate, so that it floats upon the exudate as the level of exudate in the volume of the cover 10120 rises to the level of the flapper valve 10129. The flapper 10129*a* is, however, heavy enough not to be drawn against the stop 10129*b* when reduced pressure is applied to the cover 10120 by the vacuum system 10150. Thus, as the exudate level rises to the level of the stop 10129*b*, the flapper 10129*a* floats upon the exudate until the flapper 10129*a* seats against the stop 10129*b*, which seals the cover 10120 so that reduced pressure is no longer supplied to the cover 10120 by the vacuum system 10150. In other embodiments, the flow shutoff means may be comprised of almost any other type of shutoff valve currently known in the relevant art or that may be developed in the relevant art in the future that is suitable for this purpose and use in a reduced pressure environment. Another example of such valve is a float valve, wherein a float ball floats upon the exudate so that the float ball seals against a seat when the level of exudate reaches a predetermined level. All such valves are well known in the relevant art. In other embodiments, other types of mechanisms may also be employed to detect the liquid level within the cover 10120 in order to arrest operation of the vacuum system 10150. In addition, in various embodiments of the invention, the flow shutoff means may be comprised of any means that enables the vacuum system 10150 to halt the supply of reduced pressure to the cover 10120 at any time that the volume of exudate from the wound 10115 exceeds a predetermined amount. Such means may include mechanical switches, electrical switches operably connected to the vacuum system controller 10132, optical, thermal or weight sensors operably connected to the vacuum system controller 10132, and any other means that are currently known in the relevant art or that may be developed in the relevant art in the future.

In some embodiments of the invention, the treatment device 10111 further comprises tissue protection means (not illustrated) to protect and strengthen the surface tissue of the portions 10116 of the body that are adjacent to the cover 10120. The tissue protection means protects such tissue by preventing abrasion and maceration of the tissue. Preferably, the tissue protection means is a hydrocolloid material, such as COLOPAST Hydrocolloid 2655 anhydrous lanolin, or any combination of such hydrocolloid materials. More preferably, the tissue protection means is COLOPAST Hydrocolloid 2655. The tissue protection means may be applied to the body tissue to be protected, or it may be applied to the surface of the cover 10120 that is to be in contact with the body tissue 10116, or both, prior to placing the cover 10120 over the wound 10115. It is to be noted that application of the tissue protection means to the body tissue 10116 that is adjacent to the cover 10120 at the site of the wound 10115 may only entail application of the tissue protection means to the parts of the body tissue 10116 adjacent to the cover 10120 that require such protection.

Referring to FIG. 11, a method of using the treatment appliance 10110 of the illustrated embodiment is also disclosed. In this example, the cover 10120 is removed from an aseptic package in which it is stored. The various component parts of the cover are operably sealed together. For example, in the illustrated embodiment, the top cup member 10121 is operably sealed to the interface member 10122. In embodiments where the top cup member 1021 further comprises a lid member 1023 and a cup body member 1024, as illustrated in FIG. 7, the lid member 1023 and the cup body member 1024 are also operably sealed together. Referring again to FIG. 11, this sealing of the component parts of the cover 10120 may occur before, during or after the cover 10120 is placed over the wound 10115. The cover 10120 is placed over and encloses the wound 10115. The cover 10120 is connected to the vacuum system 10150 by means of the port 10125 on the cover 10120 either before, after or during the placement of the cover 10120 over the wound 10115. Where it is deemed necessary by the user of the treatment appliance 10110, tissue protection means, as described above, may be placed on a portion of the cover 10120, on the body tissue to be protected, or both, prior to placing the cover 10120 over the wound 10115. Reduced pressure is then supplied to the cover 10120 by the vacuum system 10150. In the illustrated embodiment, when reduced pressure is applied to the volume under the cover 10120 at the site of the wound 10115, the cover 10120 is drawn downward by the reduced pressure so that the cover 10120 is drawn tightly against the surface of the adjacent portion 10116 of the body, thus forming an operable seal between the cover 10120 and the portion 10116 of the body adjacent to the cover 10120. References to an "operable seal" and "sealing means" herein refer generally to a seal that may be made gas-tight and liquid-tight for purposes of the reduced pressure treatment of the wound 10115. It is to be noted that this seal need not be entirely gas-tight and liquid-tight. For example, the operable seal may allow for a relatively small degree of leakage, so that outside air may enter the volume under the cover 10120 at the site of the wound 10115, as long as the degree of leakage is small enough so that the vacuum system 10150 can maintain the desired degree of reduced pressure in the volume under the cover 10120 at the site of the wound 10115. As another example, the operable seal formed by the cover 10120 may not be solely capable of maintaining the reduced pressure in the volume under the cover 10120 at the site of the wound 10115 due to the shape of the body portion 10116 at the site of the wound 10115, due to the orientation of the wound 10115, or due to some other reason. In these cases, as well as other cases, it may be necessary or desirable to provide other sealing means (not illustrated), which are described in more detail above. In some embodiments of the present invention comprising a lid member 1023, as illustrated by the cover 1020 of FIG. 7, the method may also comprise one or more of the steps of halting the application of reduced pressure to the cover 1020, removing the lid member 1023 from the cup body member 1024, attending to the wound 10115, re-attaching the lid member 1023 to the cup body member 1024, and then reapplying reduced pressure to the volume under the cover 1020 in the area of the wound 10115. In yet other embodiments, and referring again to FIG. 11, the method may comprise one or more of the steps of monitoring the fluid level 10117 in the volume within the cover 10120, halting the application of reduced pressure to the cover 10120 when the fluid level 10117 reaches a predetermined level, removing the fluid in the volume within the cover 10120, and reapplying reduced pressure to the volume under the cover 1020 in the area of the wound 10115. In some embodiments of the invention, the reduced pressure maintained in the volume under the cover 10120 at the site of the wound 10115 is in the range from approximately 20 mm of Hg below atmospheric pressure to approximately 125 mm of Hg below atmospheric pressure. In yet other embodiments, the reduced pressure is applied to the cover 10120 in a cyclic nature, the cyclic nature providing alternating time periods of application of reduced pressure and non-application of reduced pressure. In various embodiments, the method also comprises the step of maintaining reduced pressure in the volume under the cover 10120 at the site of the wound 10115 until the wound 10115 has progressed toward a selected stage of healing.

Figure 12:
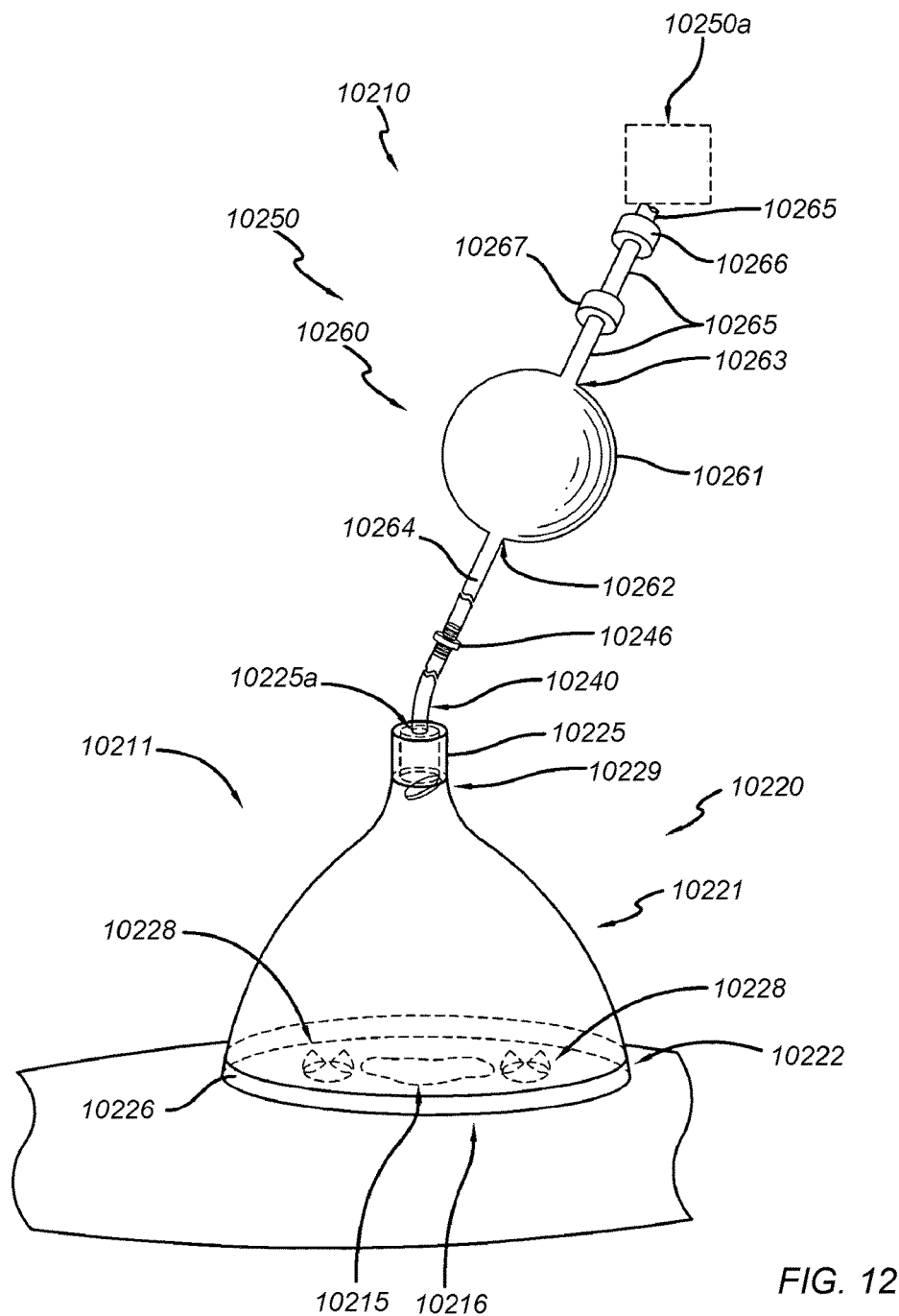
FIG. 12 is a view of an embodiment of a treatment appliance, in which an embodiment of a treatment device, shown in perspective view from the side of and above the treatment device, is positioned over a wound on a body, and in which an embodiment of a vacuum system, shown in elevational view, provides reduced pressure within the volume under a cover comprising the treatment device.

Another embodiment of the invention is the treatment appliance 10210 illustrated in FIG. 12. In this embodiment, the treatment appliance 10210 is comprised of a treatment device 10211 and a vacuum system, generally designated 10250, operably connected to, and providing a supply of reduced pressure to, the treatment device 10211. In addition, in this embodiment, the vacuum system 10250 is further comprised of a reduced pressure supply source, generally designated 10260, which is described in more detail below, and reduced pressure supply means 10240, which are described in more detail below. Also in this embodiment, the treatment device 10211 is further comprised of a cover 10220, which generally has substantially the same structure, features, and characteristics as the embodiment of the cover 10120 illustrated and described above in connection with FIG. 11. It is to be noted, however, that in other embodiments of the invention, the cover 10220 may have substantially the same structure, features, characteristics, and operation as any embodiment of all of the covers 1020, 1020*a*, 10120 of the embodiments of the invention described above and illustrated in connection with FIG. 7 through FIG. 11. In the embodiment illustrated in FIG. 12, the cover 10220 is placed over and encloses a wound 10215. In the illustrated embodiment, the cover 10220 may be sealed to the adjacent portions 10216 of the body using any of the sealing means or operable seals described above and illustrated in connection with FIG. 11.

In the embodiment of the invention illustrated in FIG. 12, the vacuum system 10250 is generally comprised of a suction bulb 10261 having an inlet port 10262 and an outlet port 10263, a bulb connection tubing member 10264, an exhaust tubing member 10265, an exhaust control valve 10266, a filter 10267, and a supplemental vacuum system (illustrated schematically and generally designated 10250*a*). In this embodiment, the suction bulb 10261 is a hollow sphere that may be used to produce a supply of reduced pressure for use with the treatment device 10211. In addition, in some embodiments, the suction bulb 10261 may also be used to receive and store exudate aspirated from the wound 10215. The inlet port 10262 of the suction bulb 10261 is connected to one end of the bulb connection tubing member 10264, which is connected to the reduced pressure supply means 10240, a tubing member in this embodiment, by means of a connector 10246. The connection tubing member 10264 is connected to the reduced pressure supply means 10240 in a manner so that the interior volume of the suction bulb 10261 is in fluid communication with the volume under the cover 10220 in the area of the wound 10215. In this embodiment, the bulb connection tubing member 10264 and the reduced pressure supply means 10240 are sufficiently flexible to permit movement of the bulb connection tubing member 10264 and the reduced pressure supply means 10240, respectively, but are sufficiently rigid to resist constriction when reduced pressure is supplied to the cover 10220 or when the location of the wound 10215 is such that the patient must sit or lie upon the bulb connection tubing member 10264, upon the reduced pressure supply means 10240, or upon the treatment device 10311. The outlet port 10263 of the suction bulb 10261 is connected to the exhaust tubing member 10265. In this embodiment, the exhaust tubing member 10265 is sufficiently flexible to permit movement of the exhaust tubing member 10265, but is sufficiently rigid to resist constriction when reduced pressure is supplied to the cover 10220. The inlet port 10262 of the suction bulb 10261 may be connected to the bulb connection tubing member 10264 and the outlet port 10263 of the suction bulb 10261 may be connected to the exhaust tubing member 10265 using any suitable means, such as by welding, fusing, adhesives, clamps, or any combination of such means. In addition, in some embodiments, the suction bulb 10261, the bulb connection tubing member 10264, and the exhaust tubing member 10265 may be fabricated as a single piece. In the illustrated embodiment, the exhaust control valve 10266 and the filter 10267 are operably connected to the exhaust tubing member 10265. In this embodiment, the exhaust control valve 10266 is used to regulate the flow of fluids (gases and liquids) to and from the suction bulb 10261 and the supplemental vacuum system 10250a. In embodiments of the invention that do not have a supplemental vacuum system 10250a, the exhaust control valve 10266 regulates flow of fluids to and from the suction bulb 10261 and the outside atmosphere. Generally, the exhaust control valve 10266 allows fluids to flow out of the suction bulb 10261 through the outlet port 10263, but not to flow in the reverse direction unless permitted by the user of the appliance 10210. Any type of flow control valve may be used as the exhaust control valve 10266, as long as the valve 10266 is capable of operating in the anticipated environment involving reduced pressure and wound 10215 exudate. Such valves are well known in the relevant art, such as sprung and unsprung flapper-type valves and disc-type valves, operating in conjunction with or without ball, gate and other similar types of valves. In this embodiment, the filter 10267 is operably attached to the exhaust tubing member 10265 between the outlet port 10263 of the suction bulb 10261 and the exhaust control valve 10266. The filter 10267 prevents potentially pathogenic microbes or aerosols from contaminating the exhaust control valve 10266 (and supplemental vacuum system 10250a), and then being vented to atmosphere. The filter 10267 may be any suitable type of filter, such as a micropore filter. In other embodiments, the filter 10267 may also be a hydrophobic filter that prevents any exudate from the wound 10215 from contaminating the exhaust control valve 10266 (and the supplemental vacuum system 10250a) and then being vented to atmosphere. In still other embodiments, the filter 10267 may perform both functions. It is to be noted, however, that the outlet port 10263, the exhaust control valve 10266, the filter 10267, or any combination of the exhaust control valve 10266 and the filter 10267, need not be utilized in connection with the vacuum system 10250 in other embodiments of the invention.

In some embodiments of the invention illustrated in FIG. 12 that do not utilize a supplemental vacuum system 10250a, the suction bulb 10261 may be used to produce a supply of reduced pressure in the following manner. First, the user of the appliance 10210 appropriately seals all of the component parts of the appliance 10210 in the manner described herein. For example, the top cup member 10221 of the cover 10220 is operably sealed to the interface member 10222 of the cover 10220, and the cover 10220 is placed over and encloses the wound 10215. At least a portion of the interface member 10222 is sealed (or placed adjacent) to the adjacent portions 10216 of the body, and the reduced pressure supply means 10240 is connected to the bulb connection tubing member 10264 by means of the connector 10246. The user then opens the exhaust control valve 10266 and applies force to the outside surface of the suction bulb 10261, deforming it in a manner that causes its interior volume to be reduced. When the suction bulb 10261 is deformed, the gas in the interior volume is expelled to atmosphere through the outlet port 10263, the exhaust tubing member 10265, the filter 10267, and the exhaust control valve 10266. The user then closes the exhaust control valve 10266 and releases the force on the suction bulb 10261. The suction bulb 10261 then expands, drawing gas from the area of the wound 10215 under the treatment device 10211 into the suction bulb 10261 and causing the pressure in such area to decrease. To release the reduced pressure, the user of the appliance 10210 may open the exhaust control valve 10266, allowing atmospheric air into the interior volume of the suction bulb 10261. The level of reduced pressure may also be regulated by momentarily opening the exhaust control valve 10266.

The suction bulb 10261 may be constructed of almost any fluid impermeable flexible or semi-rigid material that is suitable for medical use and that can be readily deformed by application of pressure to the outside surface of the suction bulb 10261 by users of the appliance 10210 and still return to its original shape upon release of the pressure. For example, the suction bulb 10261 may be constructed of rubber, neoprene, silicone, or other flexible or semi-rigid polymers, or any combination of all such materials. In addition, the suction bulb 10261 may be of almost any shape, such as cubical, ellipsoidal, or polyhedral. The suction bulb 10261 may also be of varying size depending upon the anticipated use of the suction bulb 10261, the size of the wound treatment device 10211, use of a supplemental vacuum system 10250a, the level of reduced pressure desired, and the preference of the user of the appliance 10210. In the embodiment of the invention illustrated in FIG. 12, the supplemental vacuum system 10250a is connected to the exhaust tubing member 10265 and is used to provide a supplemental supply of reduced pressure to the suction bulb 10261 and treatment device 10211. In this embodiment, the supplemental vacuum system 10250a may have substantially the same structure, features, characteristics and operation of the various embodiments of the vacuum system 10250 of the invention described above and illustrated in connection with FIG. 11. It is to be noted, however, that the supplemental vacuum system 10250a need not be used in connection with the vacuum system 10250 in other embodiments of the invention.

Except as illustrated and described above in connection with FIG. 12, the treatment appliance 10210 may generally be used in a manner similar to the treatment appliance 10110 described above and illustrated in connection with FIG. 11. As a result, except as described herein, the example of how the embodiment of the treatment appliance 10110 and the cover 10120 described above and illustrated in connection FIG. 11 may be used in treatment of a wound 10115 also applies to the embodiment of the appliance 10210 of the invention described above and illustrated in connection with FIG. 12.

What is claimed is:

1. A wound therapy device, comprising:
   a cover to cover at least a portion of a wound site;
   a collection chamber beneath the cover, wherein the collection chamber collects and stores wound fluids from the wound site, and wherein the collection chamber retains collected wound fluids stored therein upon application of negative pressure thereto;
   an opening in the cover configured to be in fluid communication with a vacuum source for creating negative pressure within at least the collection chamber;

a conduit in fluid communication with the opening, the conduit configured to connect to the vacuum source; and a filter at the opening, the filter positioned directly over the collection chamber and configured to preclude migration of liquid collected and stored within the collection chamber through the opening and into the vacuum source, while simultaneously allowing application of negative pressure through the filter and passage of air through the filter in a direction of the vacuum source.

2. The wound therapy device of claim 1, further comprising a seal for sealing the cover to a body surface of a patient.

3. The wound therapy device of claim 1, wherein the cover is constructed of a rigid or semi-rigid material.

4. The wound therapy device of claim 3, wherein the cover material is chosen from at least one of rubber, silicone, polyvinyl chloride, polystyrene, polypropylene, and polyurethane.

5. The wound therapy device of claim 1, wherein the cover comprises a flexible material.

6. The wound therapy device of claim 1, wherein the cover is configured to prevent significant collapse of the collection chamber when subject to a pressure lower than atmospheric pressure.

7. The wound therapy device of claim 1, further comprising foam beneath the collection chamber.

8. The wound therapy device of claim 1, comprising a porous membrane for retaining wound fluids within the collection chamber.

9. The wound therapy device of claim 1, further comprising a wound packing means chosen from: absorbent dressing, antiseptic dressing, nonadherent dressing, water dressing, absorbable matrix, gauze, foam, or combinations thereof.

10. The wound therapy device of claim 1, further comprising an antiseptic dressing.

11. The wound therapy device of claim 1, wherein the opening comprises a vacuum port configured to be coupled to the conduit, wherein the filter is located in the vacuum port.

12. The wound therapy device of claim 1, wherein the opening is coupled to a portable vacuum source disposed adjacent the wound.

13. The wound therapy device of claim 1, further comprising a switch to halt the supply of negative pressure to the cover at any time that the volume of wound fluids from the wound exceeds a predetermined amount.

14. The wound therapy device of claim 1, further comprising a shutoff mechanism for halting or inhibiting the supply of the negative pressure to the cover in the event that the wound fluids aspirated from the wound exceeds a predetermined quantity.

15. The wound therapy device of claim 14, wherein the shutoff mechanism provides a signal that prompts a deactivation of the vacuum source.

16. The wound therapy device of claim 1, wherein the cover is constructed of plastic chosen from: rubber, silicone, silicone blends, silicone substitutes, polyester, vinyl, polyimide, polyethylene napthalate, polycarbonates, polyester-polycarbonate blends, or a similar polymer, or combinations of all such materials.

17. The wound therapy device of claim 1, further comprising tissue protections means.

18. The wound therapy device of claim 17, wherein the tissue protection means comprises multiple layers.

19. The wound therapy device of claim 17, wherein the tissue protection means is configured to be disposed adjacent the wound.

20. The wound therapy device of claim 17, wherein the tissue protection means is at least one of the following: absorbent dressing, antiseptic dressing, nonadherent dressing, water dressing, absorbable matrix, gauze, foam, or combinations thereof.

21. The wound therapy device of claim 1, wherein the cover is semi-permeable.

22. The wound therapy device of claim 21, wherein the semi-permeable cover is gas-permeable.

23. The wound therapy device of claim 1, wherein the cover is cup-shaped.

24. The wound therapy device of claim 1, wherein the cover is a flexible overlay.

25. The wound therapy device of claim 1, wherein the collection chamber collects and stores liquids from the wound site, and wherein the collection chamber retains the collected liquids stored therein upon application of negative pressure thereto.

26. The wound therapy device of claim 1, wherein the opening extends through the wound cover.

27. A wound therapy device, comprising:

a cover to cover at least a portion of a wound site;

a vacuum source, the vacuum source configured to continuously supply negative pressure while in use;

a collection chamber beneath the cover, wherein the collection chamber collects and stores wound fluids from the wound site, and wherein the collection chamber retains collected wound fluids stored therein upon application of negative pressure thereto;

an opening in the cover configured to be in fluid communication with the vacuum source for creating negative pressure within the collection chamber; and a filter at the opening, the filter positioned directly over the collection chamber and configured to preclude migration of liquid collected and stored within the collection chamber through the opening, while simultaneously allowing application of negative pressure through the filter and passage of air through the filter in a direction of the vacuum source.

* * * * *

UNITED STATES PATENT AND TRADEMARK OFFICE
CERTIFICATE OF CORRECTION

PATENT NO. : 10,058,642 B2
APPLICATION NO. : 12/941390
DATED : August 28, 2018
INVENTOR(S) : Richard Scott Weston It is certified that error appears in the above-identified patent and that said Letters Patent is hereby corrected as shown below:

On the Title Page

Column 1, Item (63), under Related U.S. Application Data, Line 9, please change "continuation" to --continuation-in-part--

On Page 16, Column 2, Item (56), under Other Publications, Line 26, change "I nternational" to --International--

In the Specification

In Column 19, Line 26, change "overlay." to --overlay;--

In Column 21, Line 62, change "to noted," to --to be noted,--

In Column 23, Line 16, change "napthalate," to --naphthalate,--

In Column 24, Line 2, change "20cfurther" to --20c further--

In Column 24, Line 5, change "20c.Although" to --20c. Although--

In Column 24, Line 21, change "20abecause" to --20a because--

In Column 24, Line 26, change "20a,and" to --20a, and--

In Column 24, Line 36, change "27a,27b" to --27a, 27b--

In Column 24, Line 39, change "27b,respectively," to --27b, respectively,--

In Column 24, Line 44, change "27b,respectively," to --27b, respectively,--

Signed and Sealed this
Twelfth Day of February, 2019

Andrei Iancu
*Director of the United States Patent and Trademark Office*

CERTIFICATE OF CORRECTION (continued)
U.S. Pat. No. 10,058,642 B2

In Column 24, Line 45, change "28a'" to --28a',--

In Column 24, Line 47, change "28a'" to --28a',--

In Column 24, Line 49, change "27b,respectively," to --27b, respectively,--

In Column 24, Line 50, change "28a'" to --28a',--

In Column 27, Line 41, change "COLOPAST" to --COLOPLAST--

In Column 27, Line 44, change "COLOPAST" to --COLOPLAST--

In Column 50, Line 61, change "by" to --be--

In Column 54, Line 47, change "COLOPAST" to --COLOPLAST--

In Column 54, Line 49, change "COLOPAST" to --COLOPLAST--

In the Claims

In Column 60, Line 4, Claim 16, change "napthalate," to --naphthalate,--